United States Patent
Kang et al.

(10) Patent No.: US 10,319,921 B2
(45) Date of Patent: Jun. 11, 2019

(54) COMPOSITION FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si, Gyeonggi-do (KR)

(72) Inventors: Dong Min Kang, Suwon-si (KR); Youngkwon Kim, Suwon-si (KR); Changwoo Kim, Suwon-si (KR); Eun Sun Yu, Suwon-si (KR); Byoungkwan Lee, Suwon-si (KR); Hanill Lee, Suwon-si (KR); Sung-Hyun Jung, Suwon-si (KR); SooYoung Jeong, Suwon-si (KR); Ho Kuk Jung, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/628,901

(22) Filed: Jun. 21, 2017

(65) Prior Publication Data
US 2018/0026205 A1    Jan. 25, 2018

(30) Foreign Application Priority Data

Jul. 19, 2016  (KR) ......................... 10-2016-0091511

(51) Int. Cl.

| | | |
|---|---|---|
| H01L 51/00 | (2006.01) | |
| C07D 487/04 | (2006.01) | |
| C07D 493/04 | (2006.01) | |
| C07D 495/04 | (2006.01) | |
| C07D 209/82 | (2006.01) | |
| C07D 247/02 | (2006.01) | |
| C07D 401/14 | (2006.01) | |
| C09K 11/06 | (2006.01) | |
| H01L 51/50 | (2006.01) | |
| H05B 33/20 | (2006.01) | |

(52) U.S. Cl.
CPC ........ *H01L 51/0072* (2013.01); *C07D 209/82* (2013.01); *C07D 247/02* (2013.01); *C07D 401/14* (2013.01); *C07D 487/04* (2013.01); *C07D 493/04* (2013.01); *C07D 495/04* (2013.01); *C09K 11/06* (2013.01); *H01L 51/5024* (2013.01); *H01L 51/5056* (2013.01); *H05B 33/20* (2013.01); *C09K 2211/1029* (2013.01); *C09K 2211/1044* (2013.01); *H01L 2251/53* (2013.01)

(58) Field of Classification Search
CPC . H01L 51/0072; C07D 487/04; C07D 493/04; C07D 495/04
See application file for complete search history.

(56) References Cited

U.S. PATENT DOCUMENTS

| | | | |
|---|---|---|---|
| 8,637,857 B2 | 1/2014 | Langer et al. | |
| 8,795,848 B2 | 8/2014 | Kai et al. | |
| 2011/0266528 A1 | 11/2011 | Langer et al. | |
| 2017/0271598 A1* | 9/2017 | Zeng | H01L 51/0072 |

FOREIGN PATENT DOCUMENTS

| | | |
|---|---|---|
| CN | 104271700 A | 1/2015 |
| CN | 105473684 A | 4/2016 |
| JP | 4870245 B2 | 2/2012 |
| JP | 5238025 B2 | 7/2013 |
| JP | 5646733 B2 | 12/2014 |
| JP | 5723794 B2 | 5/2015 |
| KR | 10-2011-0079402 A | 7/2011 |
| KR | 10-2012-0052879 A | 5/2012 |
| KR | 10-2013-0084093 A | 7/2013 |
| KR | 10-2013-0112342 A | 10/2013 |
| KR | 10-1324788 B1 | 10/2013 |
| KR | 10-2013-0127563 A | 11/2013 |
| KR | 10-1423066 B1 | 7/2014 |
| KR | 10-1447959 B1 | 10/2014 |
| KR | 10-2015-0083787 A | 7/2015 |
| WO | WO 2009/148062 A1 | 12/2009 |
| WO | WO 2012/114928 A1 | 8/2012 |
| WO | WO 2013/088973 A1 | 4/2015 |
| WO | WO 2015/182872 A1 | 12/2015 |

OTHER PUBLICATIONS

Office Action dated Oct. 18, 2018 dated Oct. 10, 2018, of the corresponding Chinese Patent Application No. 201710586173.X.

* cited by examiner

*Primary Examiner* — Matthew P Coughlin
(74) *Attorney, Agent, or Firm* — Lee & Morse, P.C.

(57) ABSTRACT

Disclosed are a composition for an organic optoelectronic device includes at least one of a first host compound represented by a combination of Chemical Formula 1 and Chemical Formula 2, and at least one of a second host compound represented by a combination of Chemical Formula 3 and Chemical Formula 4, and an organic optoelectronic device including the same, and a display device.
Details of Chemical Formula 1 to 4 are the same as described in the detailed description.

13 Claims, 1 Drawing Sheet

COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATION

Korean Patent Application No. 10-2016-0091511, filed on Jul. 19, 2016, in the Korean Intellectual Property Office, and entitled: "Composition for Organic Optoelectronic Device and Organic Optoelectronic Device and Display Device," is incorporated by reference herein in its entirety.

BACKGROUND

1. Field

A composition for an organic optoelectronic device, an organic optoelectronic device, and a display device are disclosed.

2. Description of the Related Art

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY

An embodiment provides a composition for an organic optoelectronic device capable of realizing an organic optoelectronic device having high efficiency and a long life-span.

Another embodiment provides an organic optoelectronic device including the composition.

Yet another embodiment provides a display device including the organic optoelectronic device.

According to an embodiment, a composition for an organic optoelectronic device includes at least one of a first host compound represented by a combination of Chemical Formula 1 and Chemical Formula 2, and at least one of a second host compound represented by a combination of Chemical Formula 3 and Chemical Formula 4.

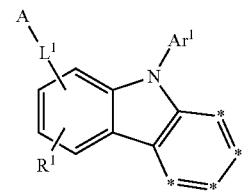

[Chemical Formula 1]

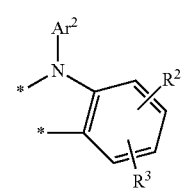

[Chemical Formula 2]

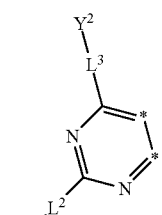

[Chemical Formula 3]

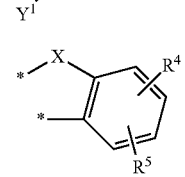

[Chemical Formula 4]

In Chemical Formulae 1 to 4, two adjacent *'s of Chemical Formula 1 are bound to two adjacent *'s of Chemical Formula 2 and the remainder *'s of Chemical Formula 1 not being bound to *'s of Chemical Formula 2 are $CR^a$, two adjacent *'s of Chemical Formula 3 are bound to two *'s of Chemical Formula 4, the substituent A is a substituted or unsubstituted carbazolyl group, $Ar^1$ and $Ar^2$ are independently a substituted or unsubstituted C6 to C30 aryl group, $L^1$ to $L^3$ are independently a single bond or a substituted or unsubstituted C6 to C30 arylene group, X is O or S, $Y^1$ and $Y^2$ are independently deuterium, a substituted or unsubstituted C1 to C10 alkyl group, a substituted or unsubstituted C6 to C30 aryl group, or a substituted or unsubstituted C2 to C30 heterocyclic group, at least one of $Y^1$ and $Y^2$ is a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group, $R^a$ and $R^1$ to $R^5$ are independently hydrogen, deuterium, a substituted or unsubstituted C1 to C10 alkyl group, a substituted or unsubstituted C6 to C20 aryl group, or a combination thereof, and the "substituted" refers to replacement of at least one hydrogen by deuterium, a C1 to C4 alkyl group, a C6 to C12 aryl group, or a C2 to C20 heterocyclic group.

According to another embodiment, an organic optoelectronic device includes an anode and a cathode facing each other and at least one organic layer disposed between the anode and the cathode, wherein the organic layer includes the composition for an organic optoelectronic device.

According to yet another embodiment, a display device including the organic optoelectronic device is provided.

An organic optoelectronic device having high efficiency and a long life-span may be realized.

DETAILED DESCRIPTION

Figure 1:
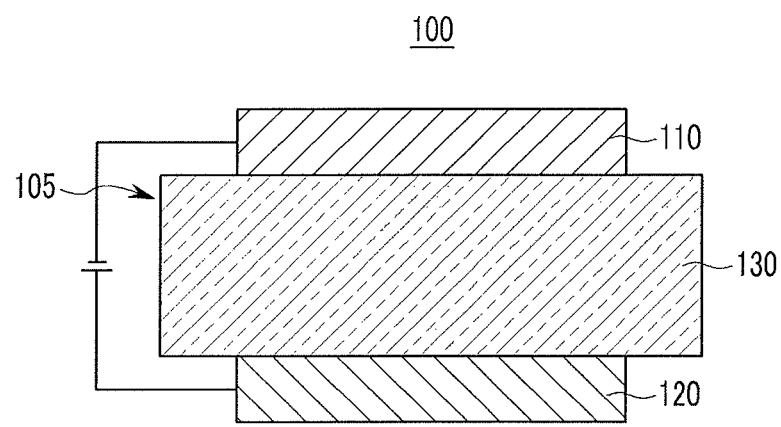
FIGS. 1 and 2 illustrate cross-sectional views showing organic light emitting diodes according embodiments.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C6 to C20 arylamine group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

As used herein, when a definition is not otherwise provided, "hetero" refers to one including one to three heteroatoms selected from N, O, S, P, and Si, and remaining carbons in one functional group.

As used herein, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "an aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, a quinazolyl group, a quinoxalinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted isoquinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes at least two kinds of a host and a dopant, and the host includes a first host compound having relatively strong hole characteristics and a second host compound having relatively strong electron characteristics.

The first host compound is a compound having relatively strong electron transport characteristics and is represented by a combination of Chemical Formulae 1 and 2.

[Chemical Formula 1]

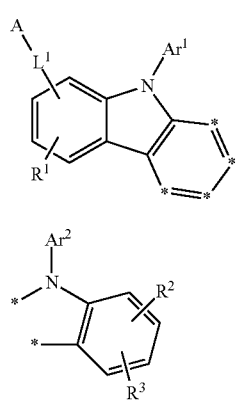

[Chemical Formula 2]

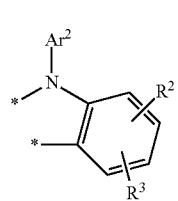

In Chemical Formulae 1 and 2, two adjacent *'s of Chemical Formula 1 are bound to two adjacent *'s of Chemical Formula 2 and the remainder *'s of Chemical Formula 1 not being bound to *'s of Chemical Formula 2 are $CR^a$, the substituent A is a substituted or unsubstituted carbazolyl group, $Ar^1$ and $Ar^2$ are independently a substituted or unsubstituted C6 to C30 aryl group, $L^1$ is a single bond or a substituted or unsubstituted C6 to C30 arylene group, and $R^a$ and $R^1$ to $R^3$ are independently hydrogen, deuterium, a substituted or unsubstituted C1 to C10 alkyl group, a substituted or unsubstituted C6 to C20 aryl group, or a combination thereof.

In an example embodiment, $R^a$ may independently be hydrogen, deuterium, a substituted or unsubstituted C1 to C4 alkyl group, a substituted or unsubstituted phenyl group, a substituted or unsubstituted biphenyl group, a substituted or unsubstituted naphthyl group, or a combination thereof. In a specific example embodiment, $R^a$ may independently be hydrogen, deuterium, a substituted or unsubstituted phenyl group, or a combination thereof, and for example $R^a$ may be all hydrogen.

The first host compound has hole characteristics fortified by substituting an indolocarbazole moiety with an aryl group and the like along with a carbazolyl group and also hole injection/transport characteristics further fortified by making a HOMO energy level close to energy of a dopant and accordingly, may supplement a host having fast electron transport characteristics and contribute to manufacturing a device having a low driving voltage and high efficiency.

Particularly, when an N-carbazolyl group is linked with the indolocarbazole moiety, the first host compound may decrease three-dimensional planarity of a molecular structure and may lower crystallinity and a deposition temperature and thus increase stability.

In the present disclosure, "substituted" of Chemical Formulae 1 and 2 refers to replacement of at least one hydrogen by deuterium, a C1 to C4 alkyl group, a C6 to C12 aryl group, or a C2 to C20 heterocyclic group. In an example embodiment, "substituted" of Chemical Formulae 1 and 2 refers to replacement of at least one hydrogen by a methyl group, an ethyl group, a propyl group, a phenyl group, or a biphenyl group, and specifically "substituted" of Chemical Formulae 1 and 2 refers to replacement of at least one hydrogen by a phenyl group or a biphenyl group.

In an example embodiment, Chemical Formula 1 may be for example represented by Chemical Formula 1-I or Chemical Formula 1-II according to a linking point of the substituent A, the carbazolyl group.

[Chemical Formula 1-I]

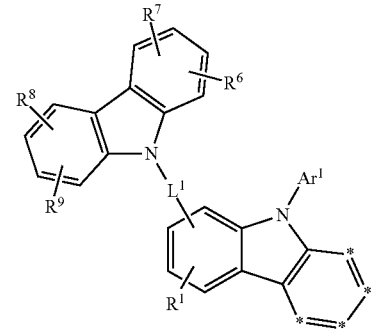

[Chemical Formula 1-II]

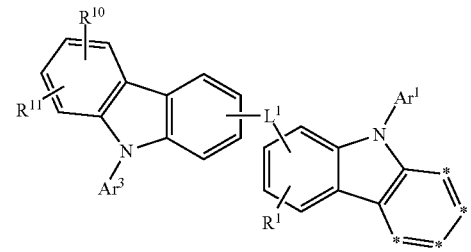

In Chemical Formulae 1-I and 1-II, "*" and $L^1$ are the same as above, $R^1$ and $R^6$ to $R^{11}$ are independently hydrogen, deuterium, a substituted or unsubstituted C1 to C4 alkyl group, a substituted or unsubstituted C6 to C12 aryl group, or a substituted or unsubstituted C2 to C20 heterocyclic group, and $Ar^1$ and $Ar^3$ are independently a substituted or unsubstituted C6 to C30 aryl group.

In an example embodiment, the $L^1$ may independently be a single bond or a substituted or unsubstituted C6 to C20 arylene group, specifically the $L^1$ may be a single bond, a substituted or unsubstituted phenylene group, a substituted or unsubstituted biphenylene group, or a substituted or unsubstituted terphenylene group, and may be for example selected from linking groups of Group I.

[Group I]

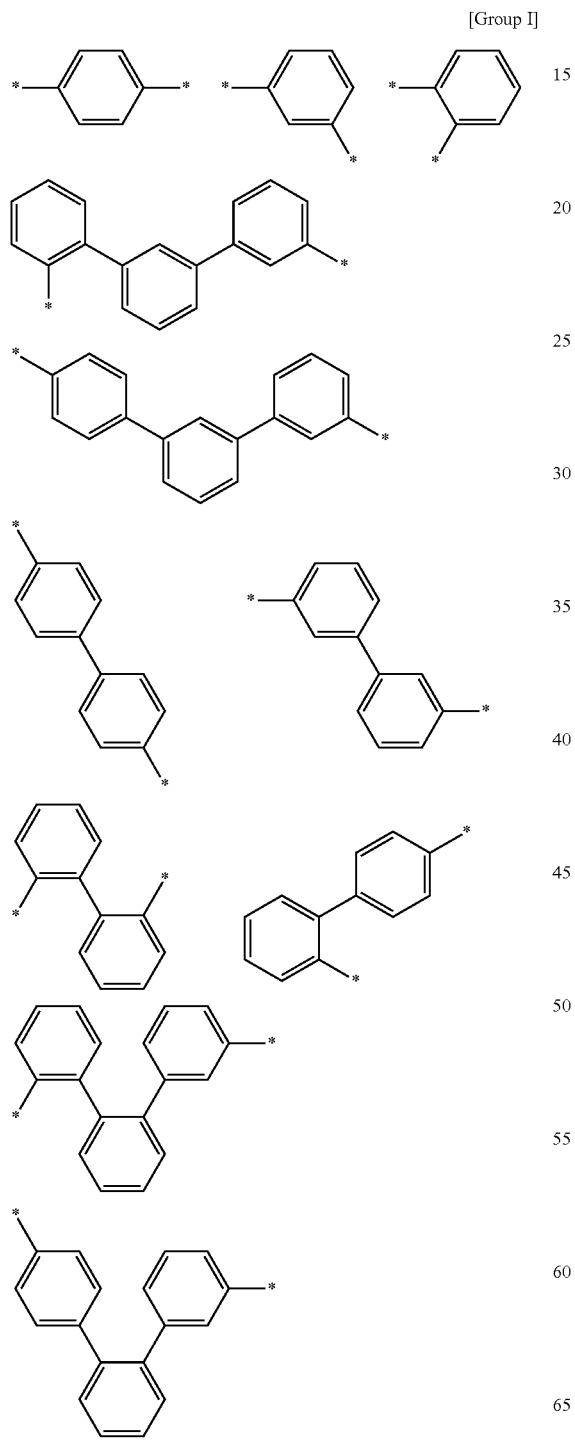
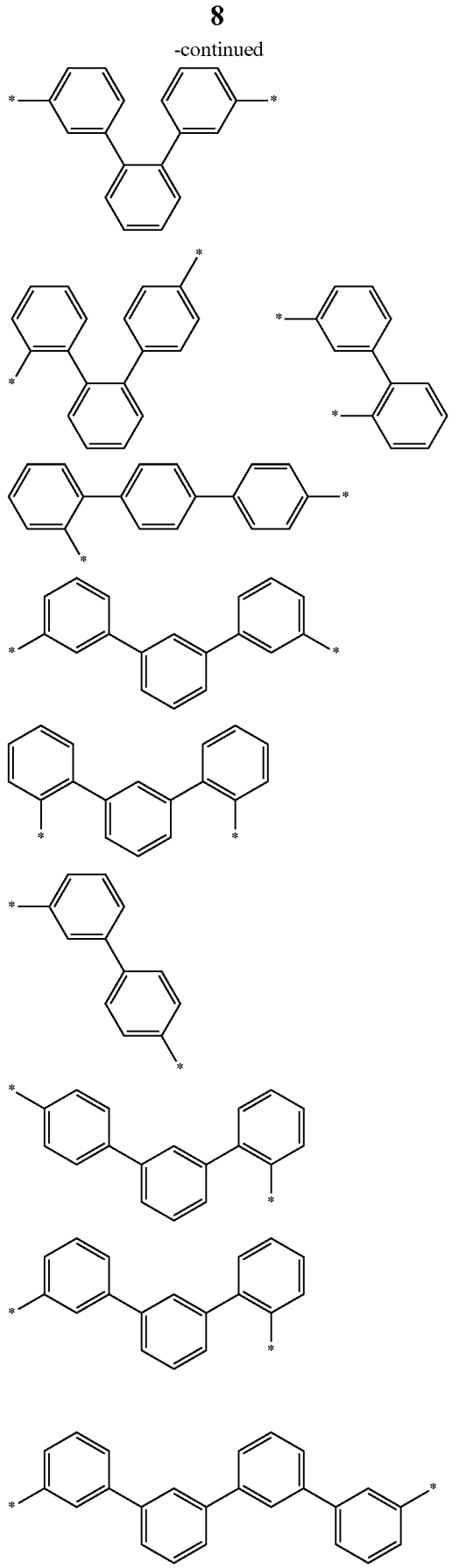

-continued

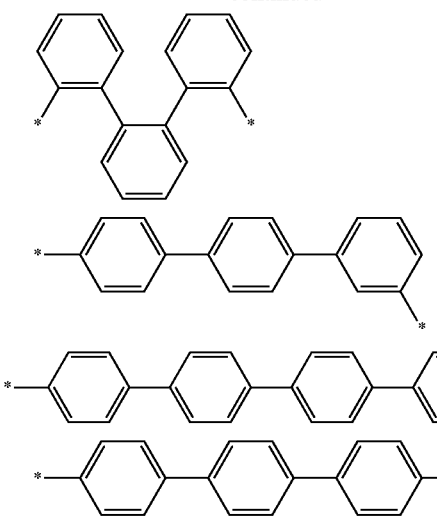

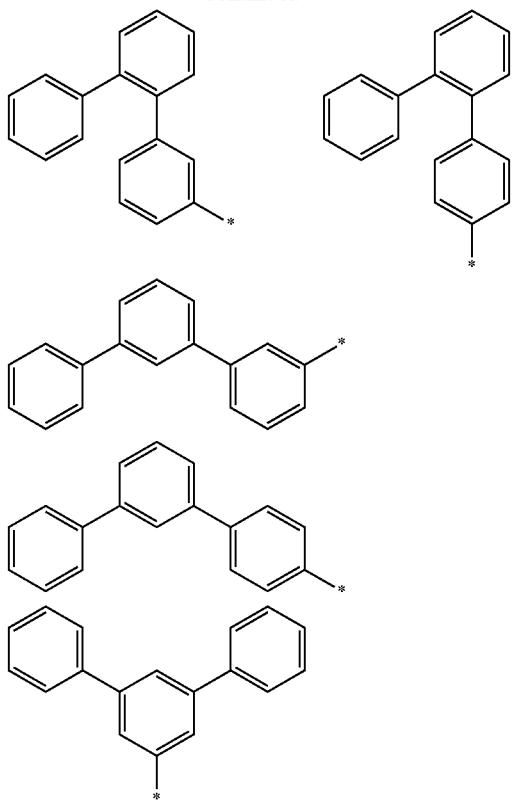

In Group I, * is a linking point with an adjacent atom.

The most specific examples of the $L^1$ may be a single bond, a meta-phenylene group, or a para-phenylene group.

In an example embodiment, the $R^1$ and $R^6$ to $R^{11}$ may independently be hydrogen, deuterium, a substituted or unsubstituted C1 to C4 alkyl group, a substituted or unsubstituted C6 to C12 aryl group, for example hydrogen, a methyl group, a phenyl group, or a biphenyl group, and as the most specific examples, they may be all hydrogen.

In an example embodiment, the $Ar^1$ and $Ar^3$ may independently be a substituted or unsubstituted C6 to C20 aryl group, and specifically a phenyl group, a meta-biphenyl group, a para-biphenyl group, a terphenyl group, a naphthyl group, or a triphenylene group, and may be for example selected from substituents of Group II.

[Group II]

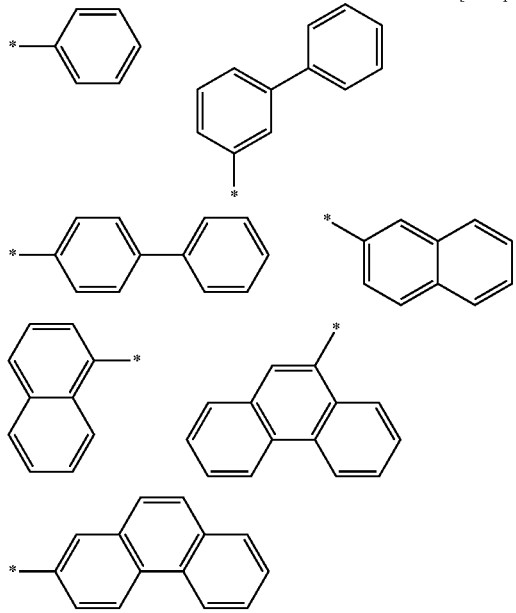

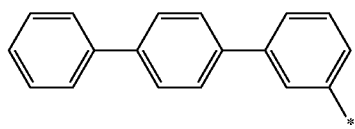

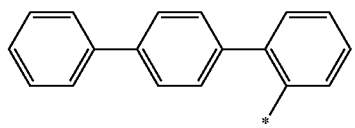

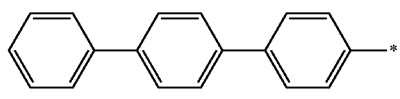

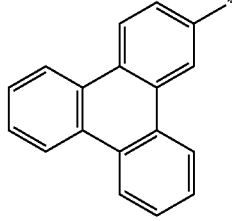 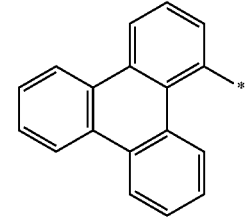

In Group II, * is a linking point with an adjacent atom.

On the other hand, Chemical Formula 1-I may be for example represented by one of Chemical Formulae 1-Ia, 1-Ib, 1-Ic, and 1-Id according to specific linking points, and

[Chemical Formula 1-Ia]
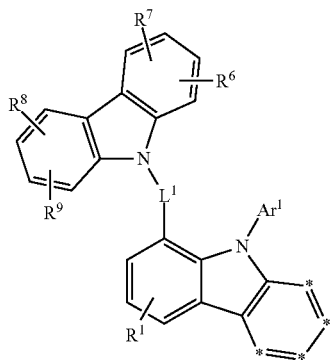
[Chemical Formula 1-Ib]
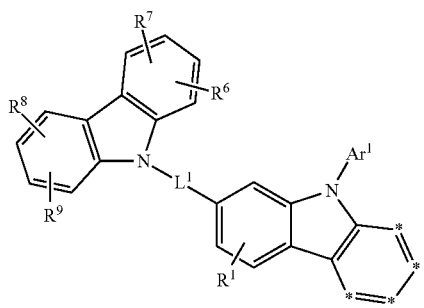
[Chemical Formua 1-Ic]
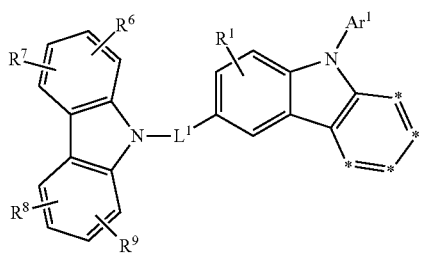
[Chemical Formula 1-Id]
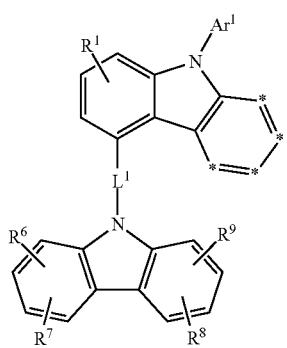
[Chemical Formula 1-II-a1]
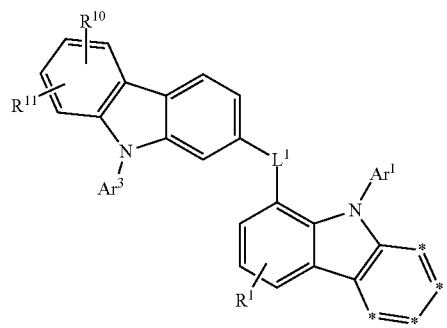
[Chemical Formula 1-II-a2]
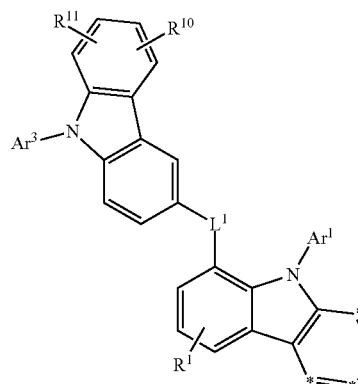
[Chemical Formula 1-II-b1]
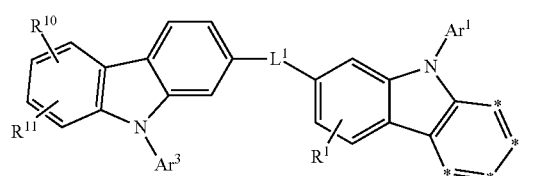
[Chemical Formula 1-II-b2]
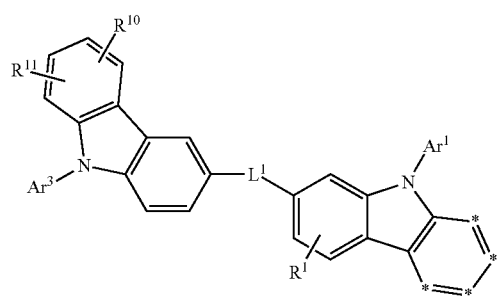
[Chemical Formula 1-II-c1]
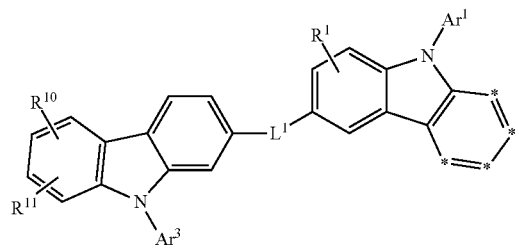
Chemical Formula 1-II may be for example represented by one of Chemical Formulae 1-II-a1, 1-II-a2, 1-II-b1, 1-II-b2, 1-II-c1, 1-II-c2, 1-IId1, and 1-IId2 according to specific linking points.

[Chemical Formula 1-II-c2]

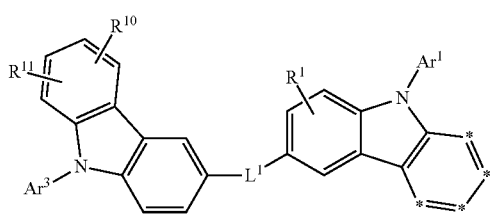

[Chemical Formula 1-II-d1]

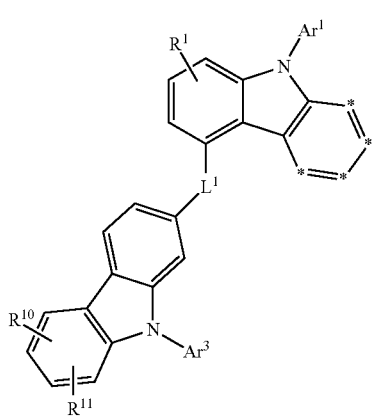

[Chemical Formula 1-II-d2]

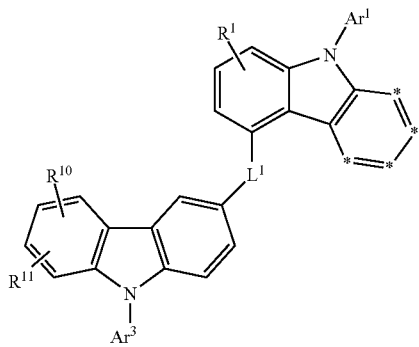

In Chemical Formulae 1-Ia, 1-Ib, 1-Ic, 1-Id, 1-II-a1, 1-II-a2, 1-II-b1, 1-II-b2, 1-II-c1, 1-II-c2, 1-II-d1, and 1-II-d2, "*", $L^1$, $Ar^1$, $Ar^3$, $R^1$, and $R^6$ to $R^{11}$ are the same as described above.

In a specific example embodiment, Chemical Formula 1 may be represented by Chemical Formula 1-Ib, Chemical Formula 1-Ic, Chemical Formula 1-II-c1, or Chemical Formula 1-II-c2.

The first host compound may be for example represented by one of Chemical Formula A, Chemical Formula B, Chemical Formula C, Chemical Formula D, Chemical Formula E, and Chemical Formula F according to fusion points of Chemical Formula 1 and Chemical Formula 2.

[Chemical Formula A]

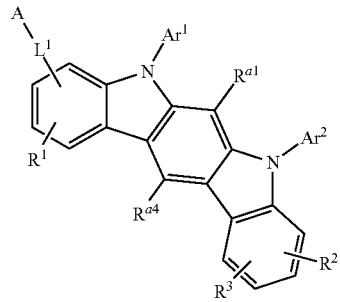

[Chemical Formula B]

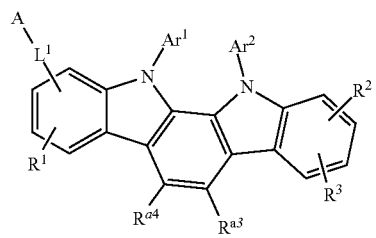

[Chemical Formula C]

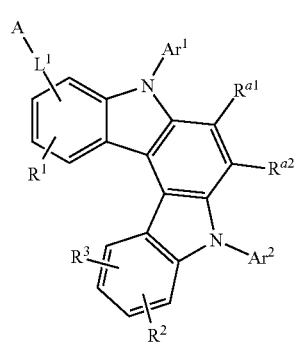

[Chemical Formula D]

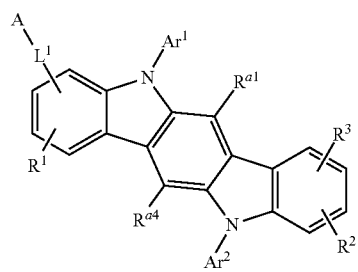

[Chemical Formula E]

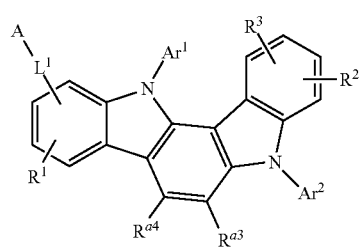

-continued

[Chemical Formula F]

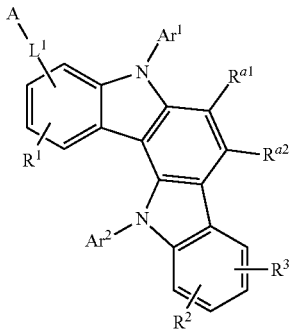

In Chemical Formula A to Chemical Formula F, the substituent A, $L^1$, $Ar^1$, $Ar^2$, and $R^1$ to $R^3$ are the same as above, and in an example embodiment, the $R^{a1}$ to $R^{a4}$ are independently hydrogen, deuterium, a substituted or unsubstituted C1 to C4 alkyl group, a substituted or unsubstituted phenyl group, a substituted or unsubstituted biphenyl group, a substituted or unsubstituted naphthyl group, or a combination thereof. In addition, in a specific example embodiment, $R^{a1}$ to $R^{a4}$ may independently be hydrogen, deuterium, a substituted or unsubstituted phenyl group, or a combination thereof, and for example $R^{a1}$ to $R^{a4}$ may be all hydrogen.

In an example embodiment, the first host compound may be for example represented by one of Chemical Formula C, Chemical Formula E, and Chemical Formula F, and in a more specific example embodiment, it may be represented by one of Chemical Formula C1 to Chemical Formula C6, Chemical Formula E1 to Chemical Formula E6, and Chemical Formula F1 to Chemical Formula F6.

[Chemical Formula C1]

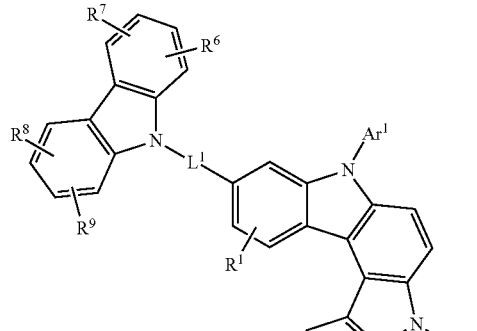

[Chemical Formula C2]

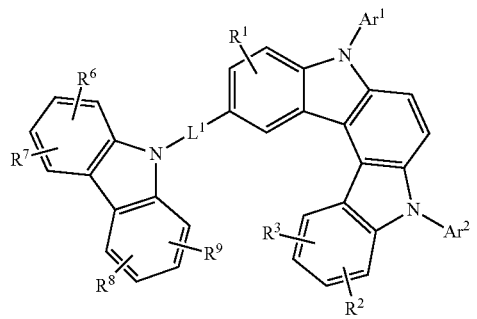

[Chemical Formula C3]

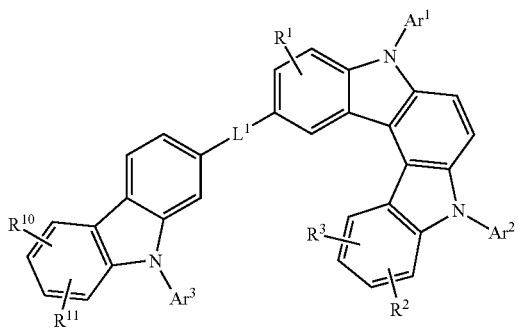

[Chemical Formula C4]

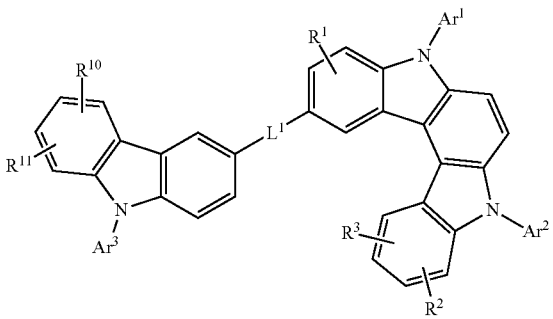

[Chemical Formula C5]

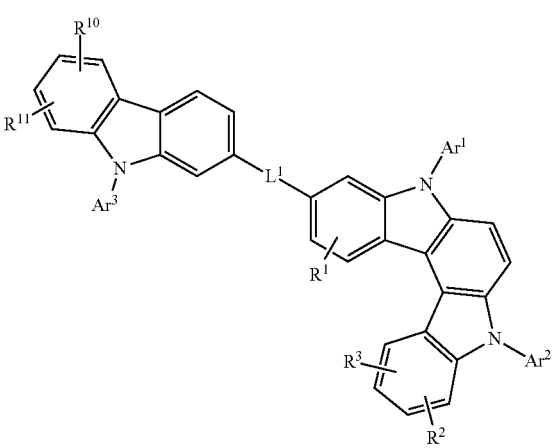

[Chemical Formula C6]

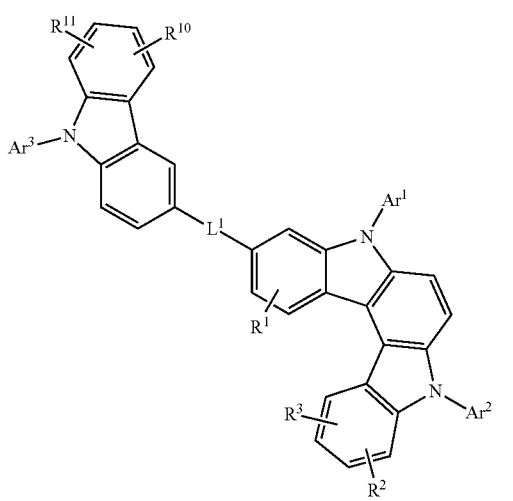

[Chemical Formula E1]
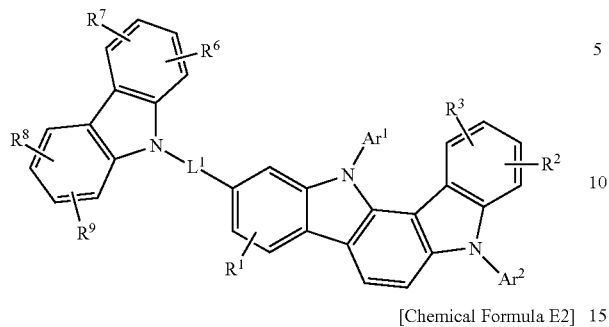
[Chemical Formula E2]
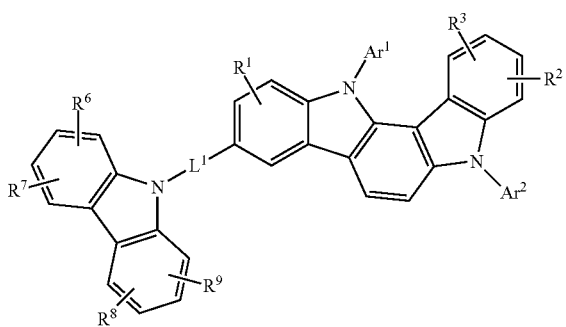
[Chemical Formula E3]
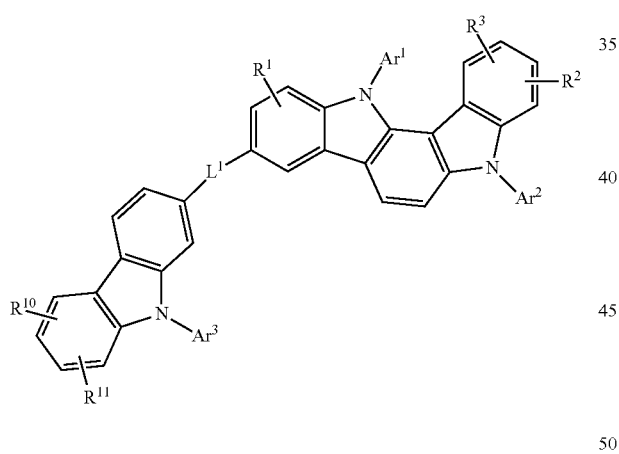
[Chemical Formula E4]
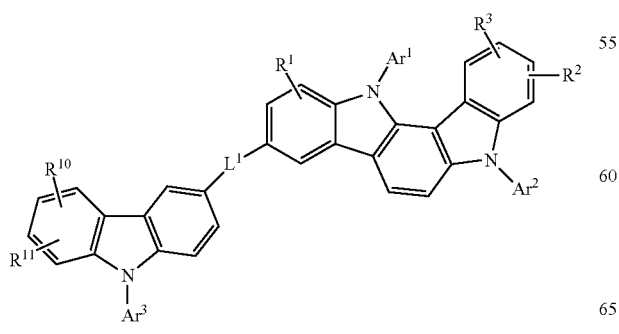
[Chemical Formula E5]
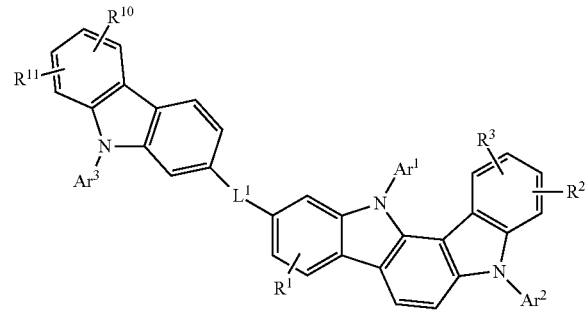
[Chemical Formula E6]
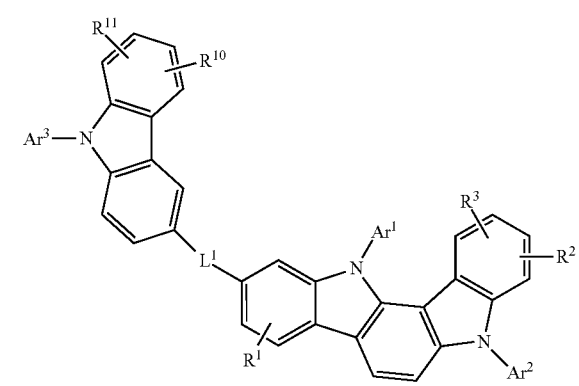
[Chemical Formula F1]
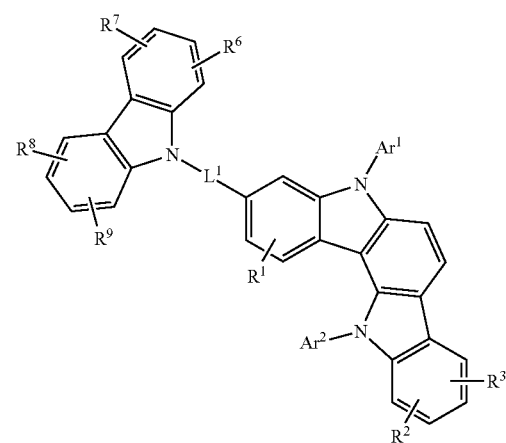
[Chemical Formula F2]
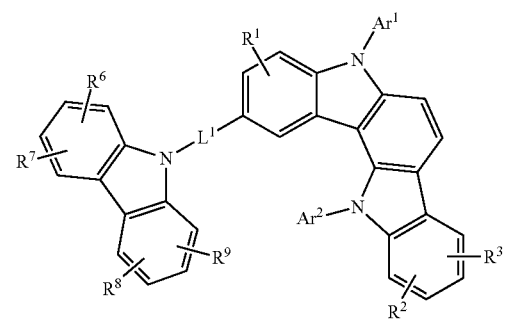

[Chemical Formula F3]

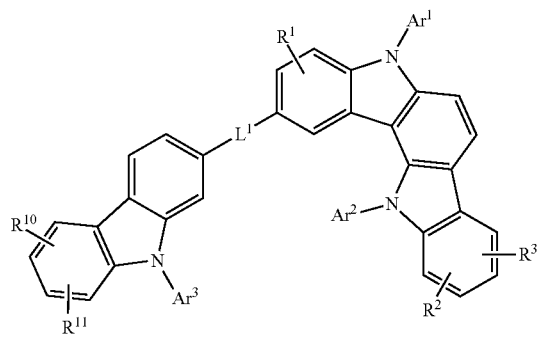

[Chemical Formula F4]

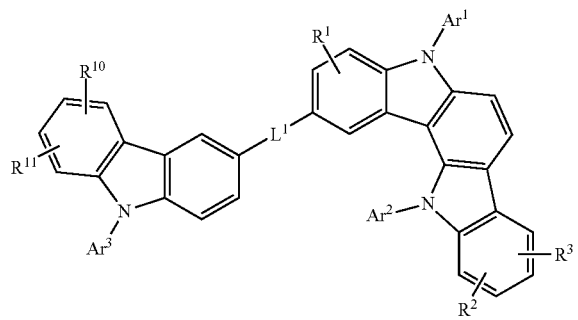

[Chemical Formula F5]

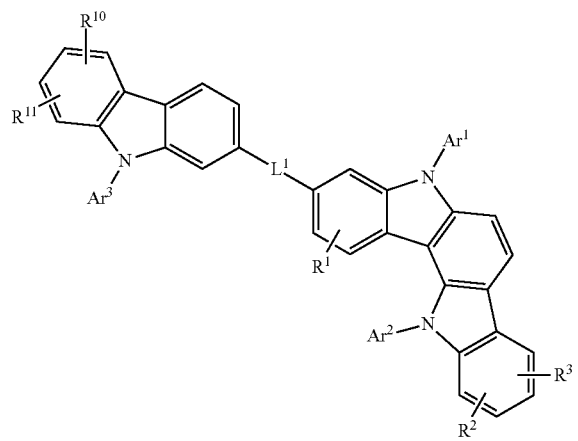

[Chemical Formula F6]

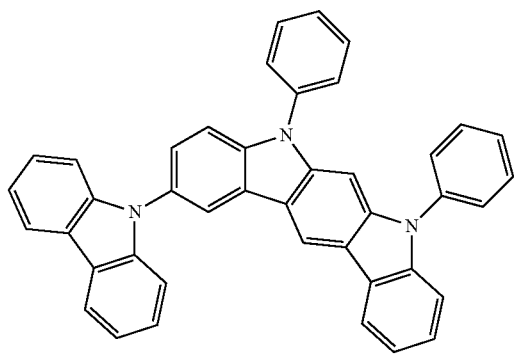

In Chemical Formula C1 to Chemical Formula C6, Chemical Formula E1 to Chemical Formula E6, and Chemical Formula F1 to Chemical Formula F6, $Ar^1$ to $Ar^3$ are independently a substituted or unsubstituted phenyl group, a substituted or unsubstituted biphenyl group, a substituted or unsubstituted terphenyl group, a substituted or unsubstituted naphthyl group, or a substituted or unsubstituted triphenylene group, $L^1$ is a single bond, a substituted or unsubstituted phenylene group, or a substituted or unsubstituted biphenylene group, $R^1$ to $R^3$ and $R^6$ to $R^{11}$ are independently hydrogen, deuterium, a substituted or unsubstituted C1 to C4 alkyl group, a substituted or unsubstituted phenyl group, or a combination thereof, and the "substituted" refers to replacement of at least one hydrogen by deuterium, a C1 to C4 alkyl group, and a C6 to C12 aryl group.

In the most specific example embodiment, the first host compound may be for example represented by one of Chemical Formula C2 to Chemical Formula C4, Chemical Formula E1 to Chemical Formula E4, and Chemical Formula F1.

The first host compound may be compounds of Group 1, but is not limited thereto.

[Group 1]

A-01

-continued
A-02
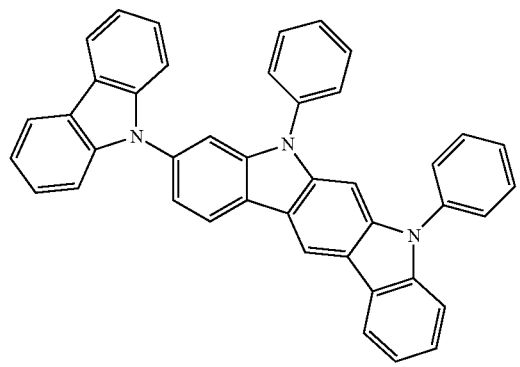
A-03
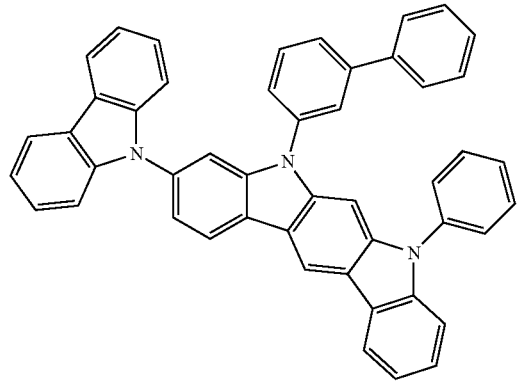
A-04
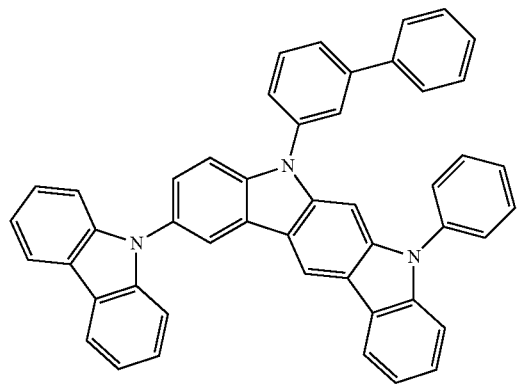
A-05
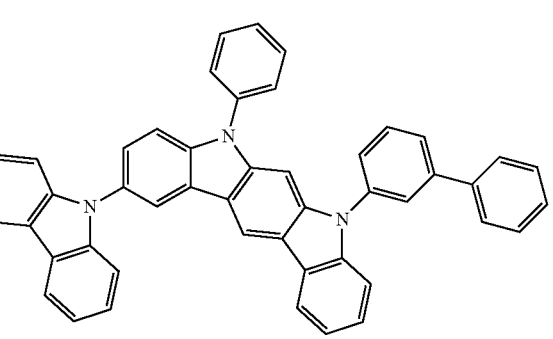
-continued
A-06
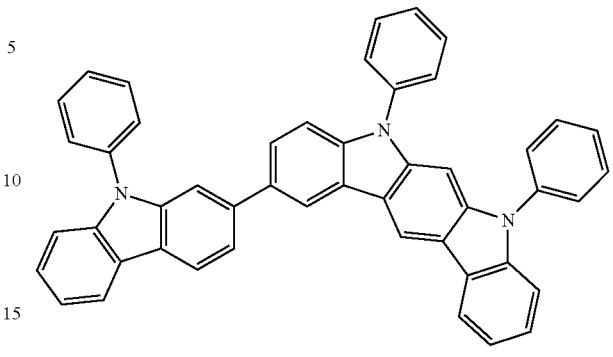
A-07
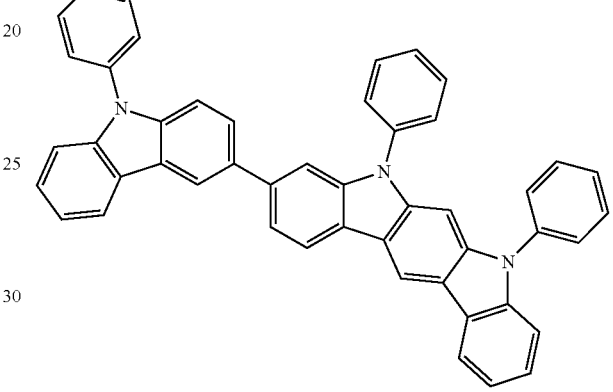
A-08
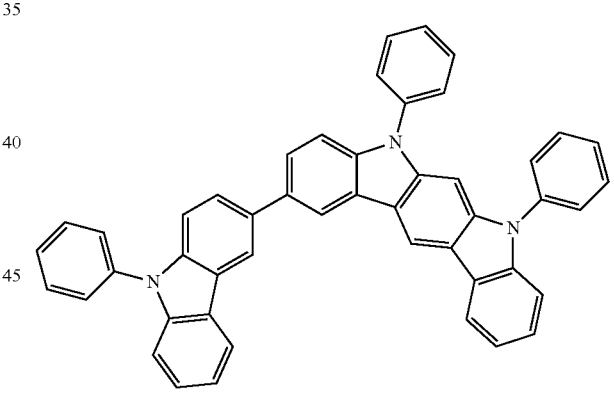
A-09
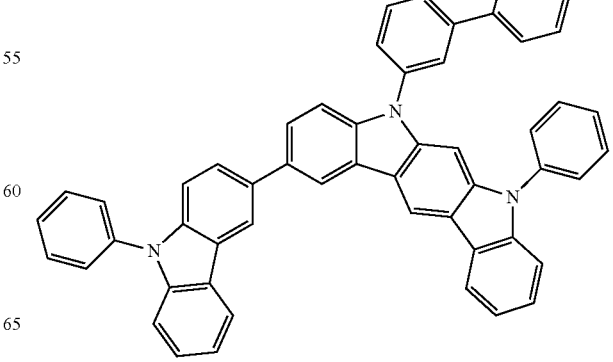

A-10
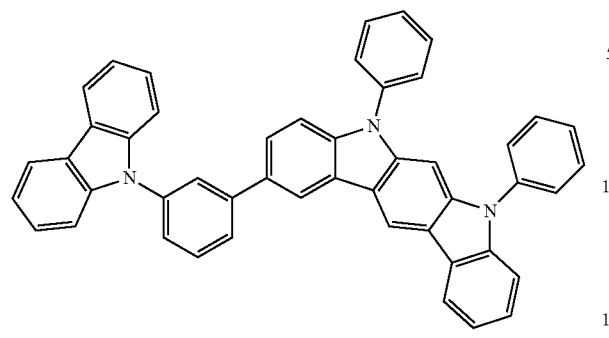
A-11
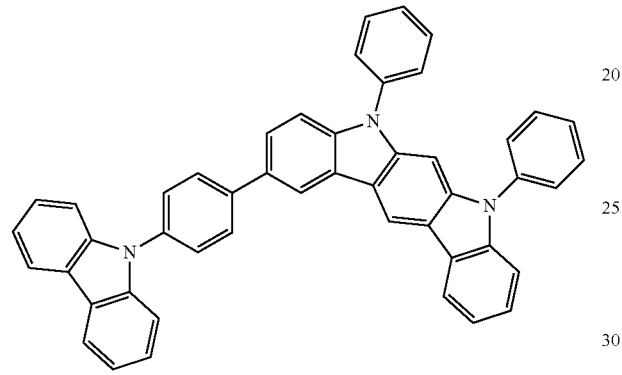
A-12
A-13
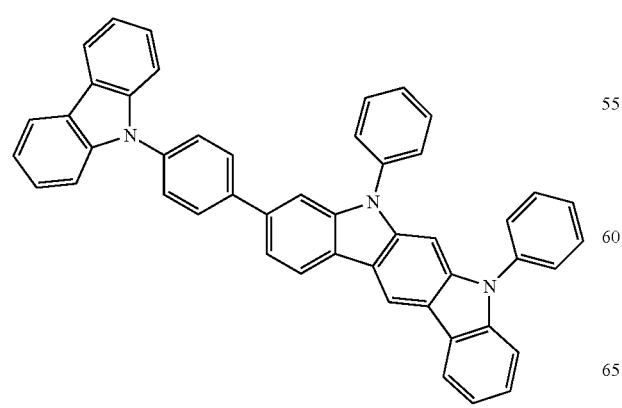
A-14
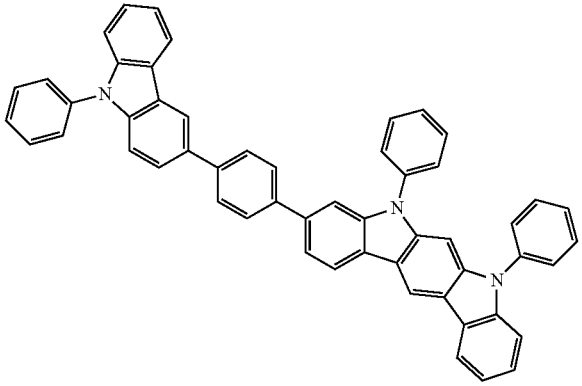
A-15
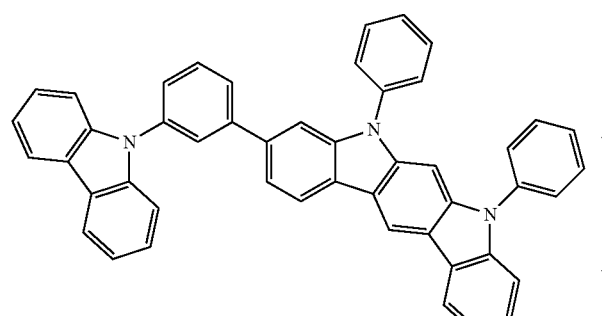
B-01
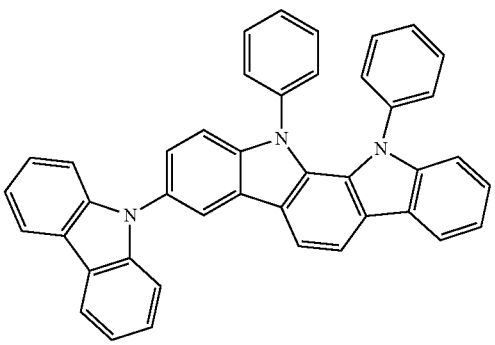
B-02
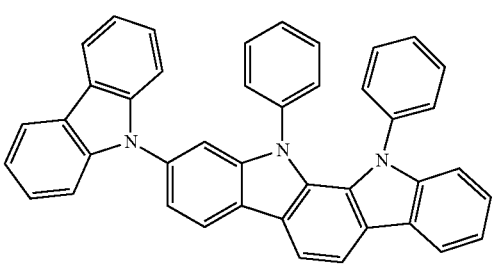

B-03
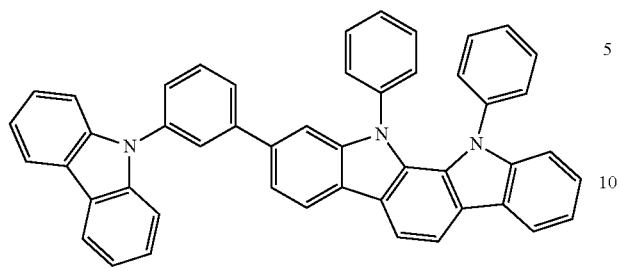
B-04
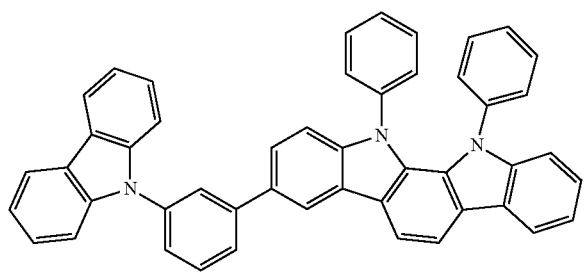
B-05
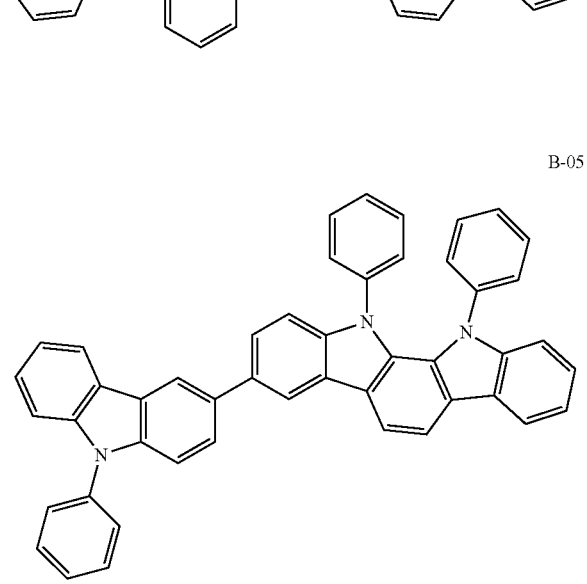
B-06
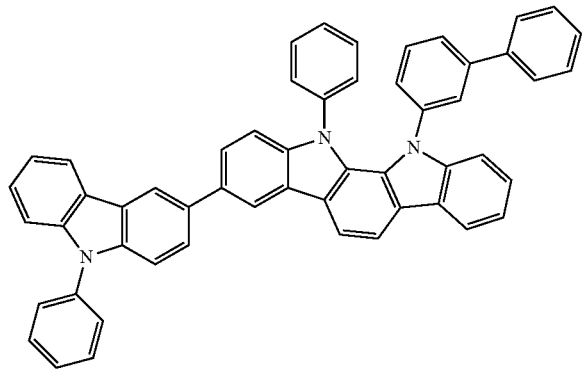
B-07
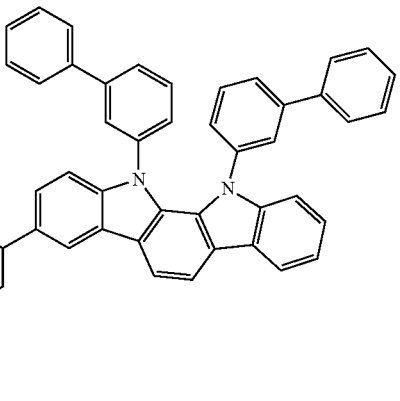
B-08
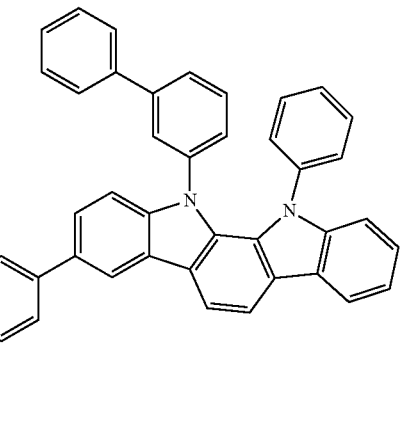
B-09
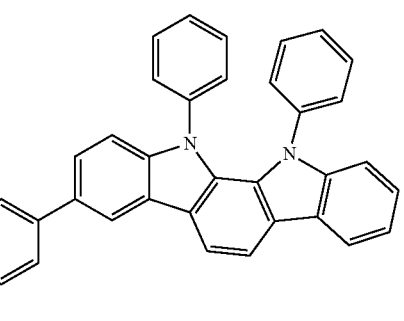
B-10
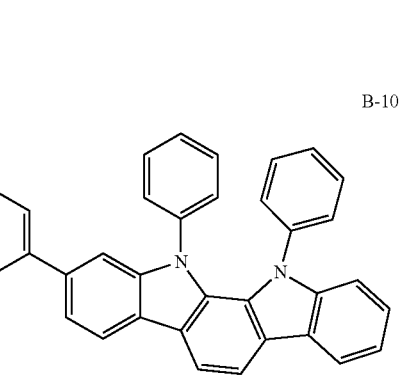

B-11
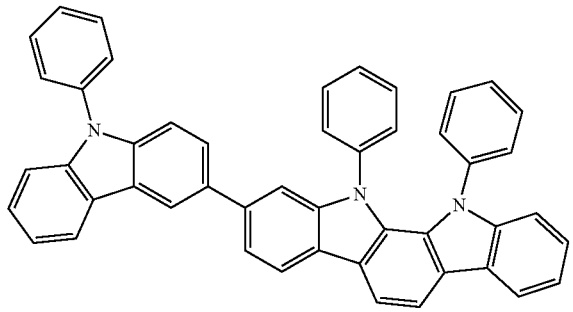
B-12
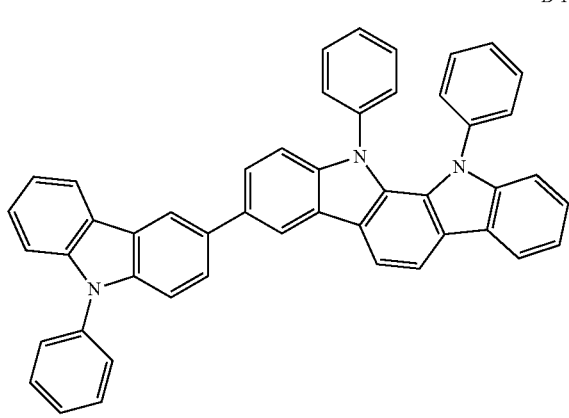
B-13
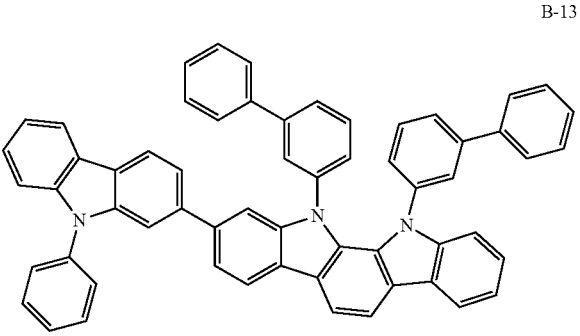
B-14
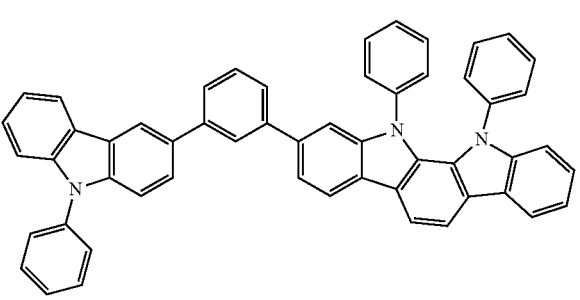
B-15
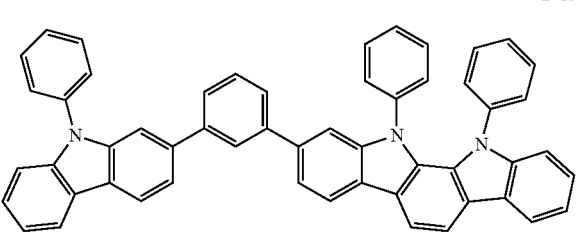
C-01
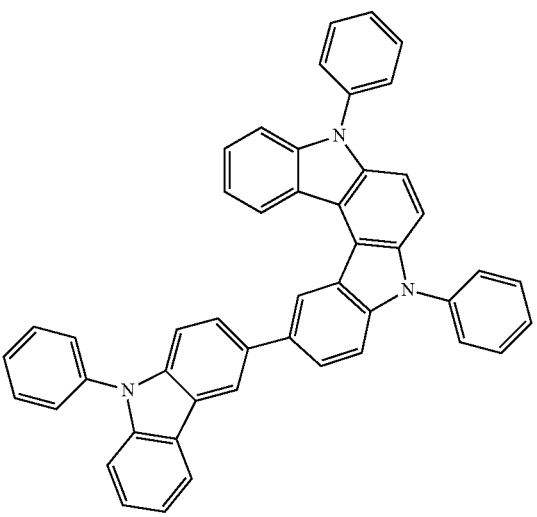
C-02
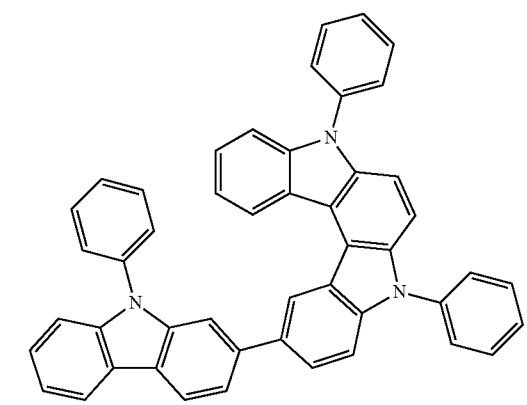
C-03
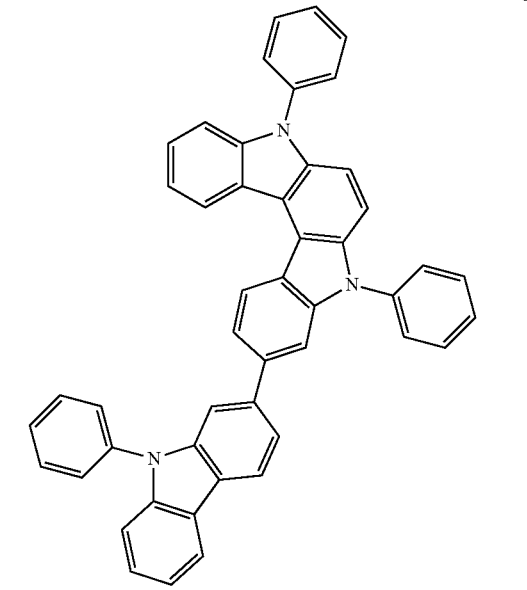

C-04
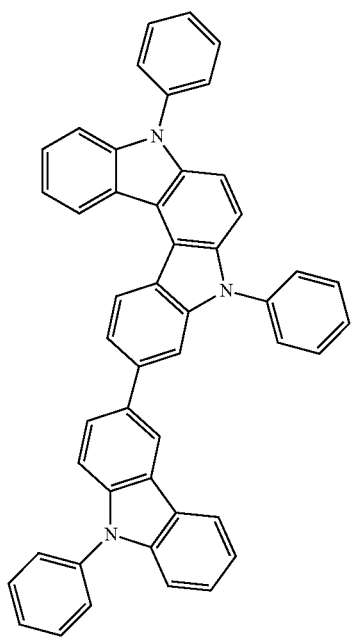
C-05
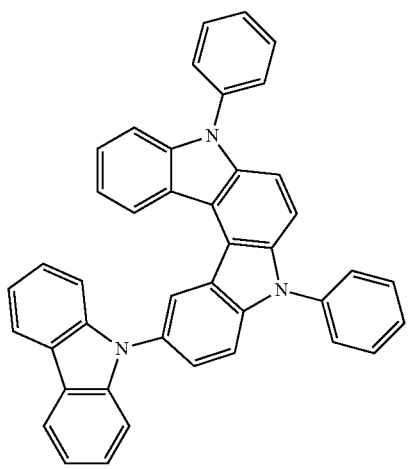
C-06
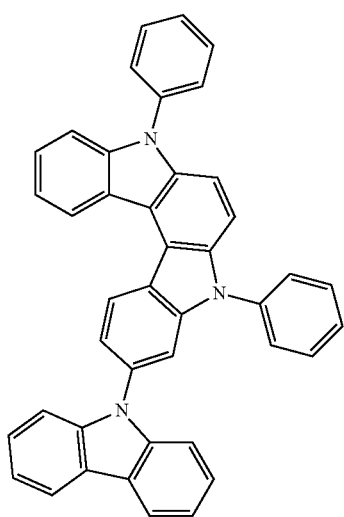
C-07
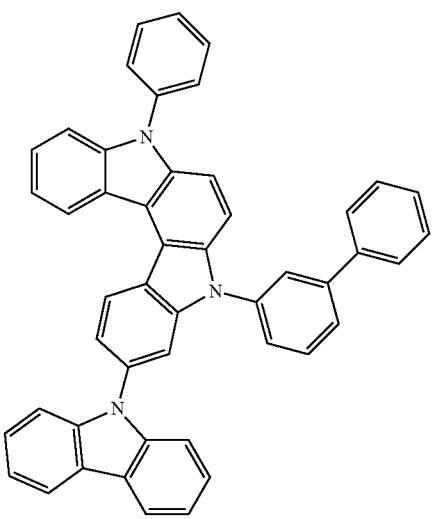
C-08
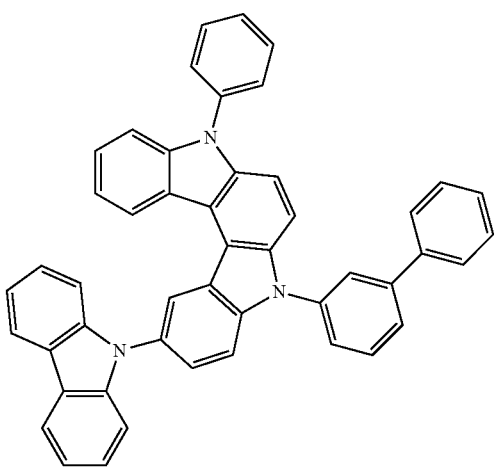
C-09
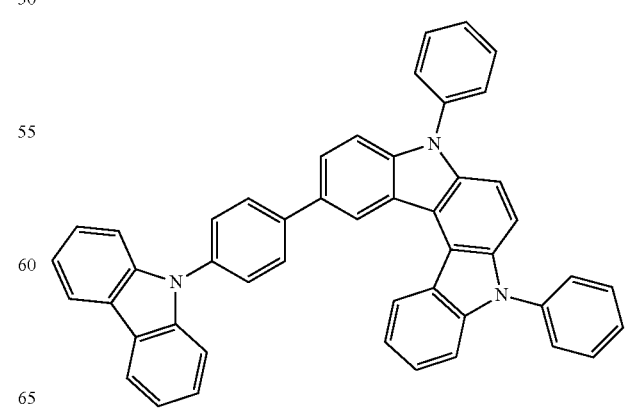

C-10
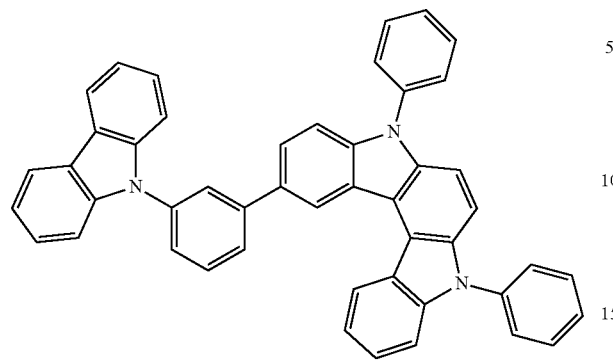
C-13
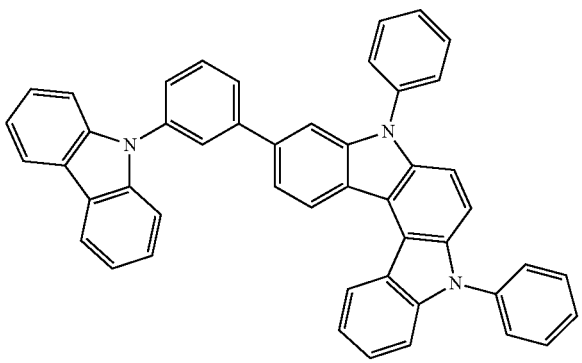
C-11
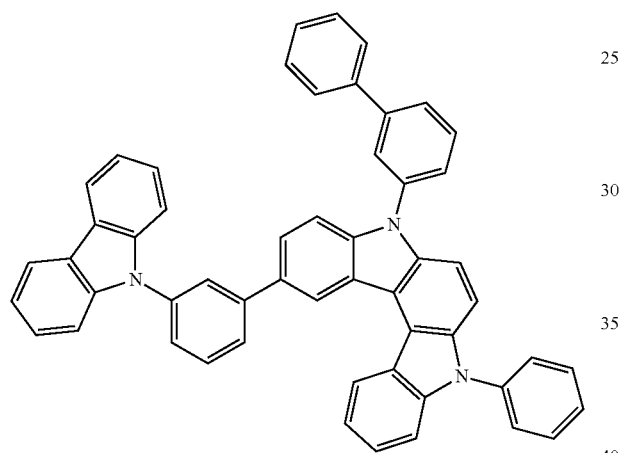
C-14
C-12
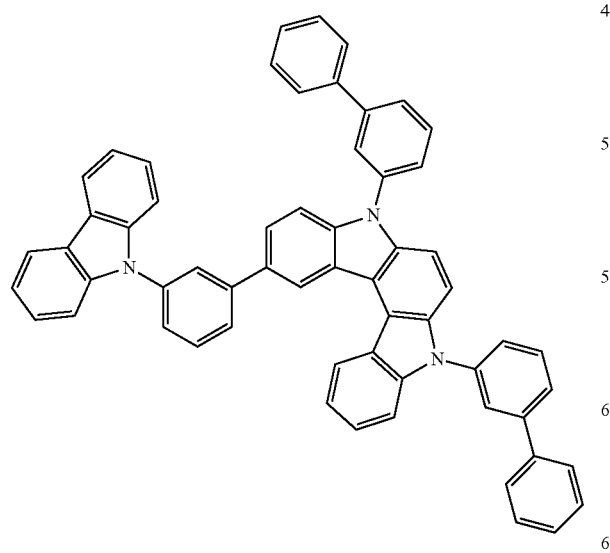
C-15
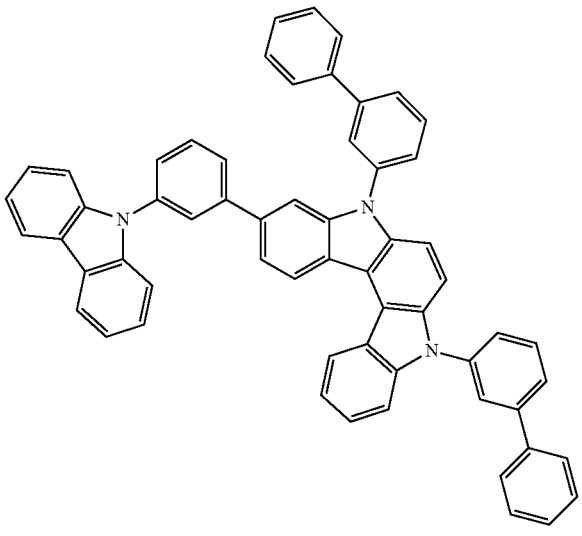

D-01
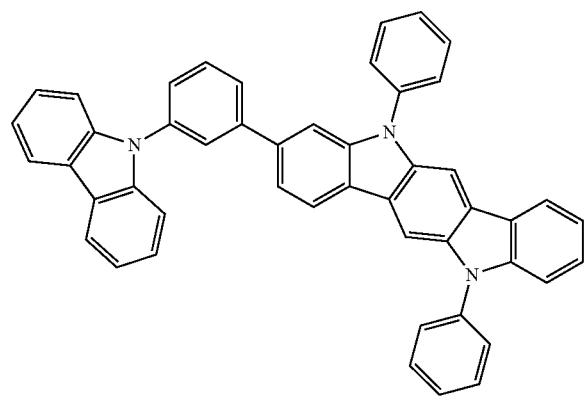
D-02
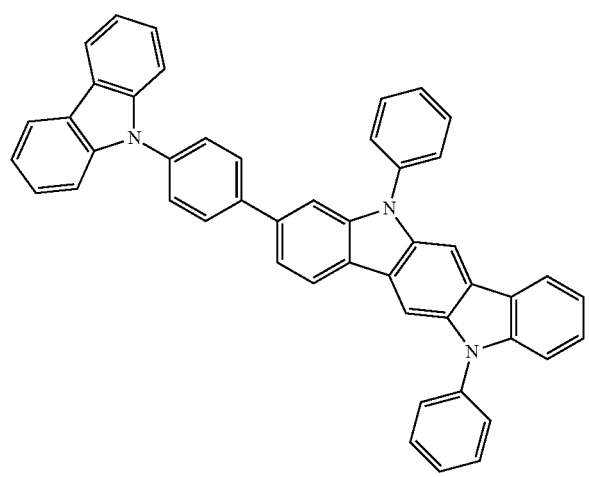
D-03
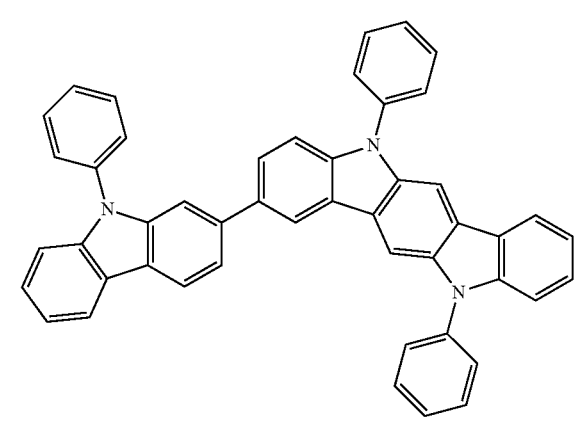
D-04
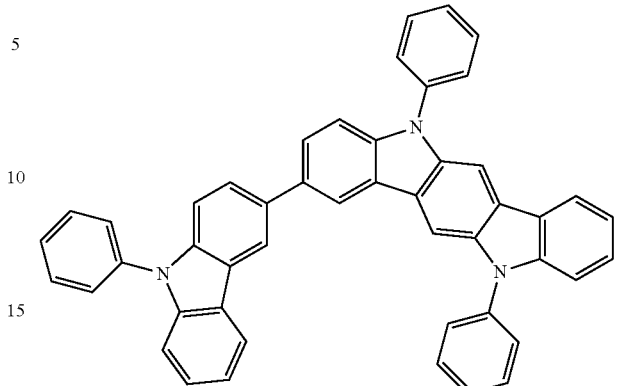
D-05
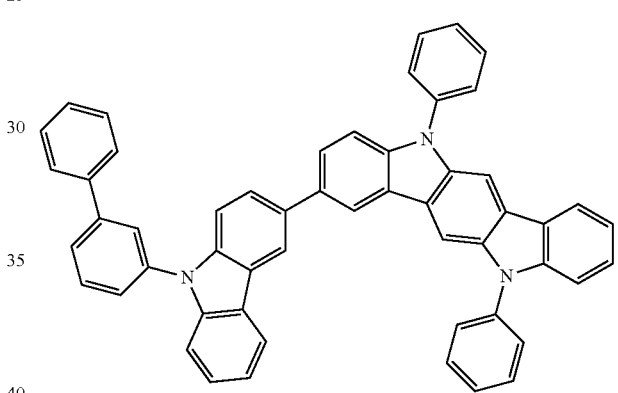
D-06
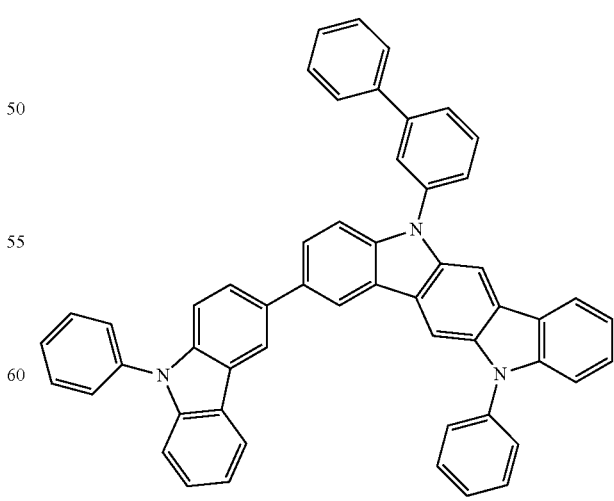

-continued
D-07
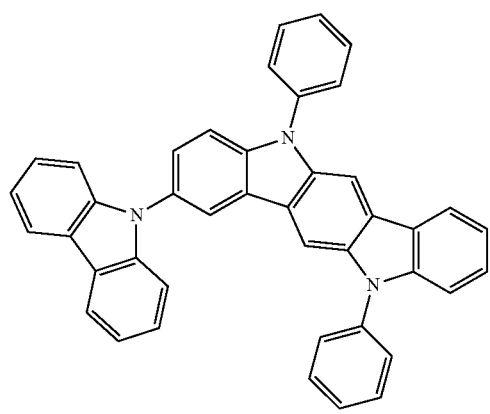
D-08
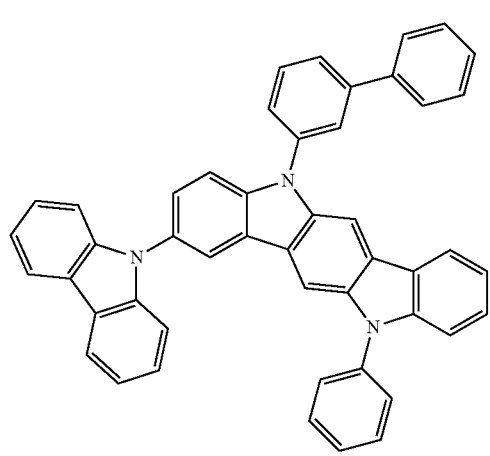
D-09
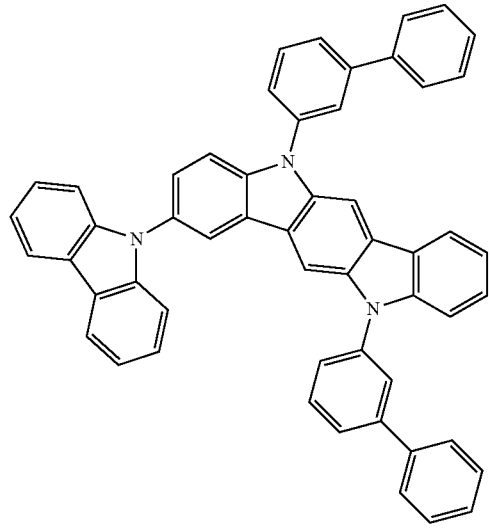
D-10
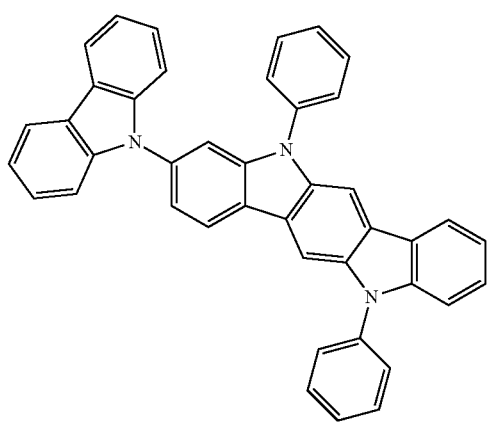
D-11
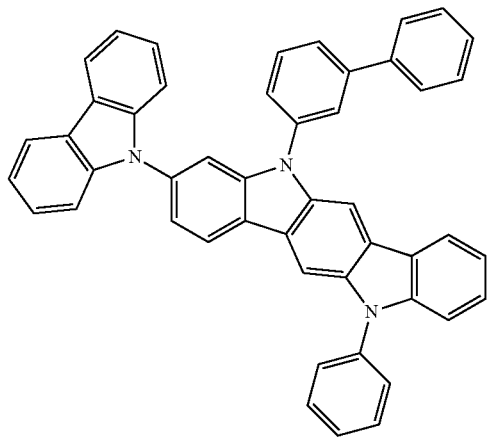
D-12
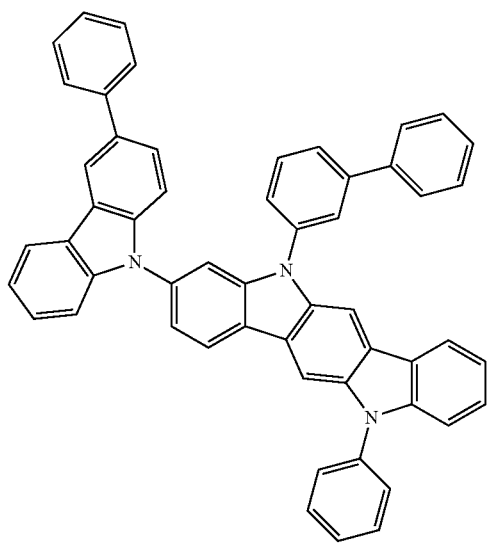

E-01
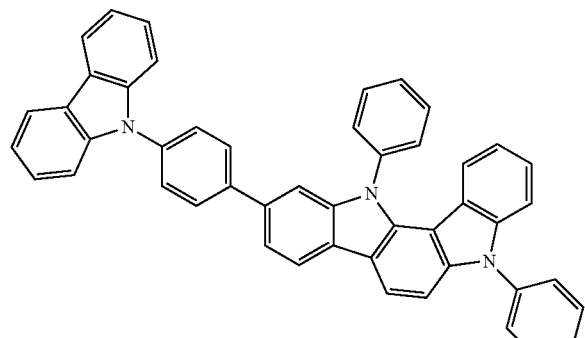
E-02
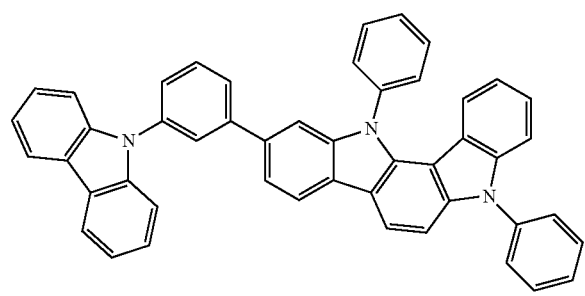
E-03
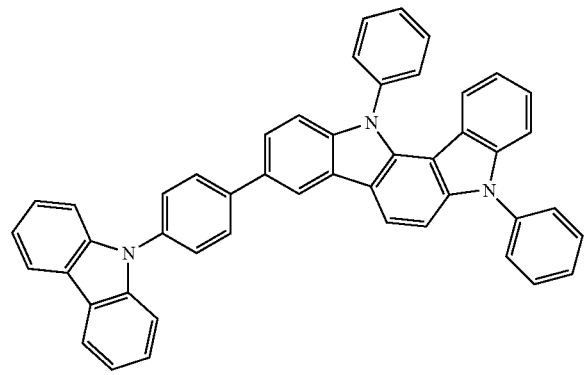
E-04
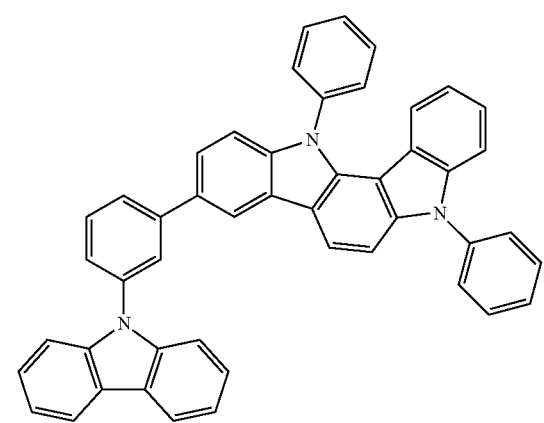
E-05
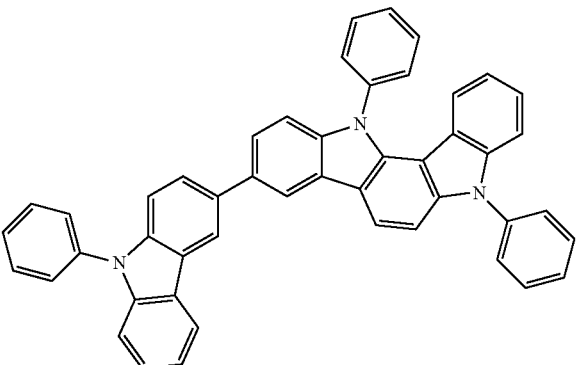
E-06
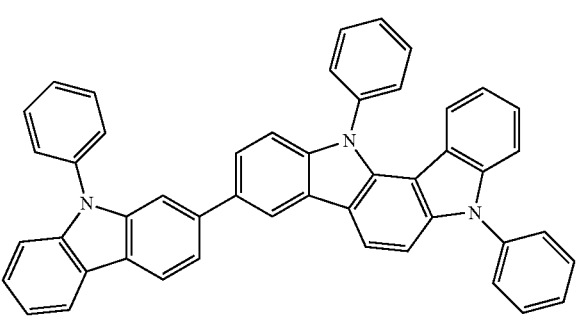
E-07
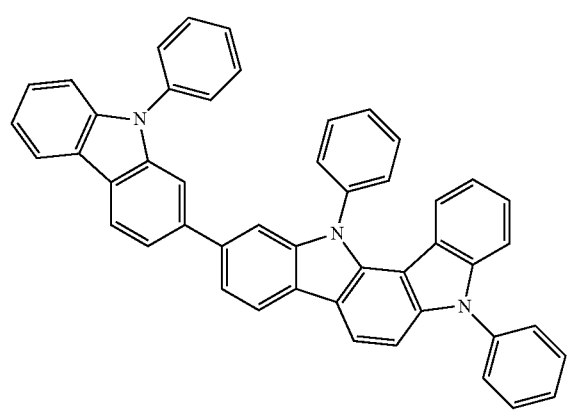
E-08
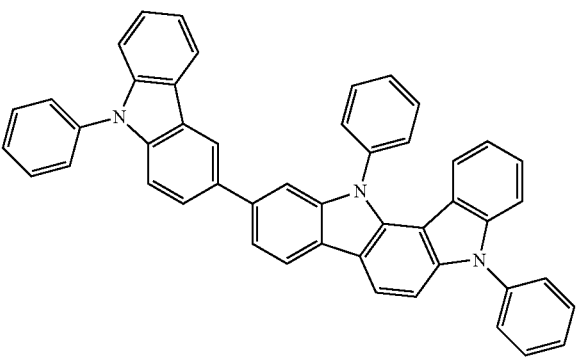

-continued
E-09
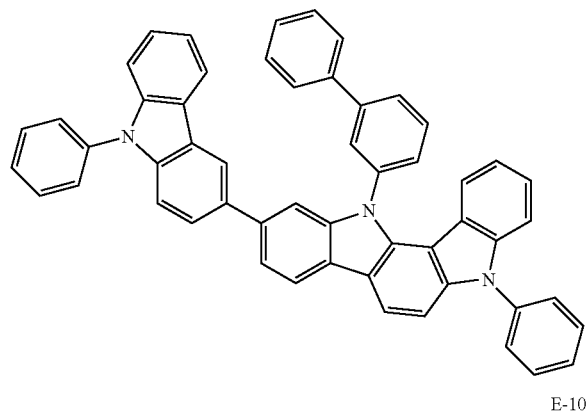
E-10
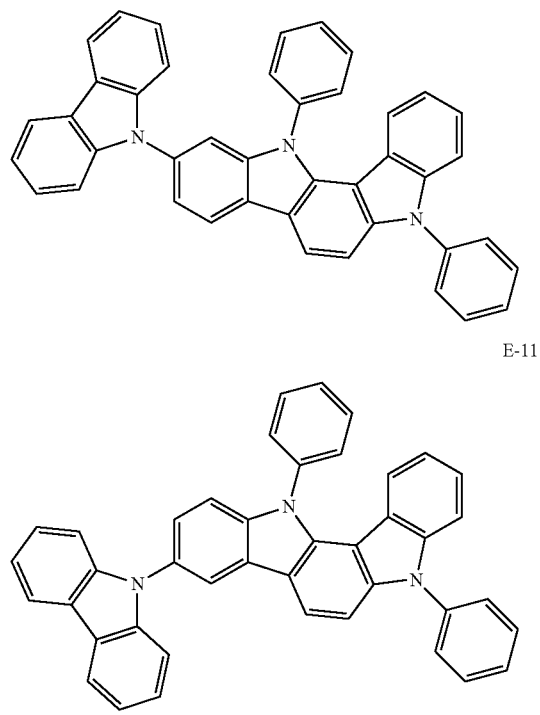
E-11
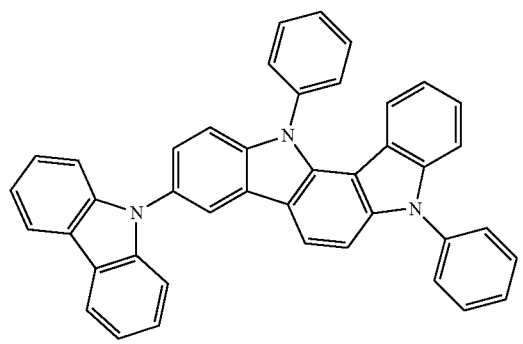
E-12
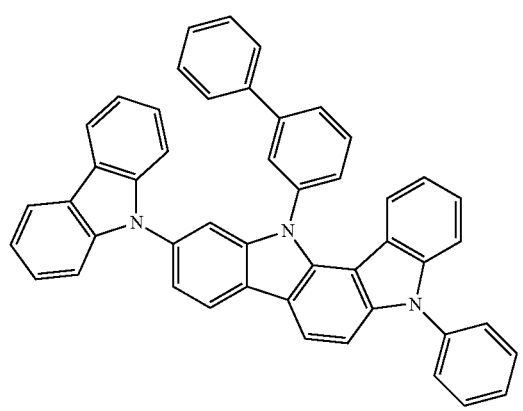
-continued
E-13
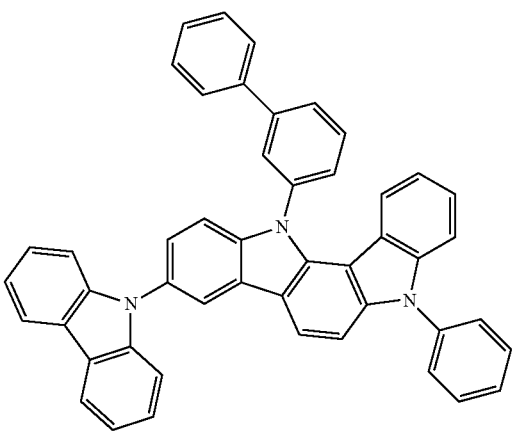
E-14
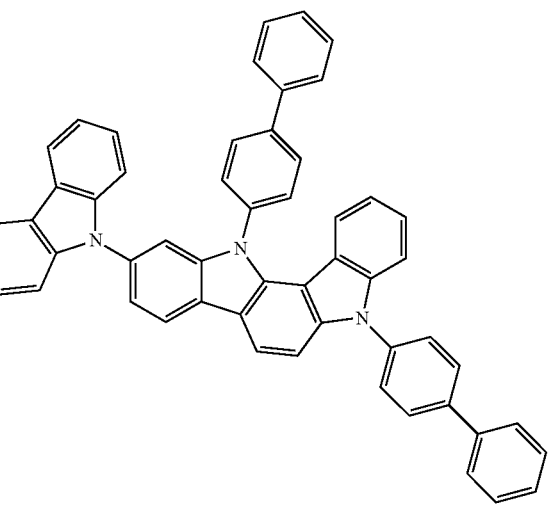
E-15
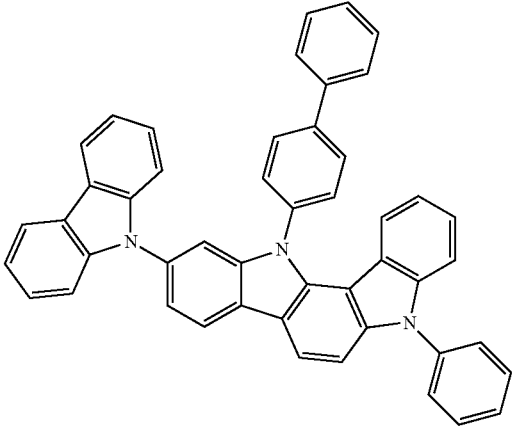

E-16
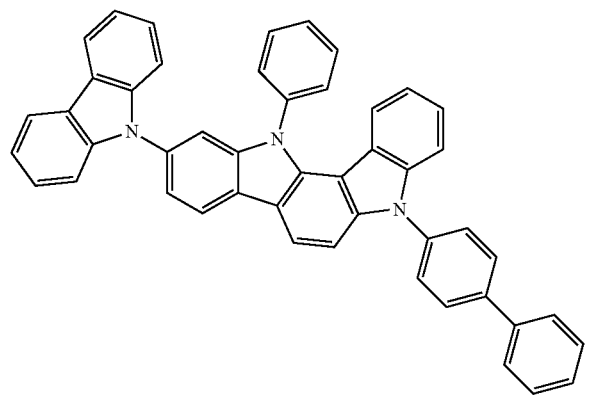
E-19
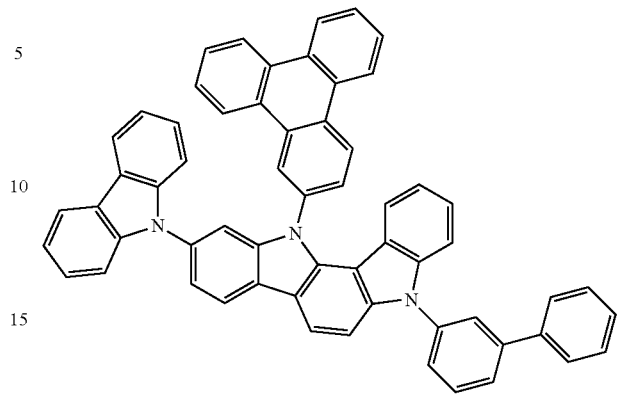
E-17
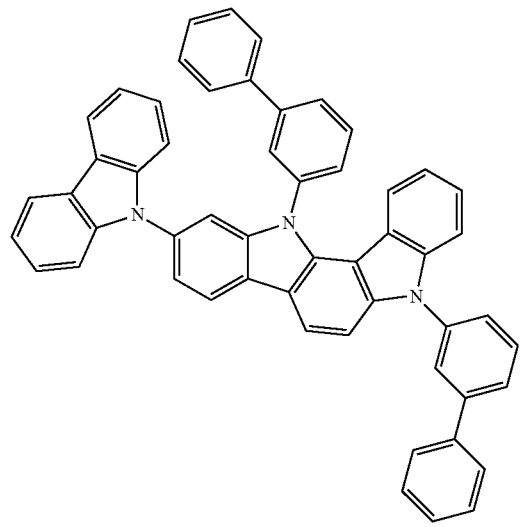
F-1
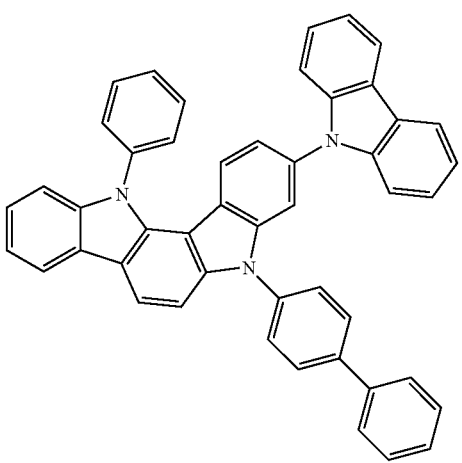
E-18
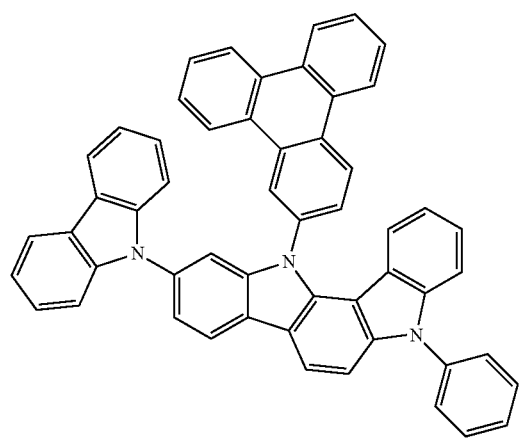
F-2
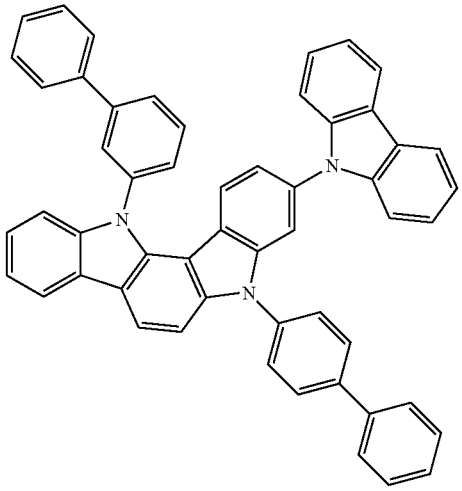
The second host compound is a compound having relatively strong electron transport characteristics and may be represented by a combination of Chemical Formula 3 and Chemical Formula 4.

[Chemical Formula 3]

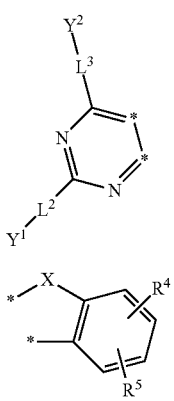

[Chemical Formula 4]

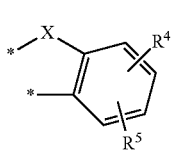

In Chemical Formula 3 and Chemical Formula 4, two adjacent *'s of Chemical Formula 3 are bound to two adjacent *'s of Chemical Formula 4, X is O or S, $L^2$ and $L^3$ are independently a single bond or a substituted or unsubstituted C6 to C30 arylene group, $Y^1$ and $Y^2$ are independently deuterium, a substituted or unsubstituted C1 to C10 alkyl group, a substituted or unsubstituted C6 to C30 aryl group, or a substituted or unsubstituted C2 to C30 heterocyclic group, at least one of $Y^1$ and $Y^2$ is a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group, and $R^4$ and $R^5$ are independently hydrogen, deuterium, a substituted or unsubstituted C1 to C10 alkyl group, a substituted or unsubstituted C6 to C20 aryl group, or a combination thereof.

The second host compound includes a substituent having electron characteristics and including a nitrogen-containing hexagonal ring in addition to a benzofuran pyrimidine or benzothiophene pyrimidine structure, thereby the compound may become a structure capable of accepting electrons when an electric field is applied, and accordingly the compound has fast electron/hole characteristics with the first host compound, and a driving voltage of an organic optoelectronic device may be lowered and high efficiency and life-span characteristics may be realized due to an electron/hole balance by an appropriate ratio combination.

In the present disclosure, "substituted" of Chemical Formulae 3 and 4 refers to replacement of at least one hydrogen by deuterium, a C1 to C4 alkyl group, or a C6 to C12 aryl group. In an example embodiment, the "substituted" refers to replacement by a phenyl group, a biphenyl group, or a terphenyl group.

In an example embodiment, the $L^2$ and $L^3$ may independently be a single bond, or a substituted or unsubstituted C6 to C12 arylene group, and specifically a single bond, a substituted or unsubstituted phenylene group, a substituted or unsubstituted biphenylene group, a substituted or unsubstituted terphenylene group, or a substituted or unsubstituted quaterphenylene group, and may be for example selected from Group I.

In an example embodiment, the $R^4$ and $R^5$ may independently be hydrogen, deuterium, a substituted or unsubstituted C1 to C4 alkyl group, or a substituted or unsubstituted C6 to C12 aryl group, and may be for example hydrogen, a phenyl group, or a biphenyl group.

In an example embodiment, the $Y^1$ and $Y^2$ may independently be a substituted or unsubstituted C6 to C20 aryl group, or a substituted or unsubstituted C2 to C30 heterocyclic group, and at least one of $Y^1$ and $Y^2$ may be a substituent having electron characteristics and including a nitrogen-containing hexagonal ring and may be a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group.

For example, the second host compound may be represented by one of Chemical Formula 3-I, Chemical Formula 3-II, Chemical Formula 3-III, and Chemical Formula 3-IV.

[Chemical Formula 3-I]

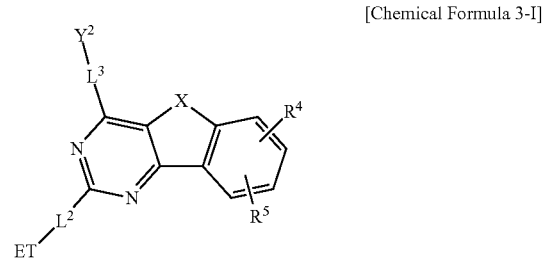

[Chemical Formula 3-II]

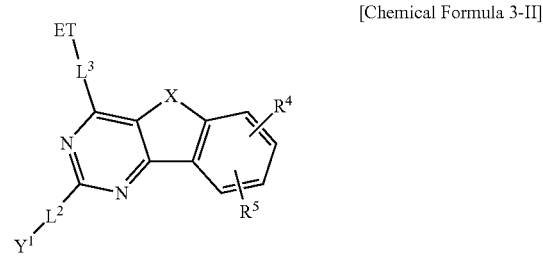

[Chemical Formula 3-III]

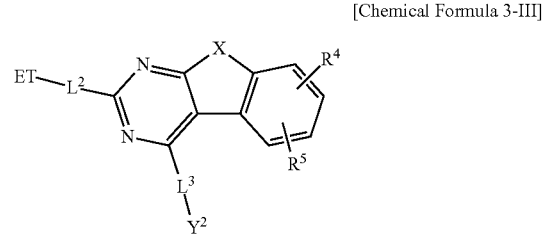

[Chemical Formula 3-IV]

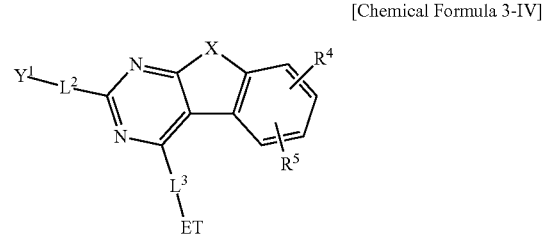

In Chemical Formula 3-I, Chemical Formula 3-II, Chemical Formula 3-III, and Chemical Formula 3-IV, X, $L^2$ and $L^3$ and $R^4$ and $R^5$ are the same as described above, and the $Y^1$ and $Y^2$ may independently be a substituted or unsubstituted C6 to C20 aryl group, and specifically a substituted or unsubstituted phenyl group, a substituted or unsubstituted meta-biphenyl group, a substituted or unsubstituted para-biphenyl group, a substituted or unsubstituted terphenyl group, or a substituted or unsubstituted naphthyl group, and may be for example selected from substituents of Group II.

In addition, the ET is a substituent having electron characteristics and including a nitrogen-containing hexagonal ring and may be a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group, and specifically a substituted or unsubstituted pyridyl group, a substituted or unsubstituted pyrimidinyl group, a substituted or unsubstituted triazinyl group, or a substituted or unsubstituted quinazolyl group.

In a specific example embodiment, the $L^2$ and $L^3$ may independently be a single bond, a substituted or unsubstituted phenylene group, a substituted or unsubstituted biphenylene group, a substituted or unsubstituted terphenylene group, or a substituted or unsubstituted quaterphenylene group, the ET may be a substituted or unsubstituted pyridyl group, a substituted or unsubstituted pyrimidinyl group, a substituted or unsubstituted triazinyl group, or a substituted or unsubstituted quinazolyl group, the $Y^1$ and $Y^2$ may independently be a substituted or unsubstituted phenyl group, a substituted or unsubstituted biphenyl group, or a substituted or unsubstituted terphenyl group, the $R^4$ and $R^5$ may independently be hydrogen, deuterium, a substituted or unsubstituted C1 to C4 alkyl group, a substituted or unsubstituted phenyl group, or a combination thereof, and the "substituted" may refer to replacement of at least one hydrogen by deuterium, a C1 to C4 alkyl group, or a C6 to C12 aryl group.

The second host compound as specific examples may be represented by Chemical Formula 3-I and $L^2$ of Chemical Formula 3-I may be a phenylene group, a biphenylene group, or a terphenylene group.

In addition, $L^3$ of Chemical Formula 3-I may be a single bond and $Y^2$ may be a phenyl group or a biphenyl group.

The ET may be a substituted or unsubstituted pyrimidinyl group, or a substituted or unsubstituted triazinyl group and $R^4$ and $R^5$ are hydrogen.

The second host compound may be for example compounds of Group 2, but is not limited thereto.

[Group 2]

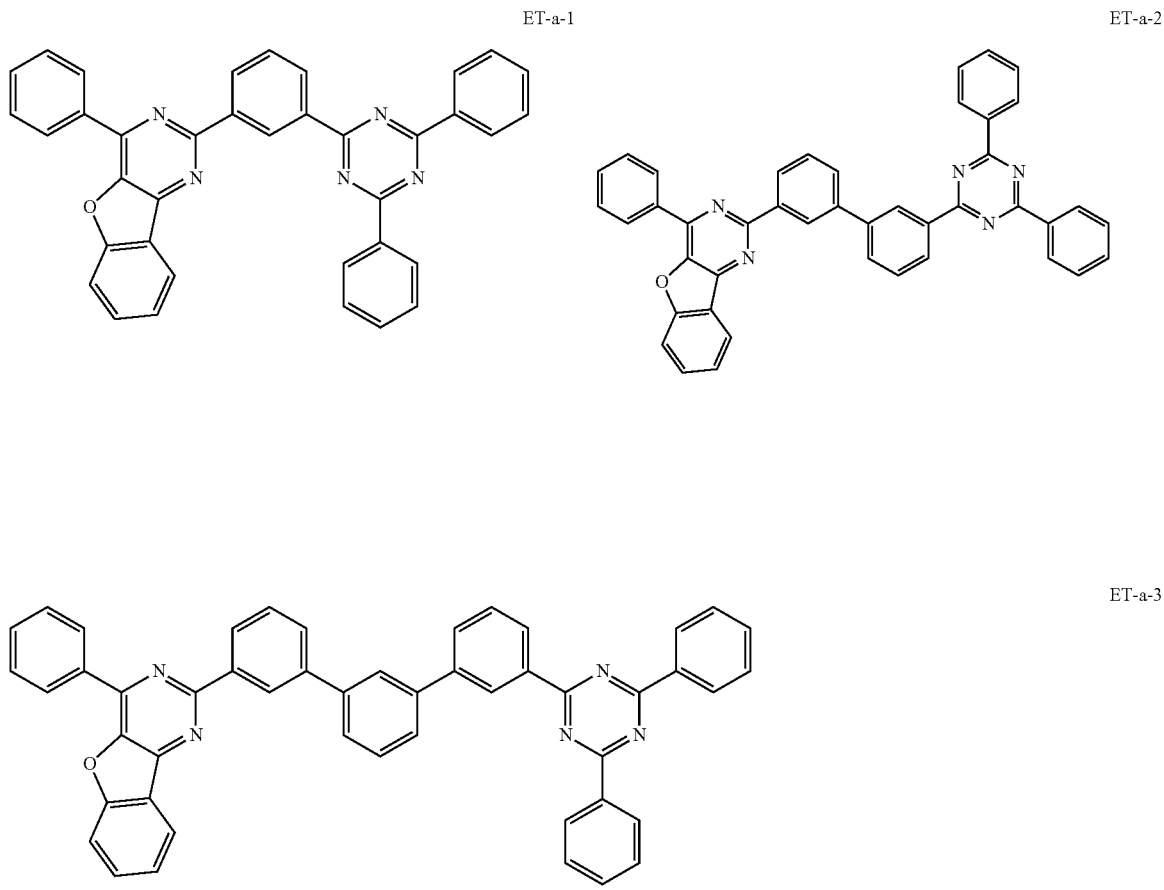

ET-a-4
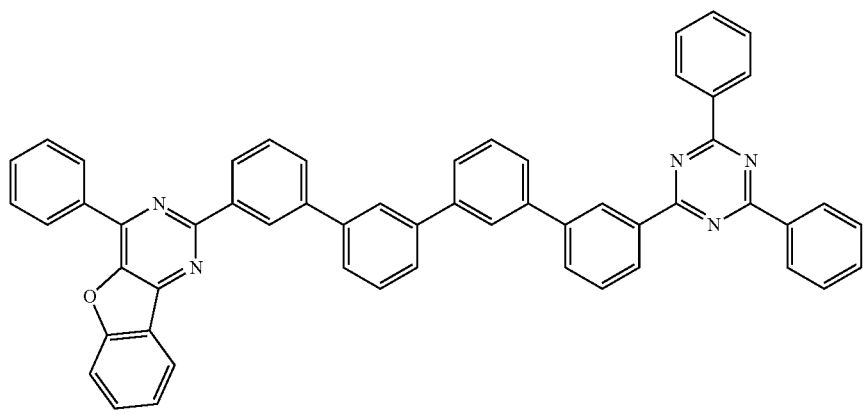
(X = O)
ET-a-5
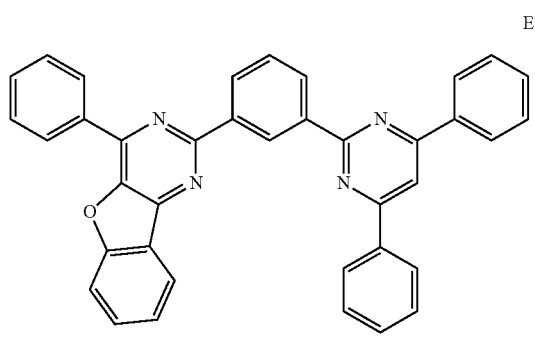
ET-a-6
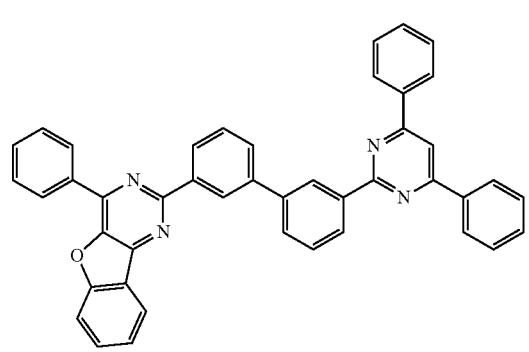
ET-a-7
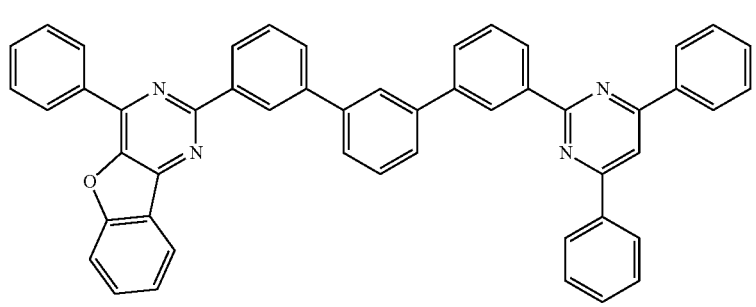
ET-a-8
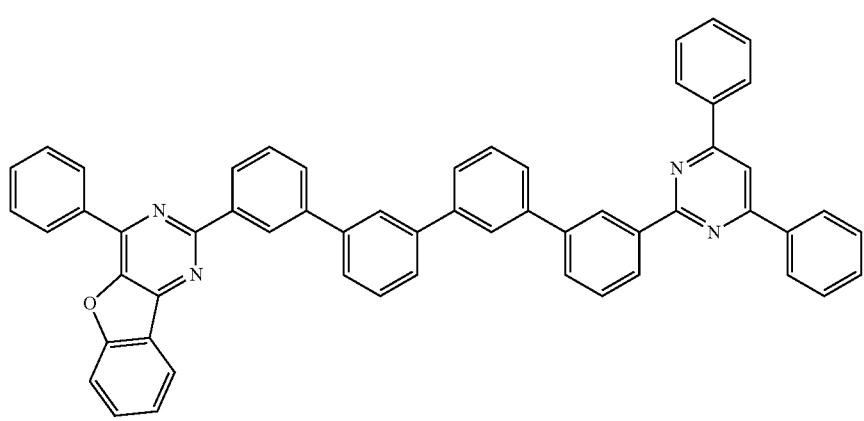

-continued
ET-a-9
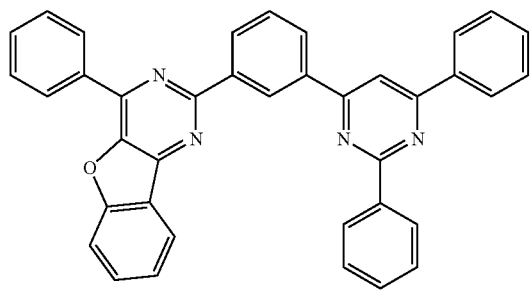
ET-a-10
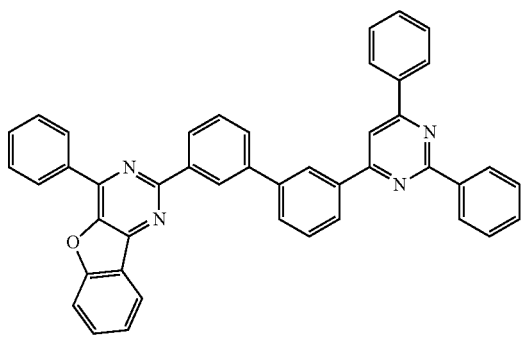
ET-a-11
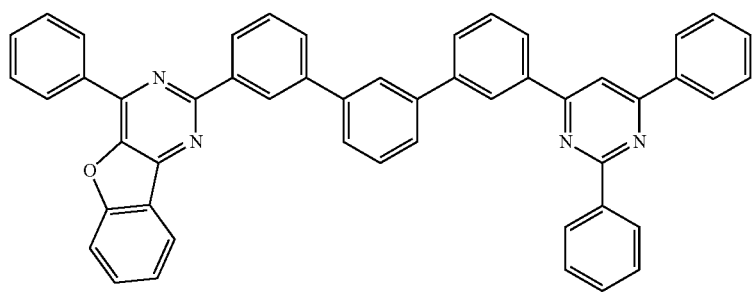
ET-a-12
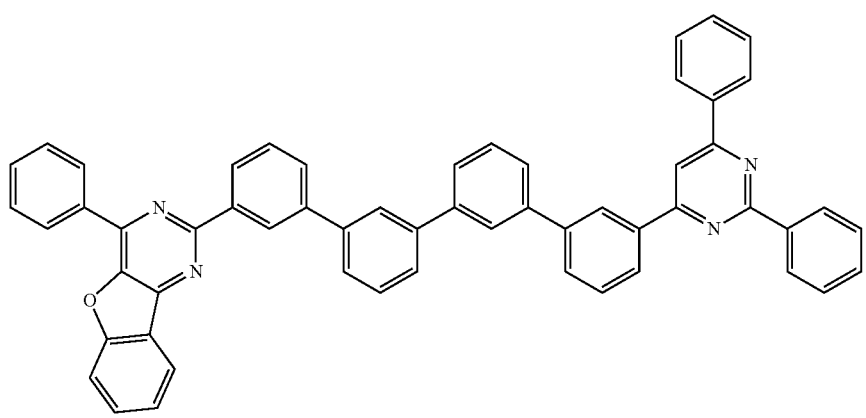
ET-a-13
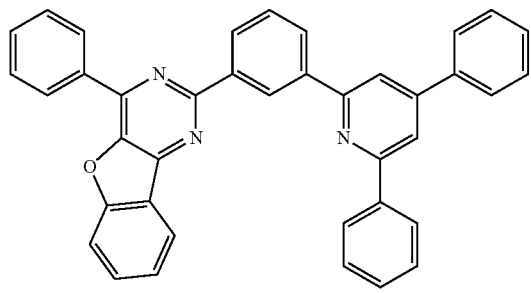
ET-a-14
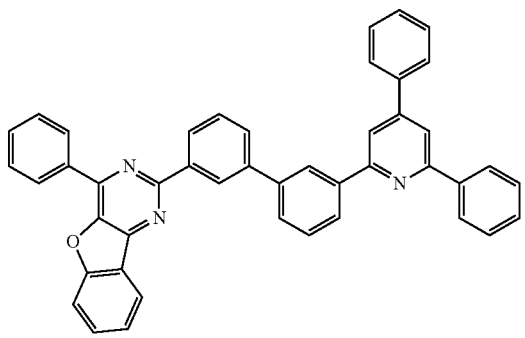

-continued
ET-a-15
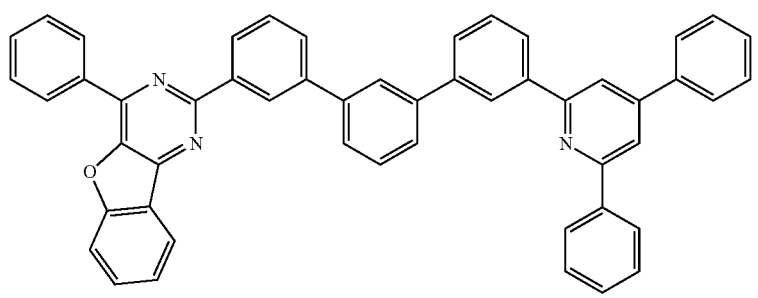
ET-a-16
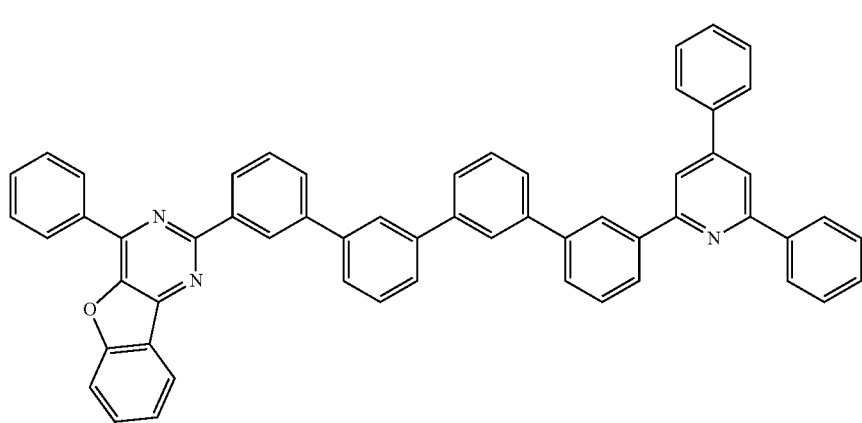
ET-a-17  ET-a-18
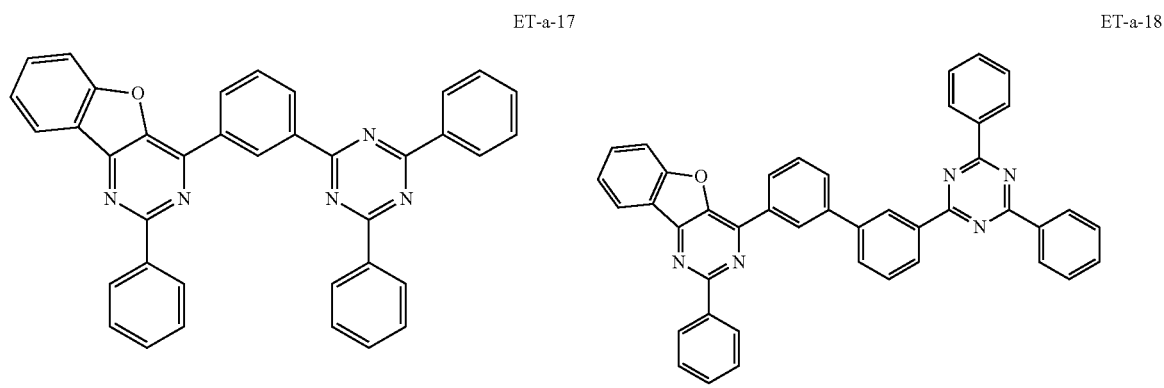
ET-a-19
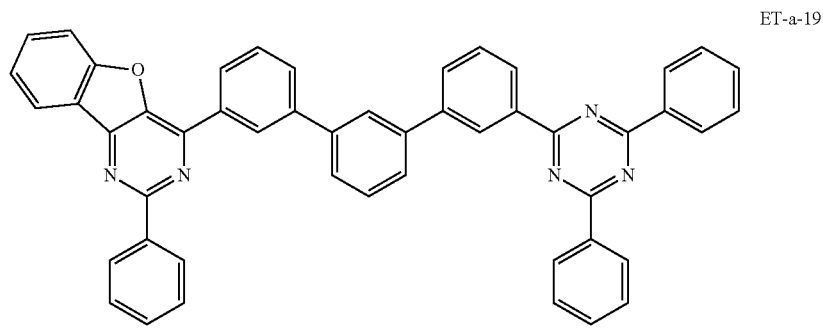

ET-a-20
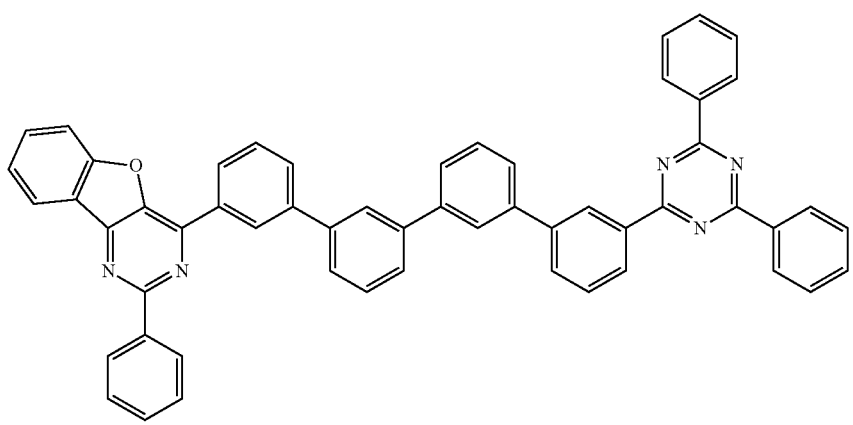
ET-a-21
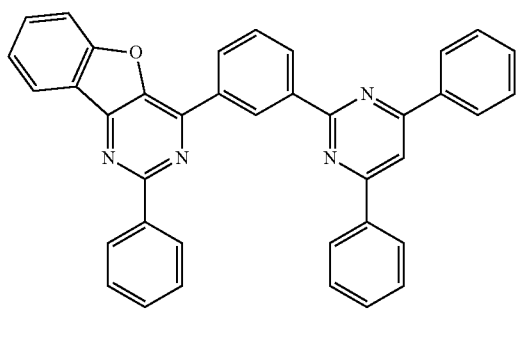
ET-a-22
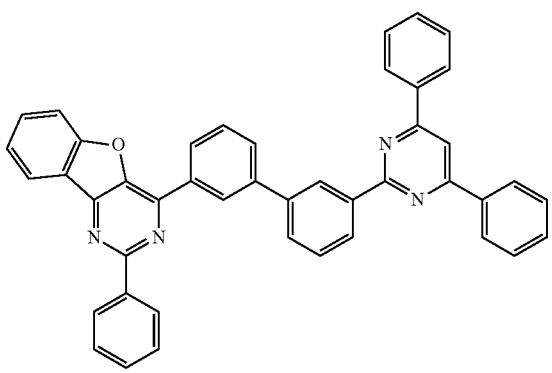
ET-a-23
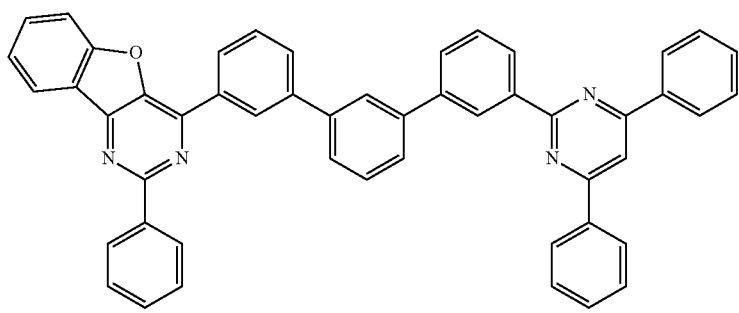
ET-a-24
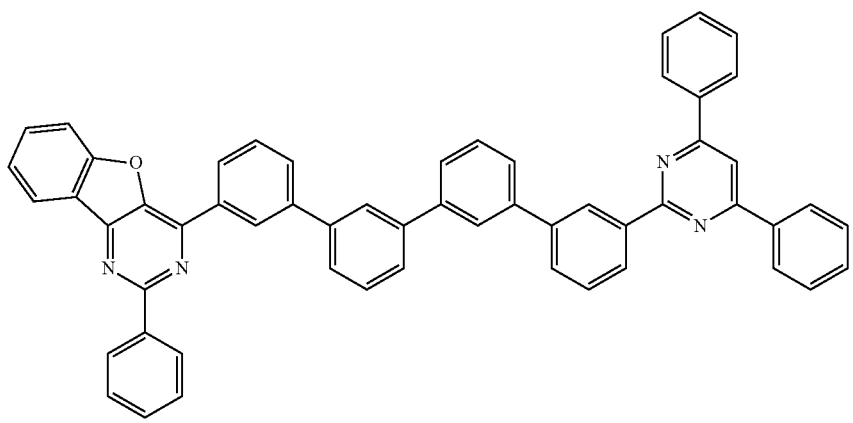

ET-a-25
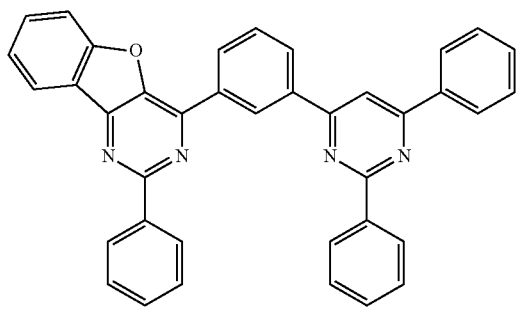
ET-a-26
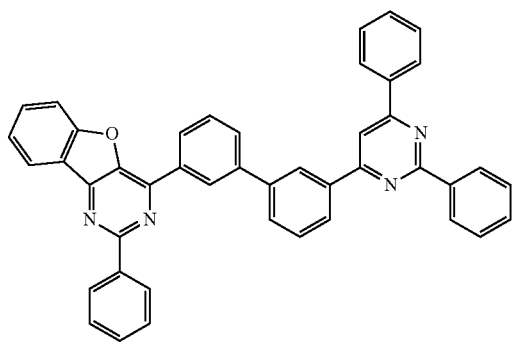
ET-a-27
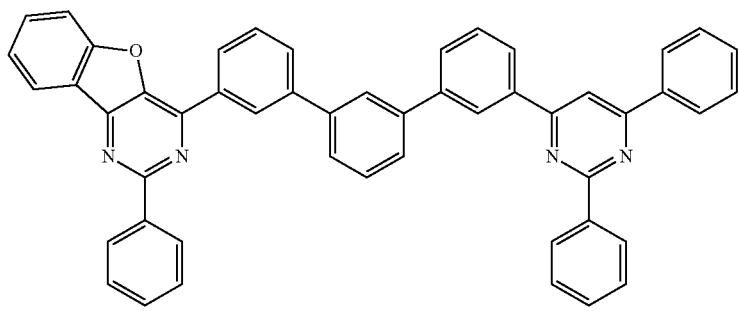
ET-a-28
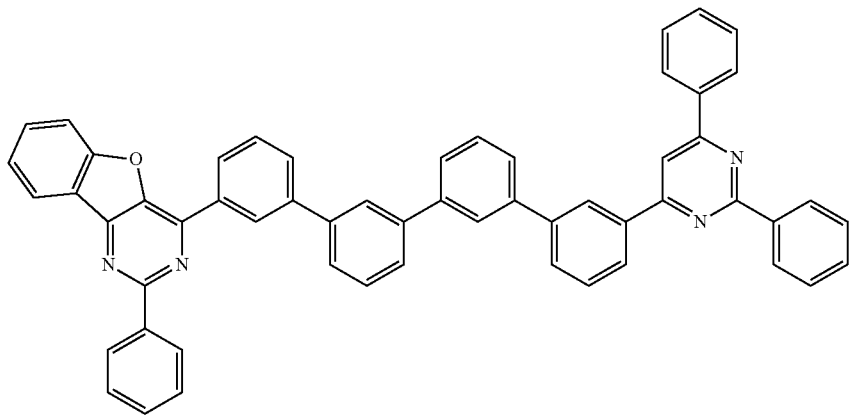
ET-a-29
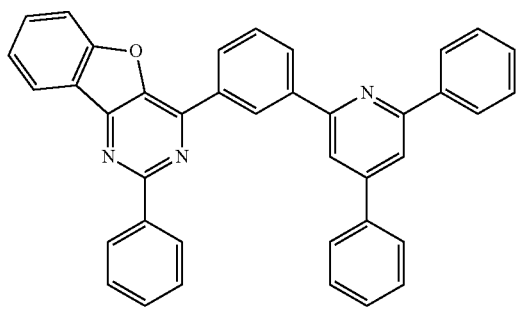
ET-a-30
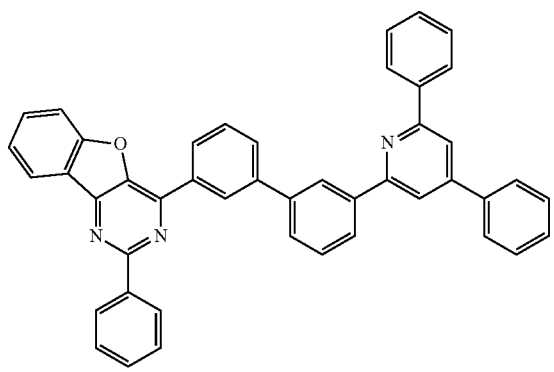

ET-a-31
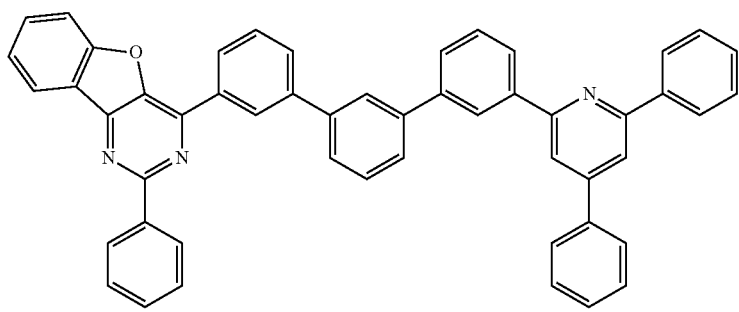
ET-a-32
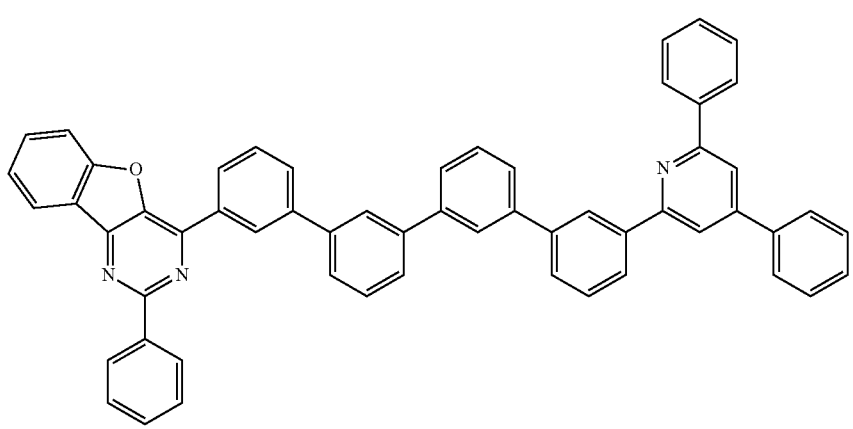
ET-a-33
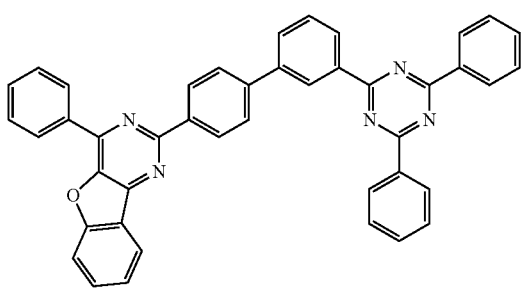
ET-a-34
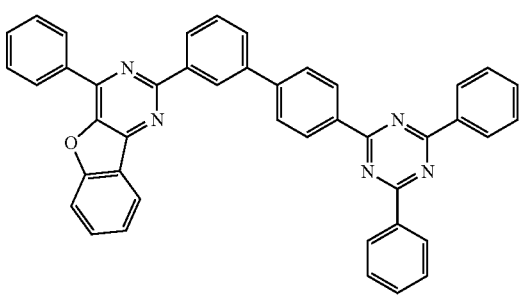
ET-a-35
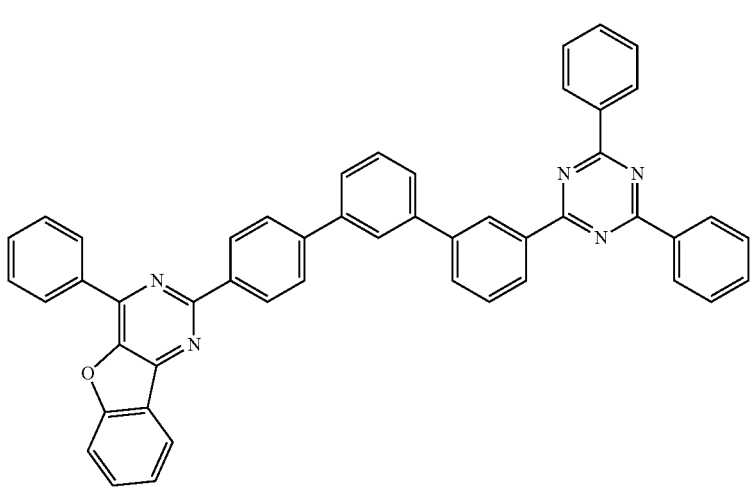

-continued
ET-a-36
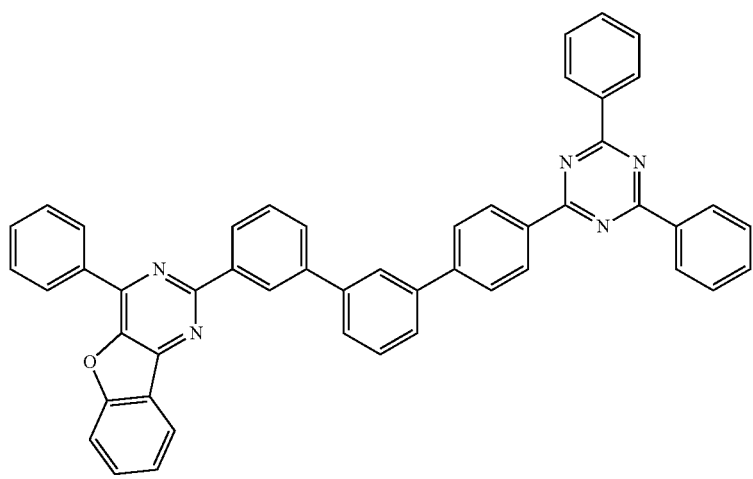
ET-a-37
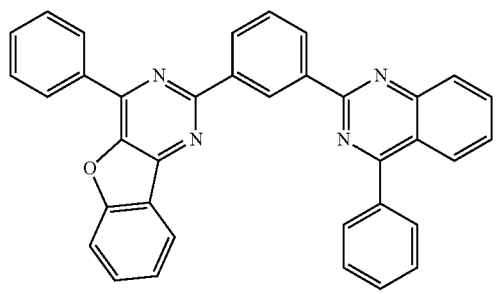
ET-a-38
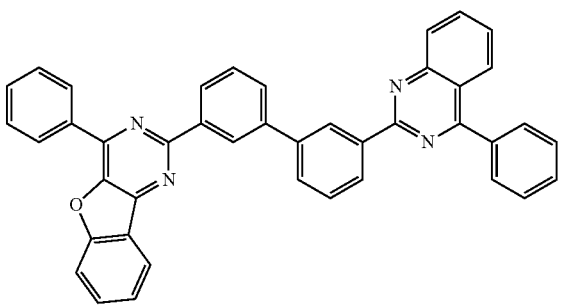
ET-a-39
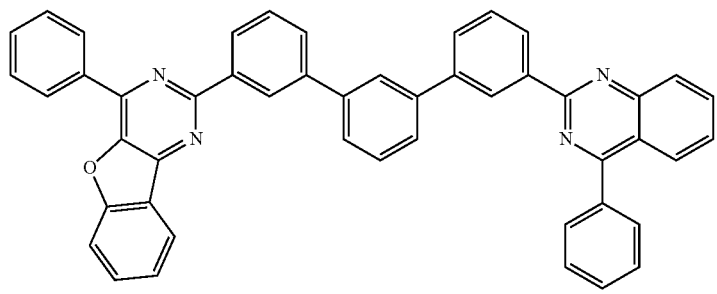
ET-a-40
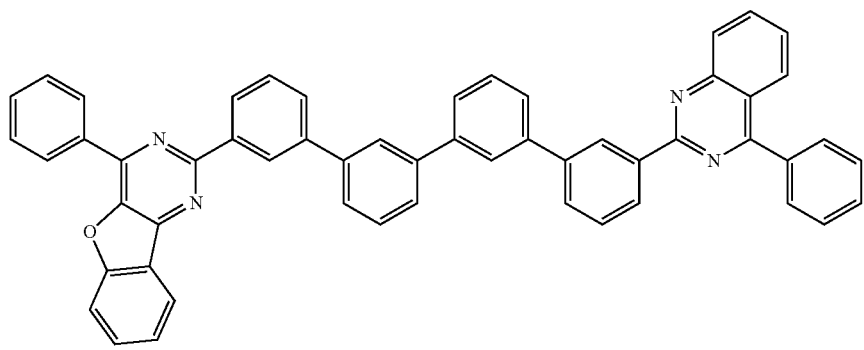

-continued
ET-a-41
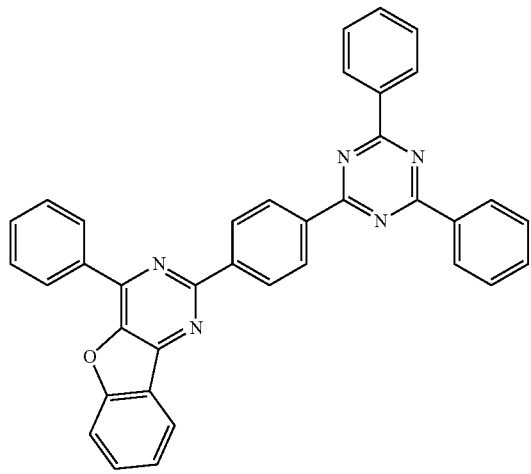
ET-a-42
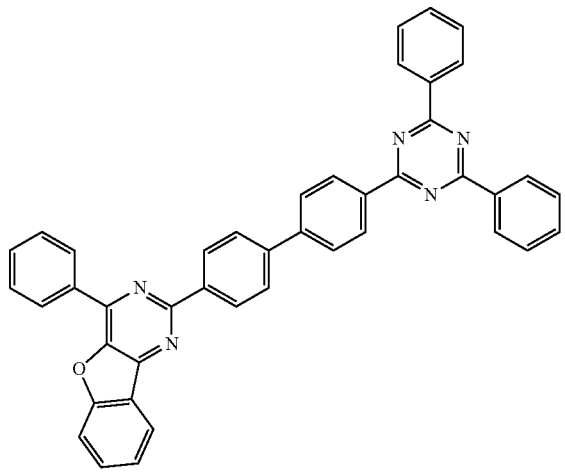
ET-a-43
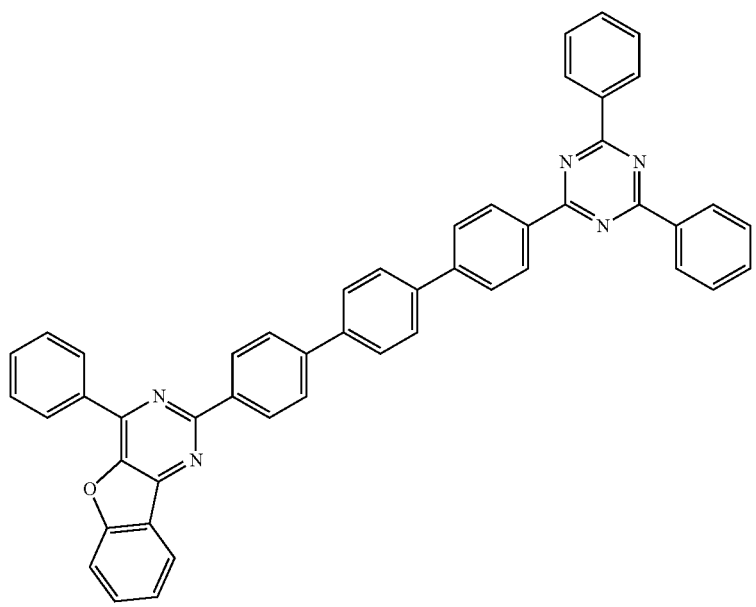

ET-a-44
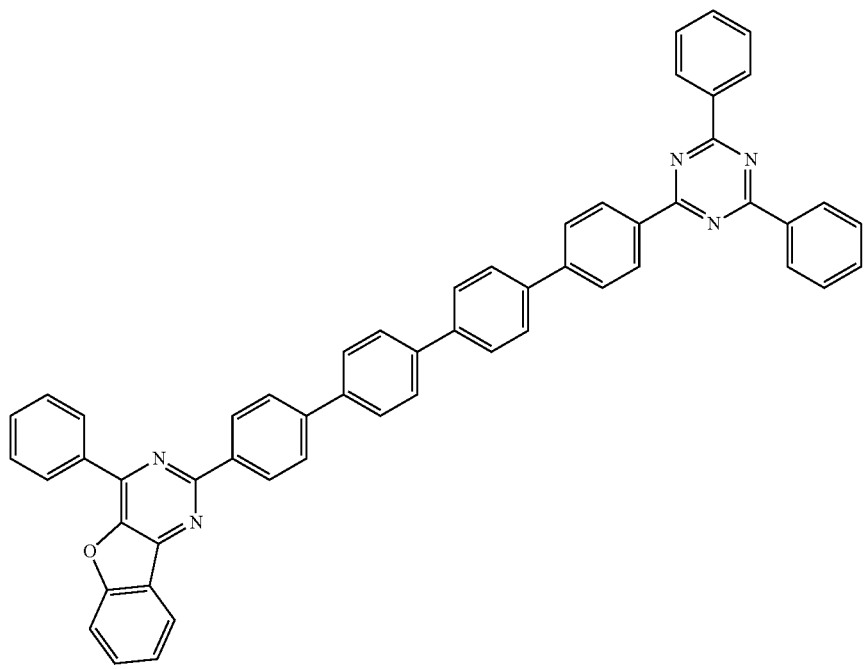
(X = S)
ET-b-1
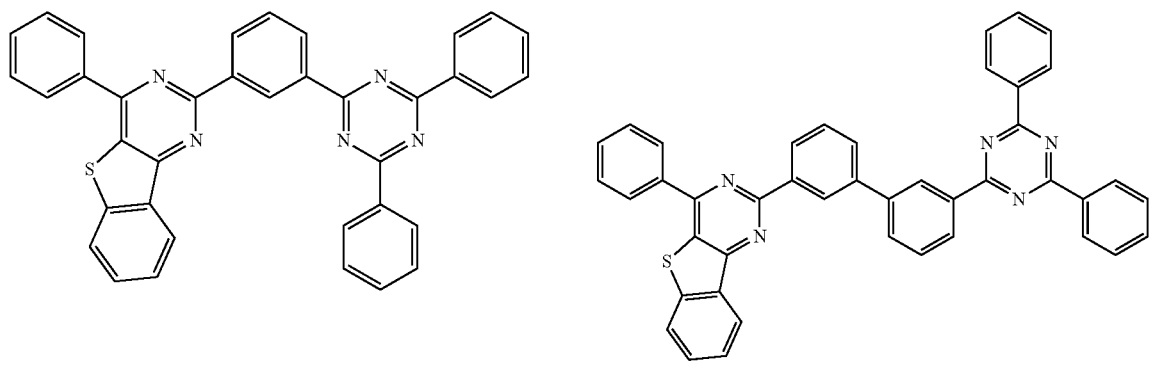
ET-b-2
ET-b-3
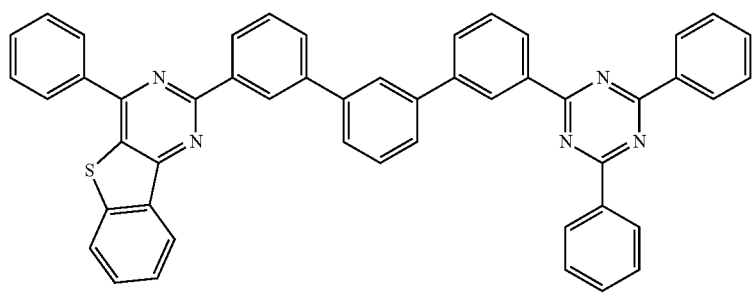

ET-b-4
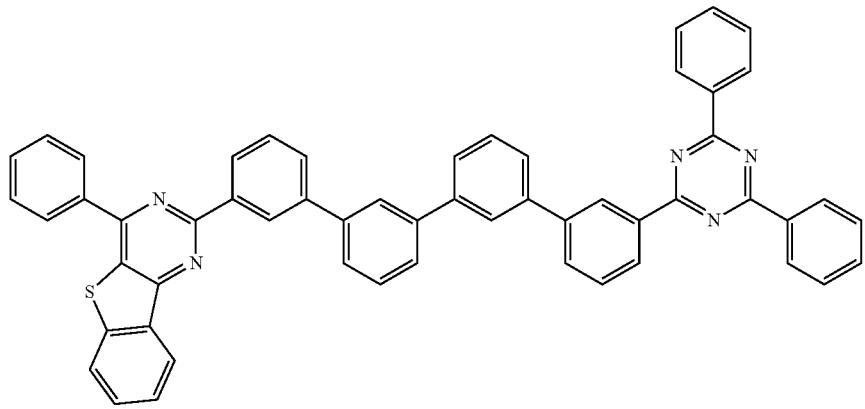
ET-b-5 ET-b-6
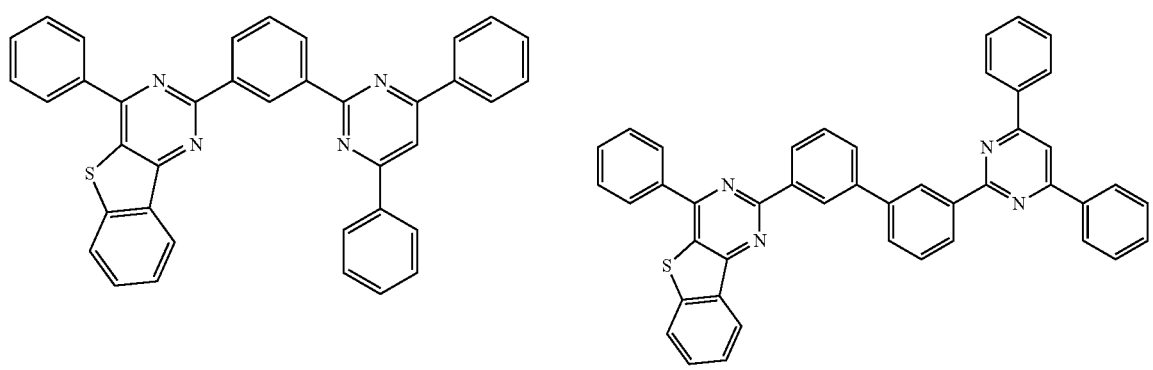
ET-b-7
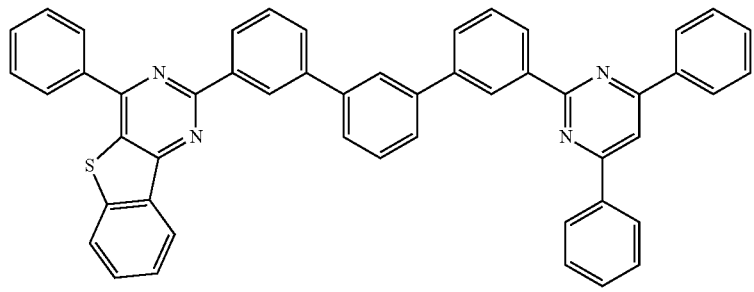
ET-b-8
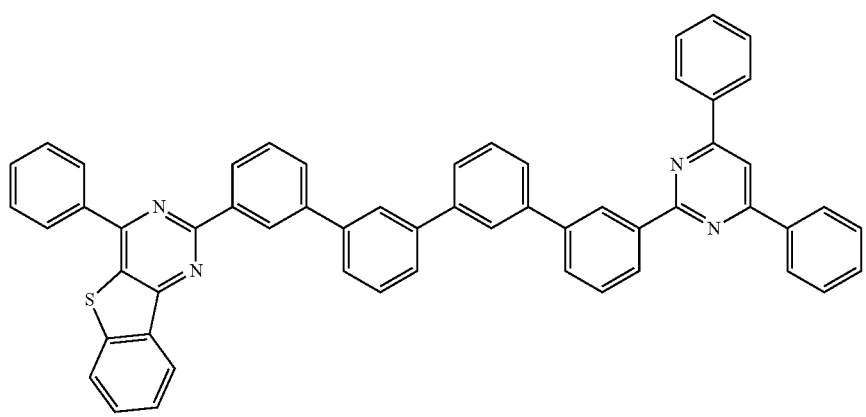

-continued
ET-b-9
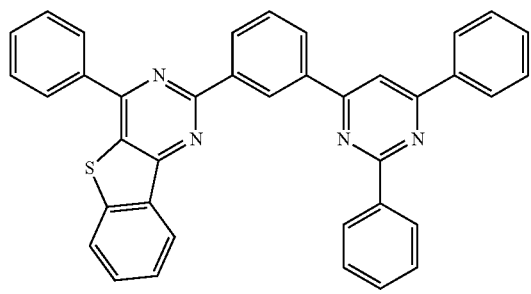
ET-b-10
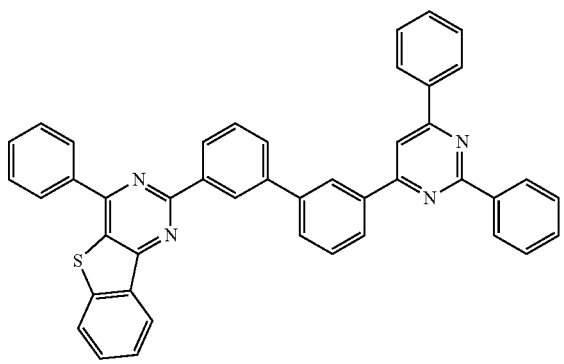
ET-b-11
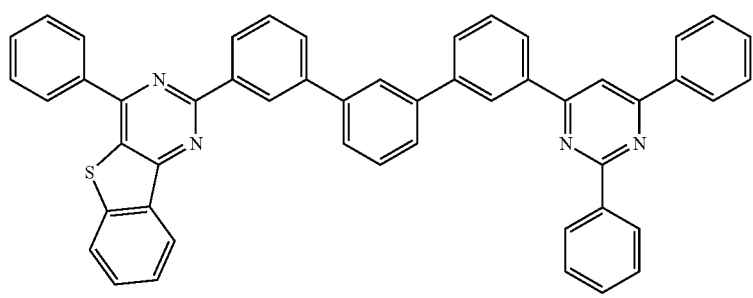
ET-b-12
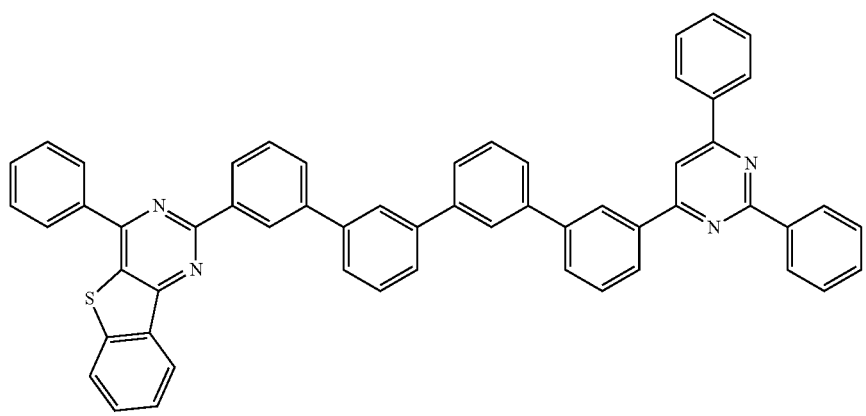
ET-b-13
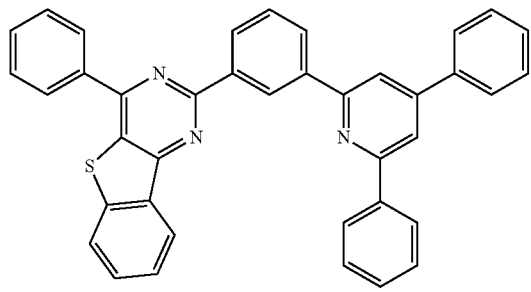
ET-b-14
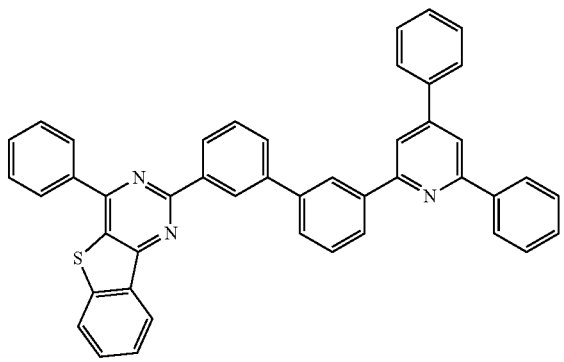

-continued
ET-b-15
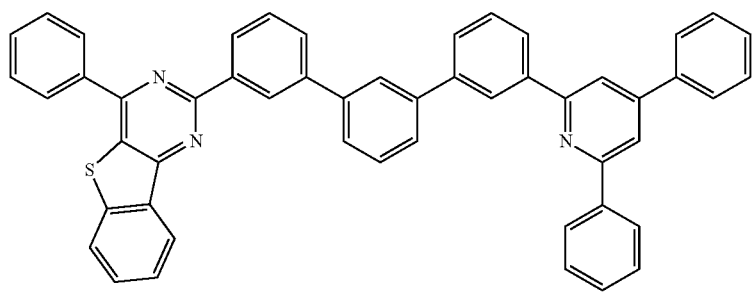
ET-b-16
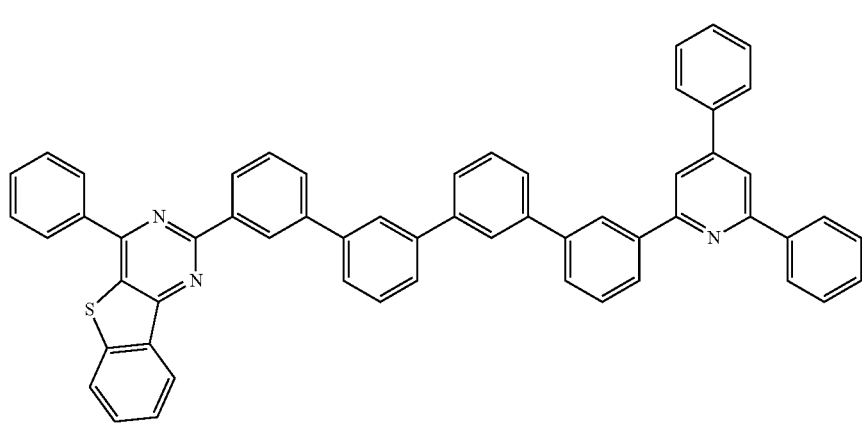
ET-b-17 ET-b-18
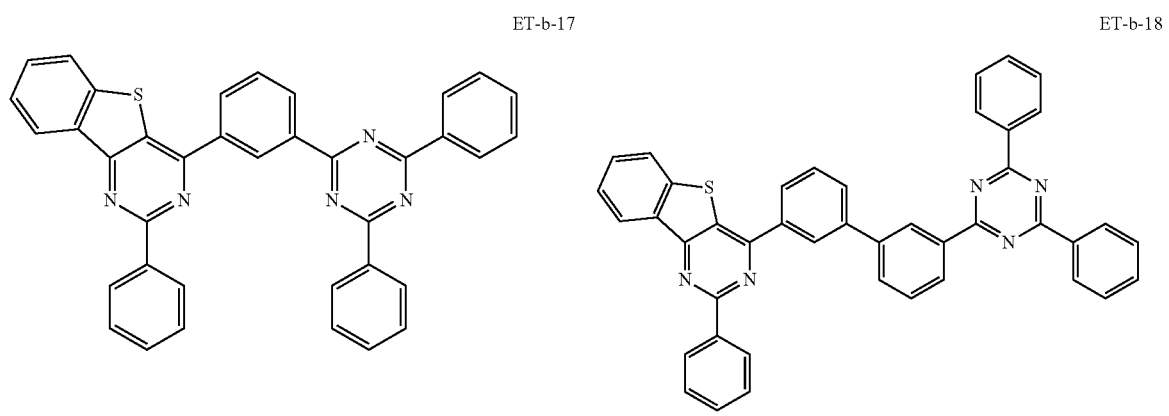
ET-b-19
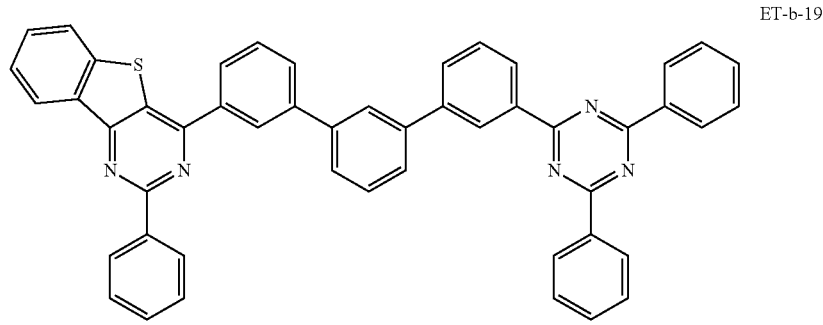

-continued
ET-b-20
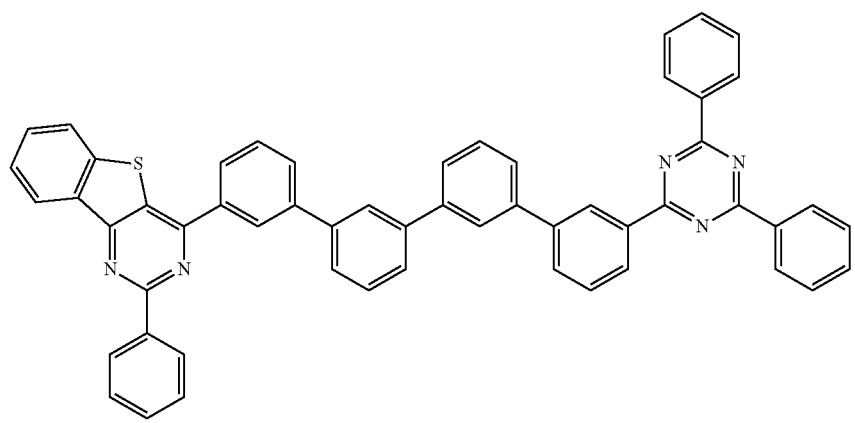
ET-b-21
ET-b-22
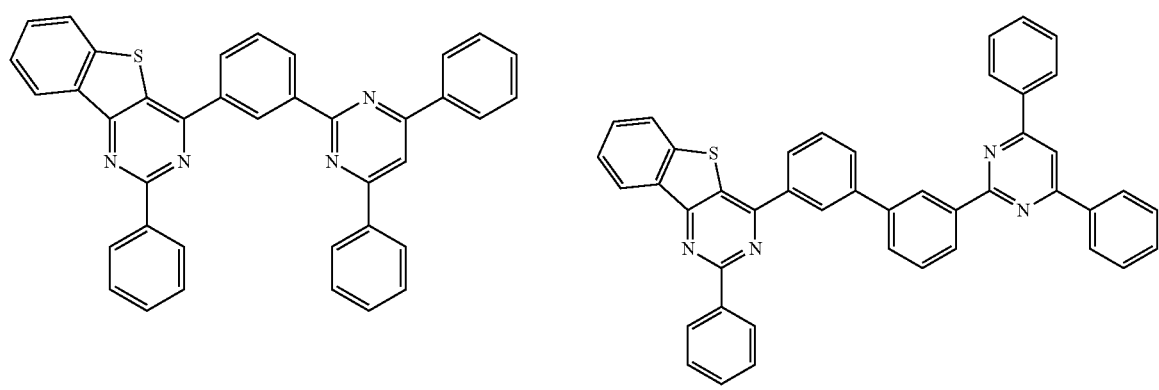
ET-b-23
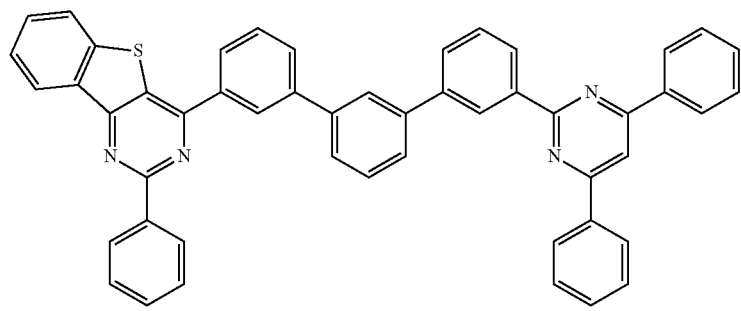
ET-b-24
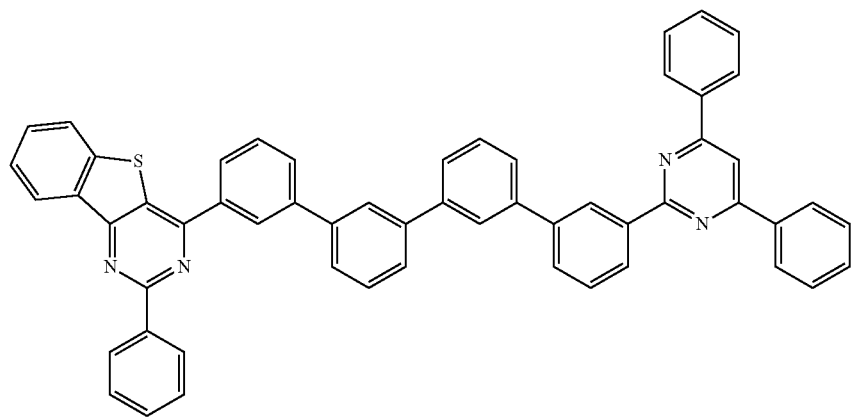

-continued
ET-b-25
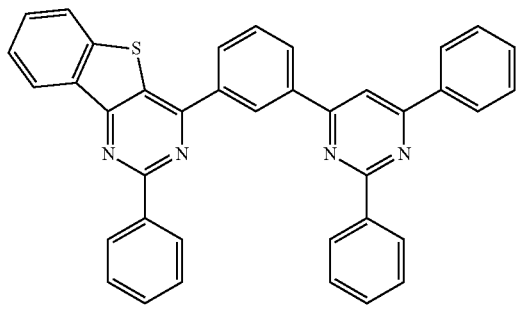
ET-b-26
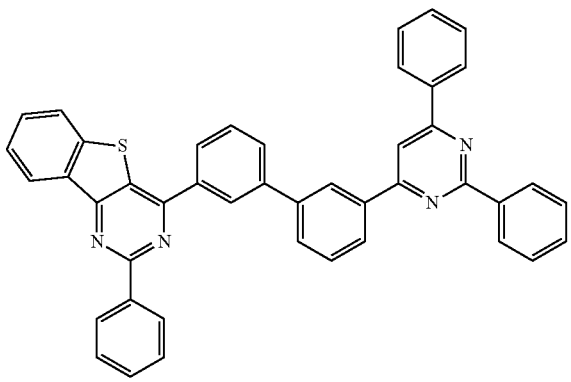
ET-b-27
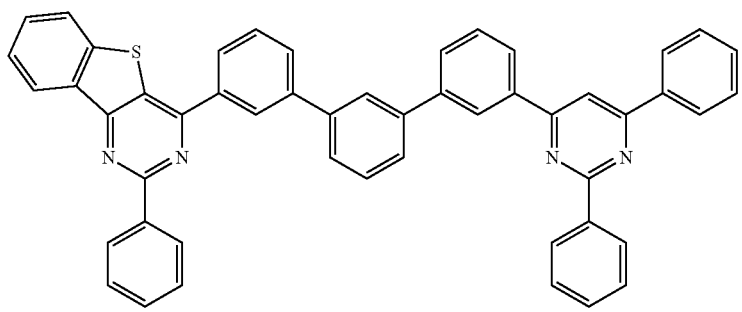
ET-b-28
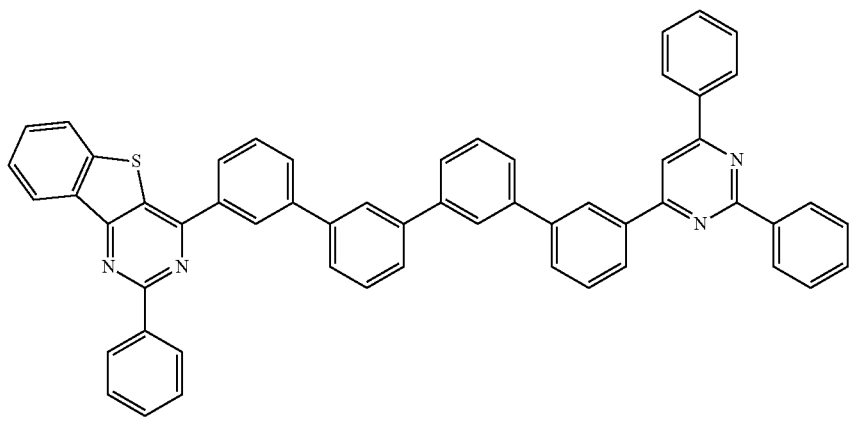
ET-b-29
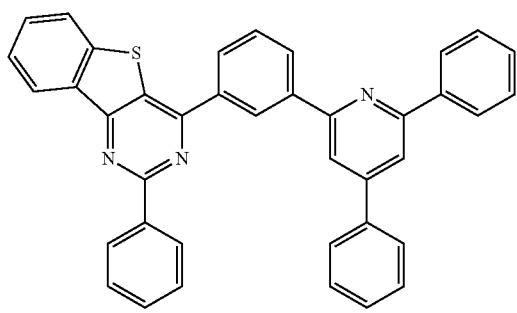
ET-b-30
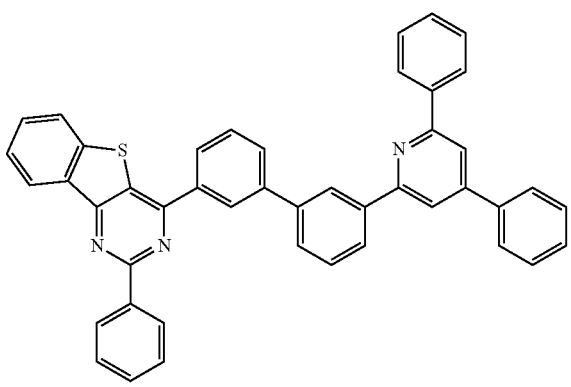

-continued
ET-b-31
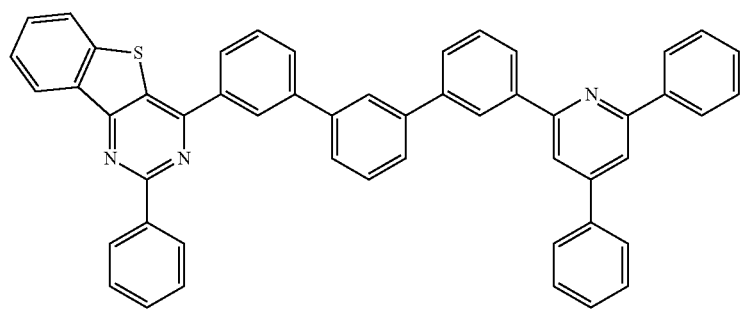
ET-b-32
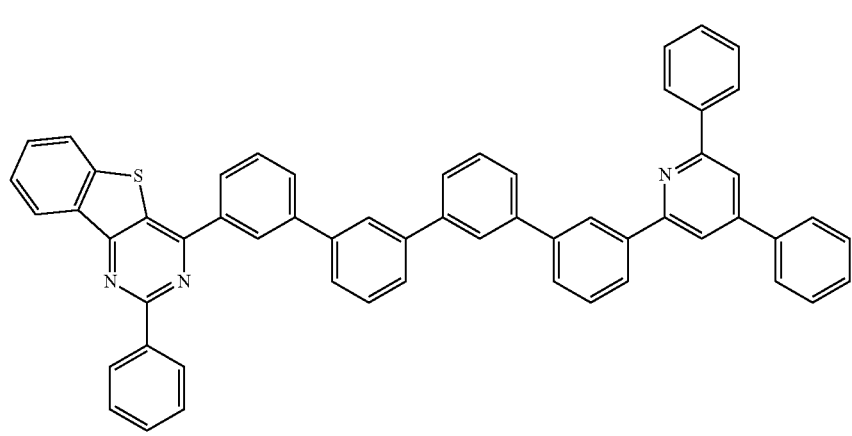
ET-b-33  ET-b-34
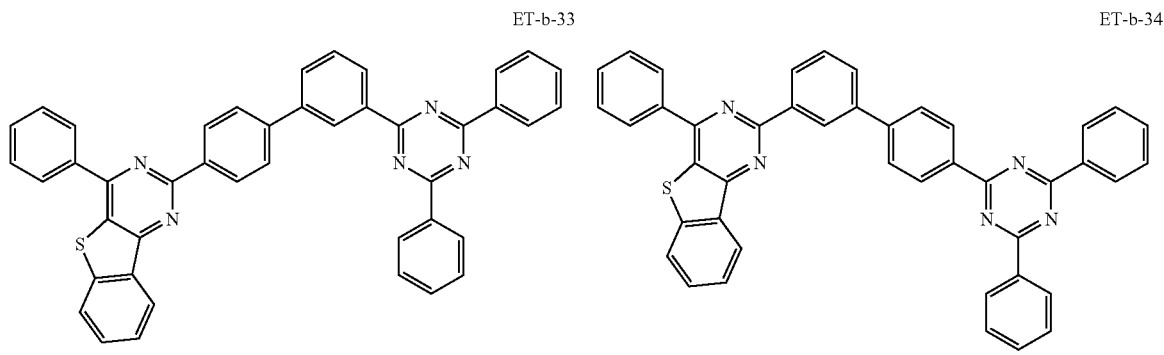
ET-b-35
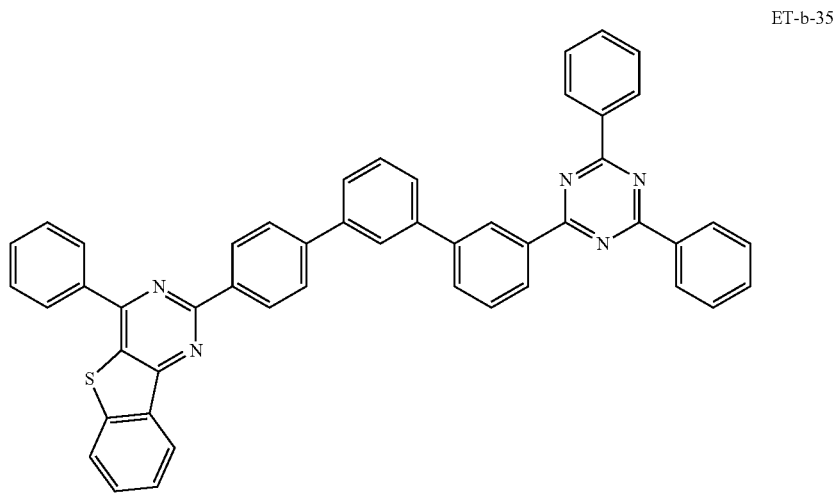

-continued
ET-b-36
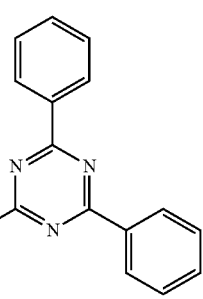
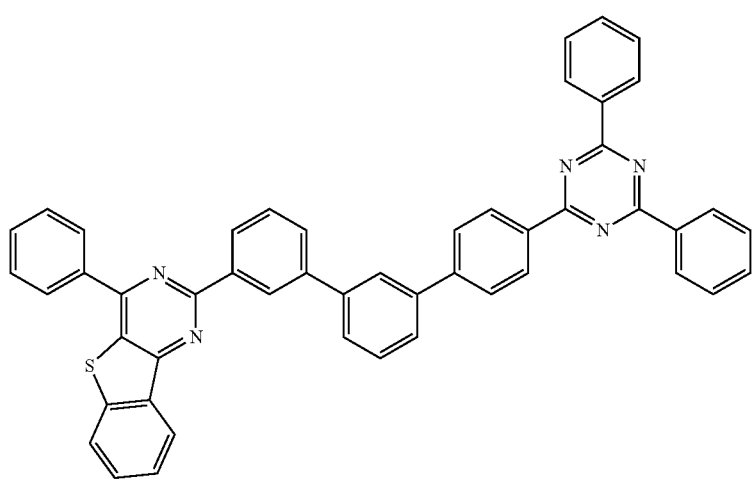
ET-b-37
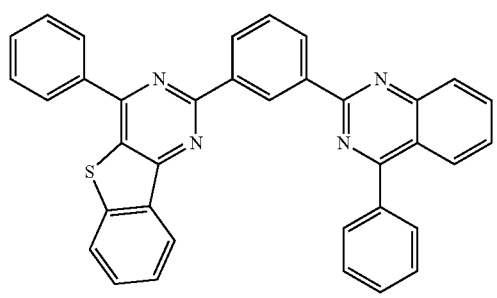
ET-b-38
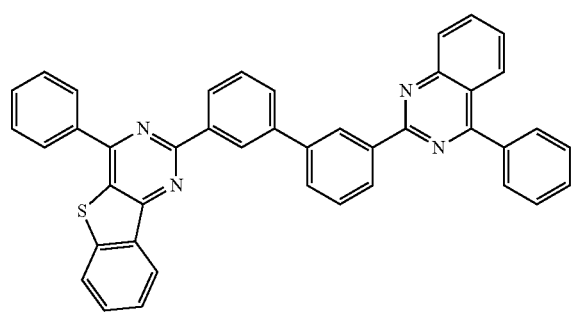
ET-b-39
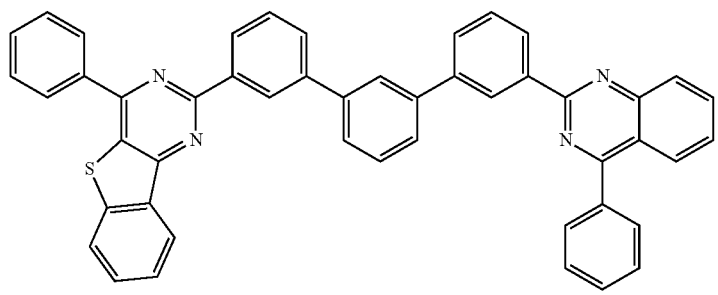
ET-b-40
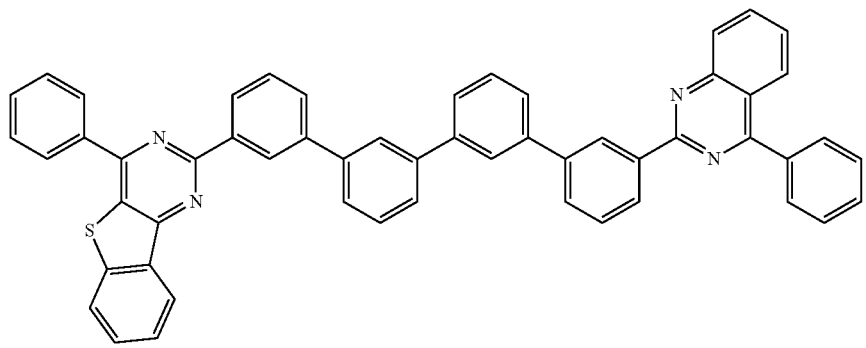

-continued
ET-b-41
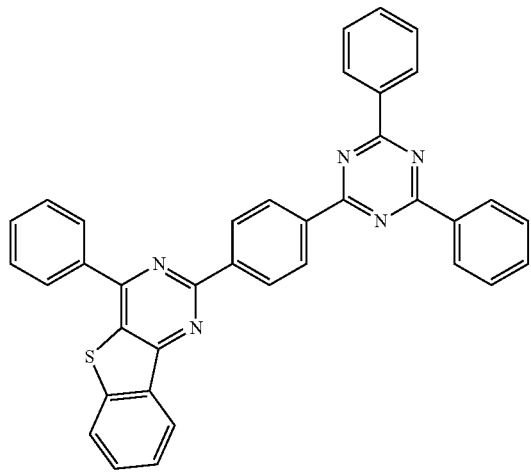
ET-b-42
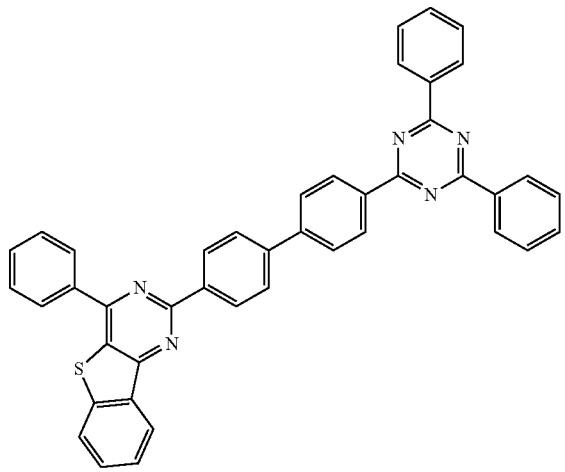
ET-b-43
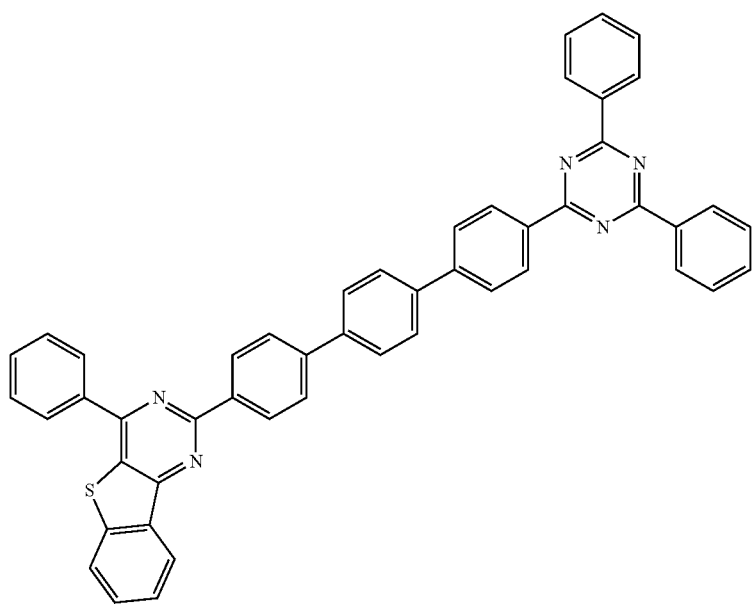

ET-b-44
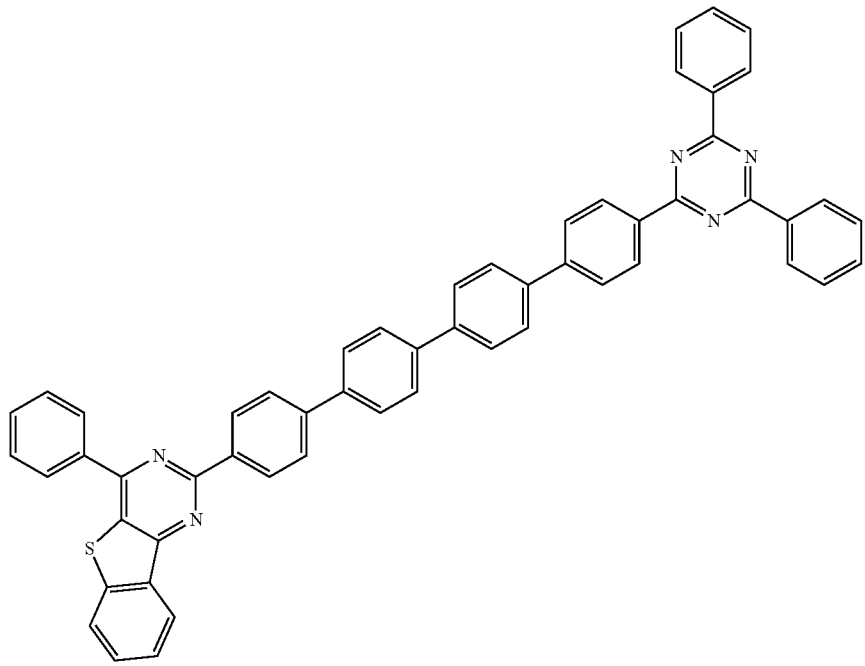
ET-b-45
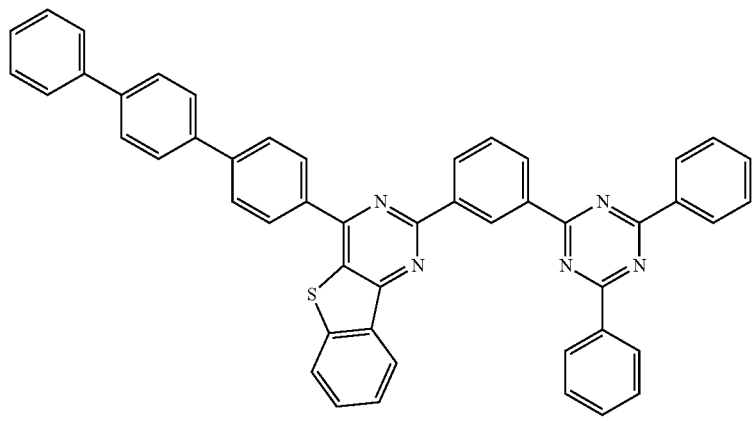
ET-b-46 ET-b-47
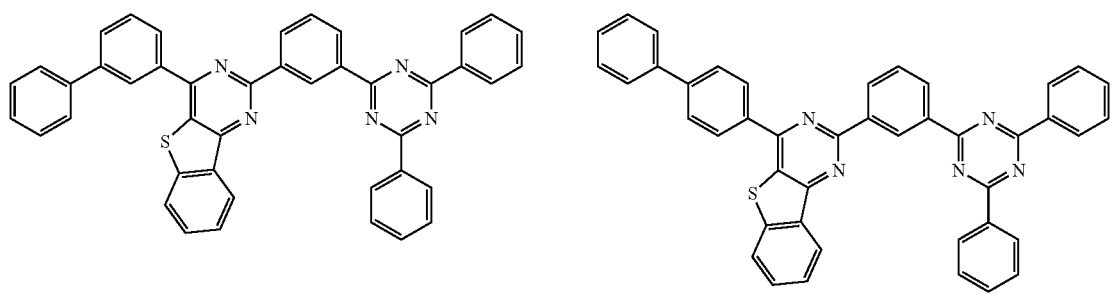

-continued
ET-b-48
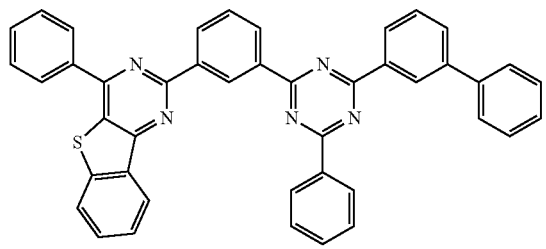
ET-b-49
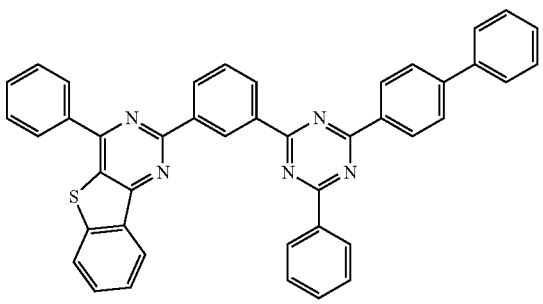
ET-b-50
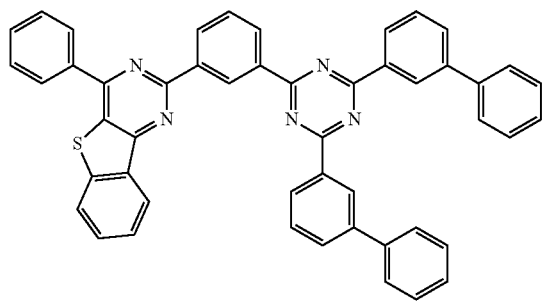
ET-b-51
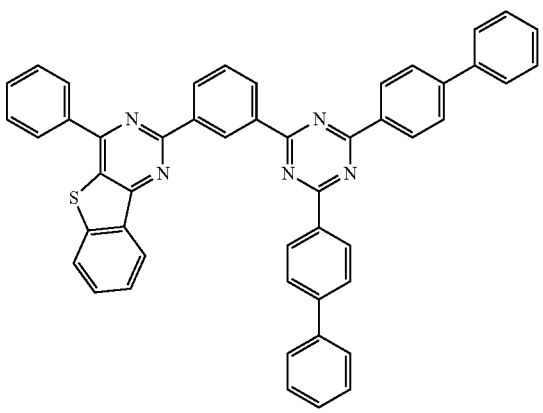
ET-b-52
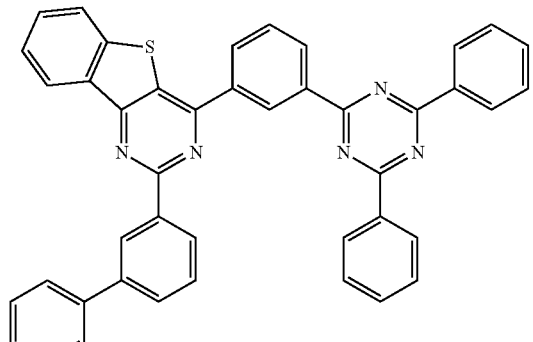
ET-b-53
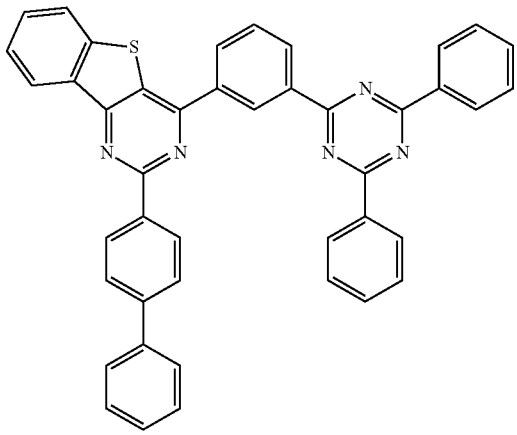
ET-b-54
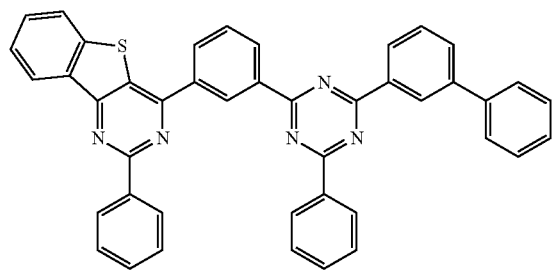
ET-b-55
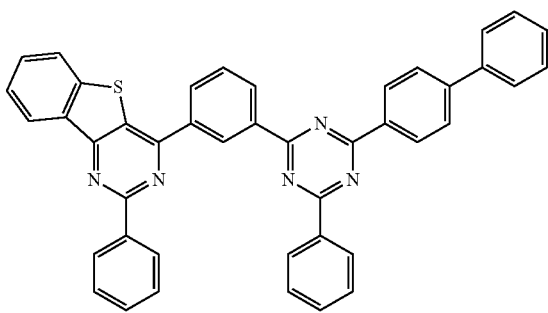

-continued
ET-b-56
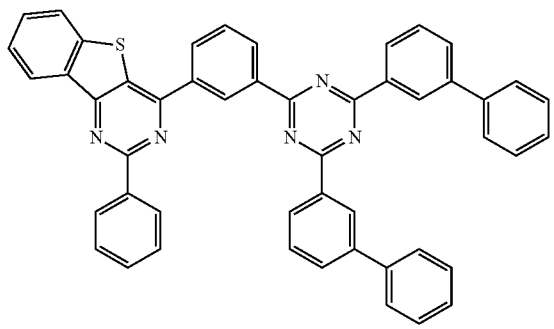
ET-b-57
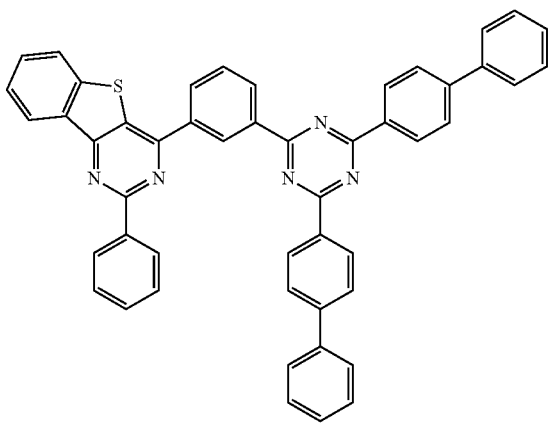
ET-b-58
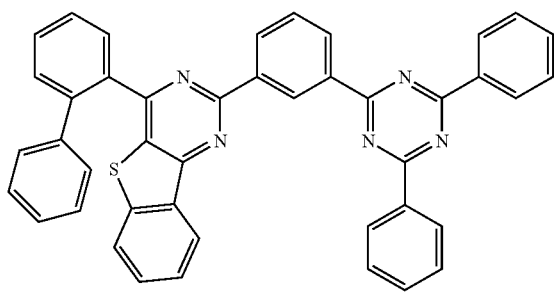
ET-b-59
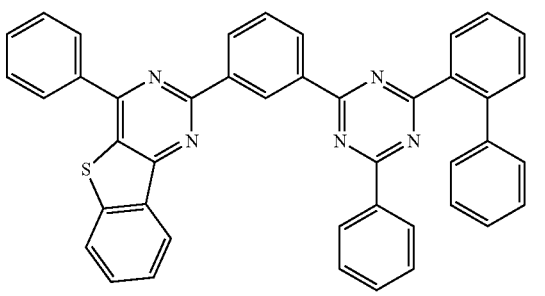
ET-b-60
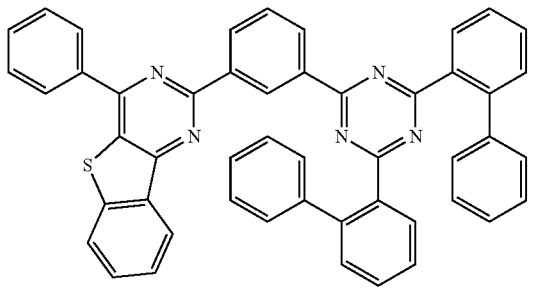
ET-b-61
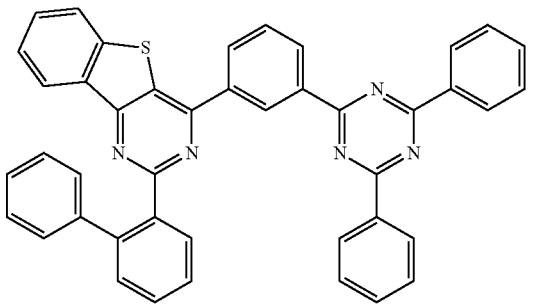
ET-b-62
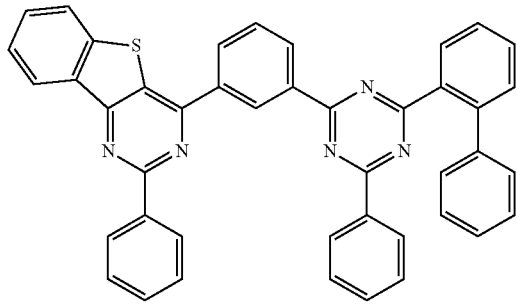
ET-b-63
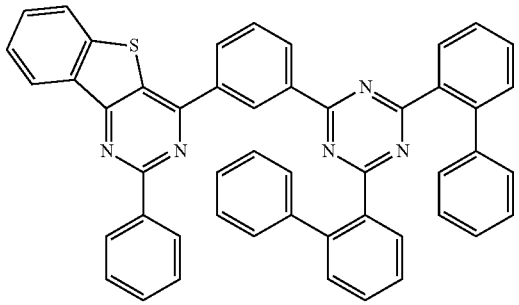

-continued
ET-b-64
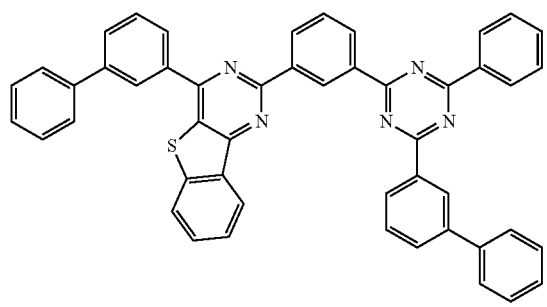
ET-b-65
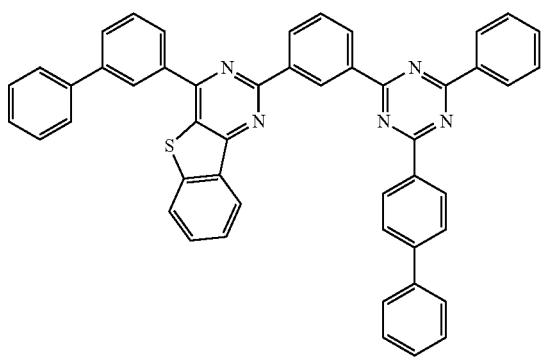
ET-b-66
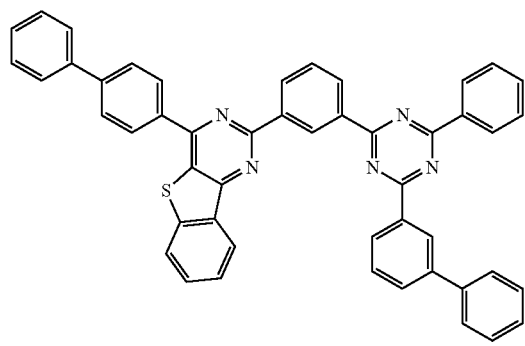
ET-b-67
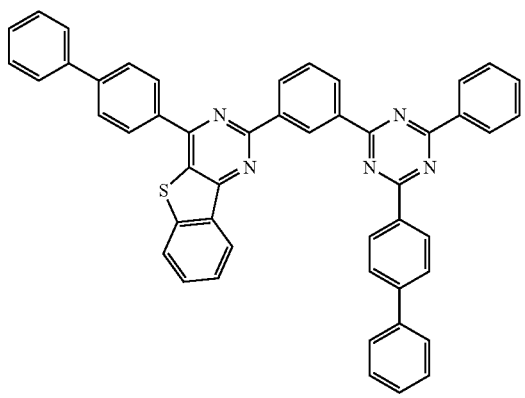
ET-b-68
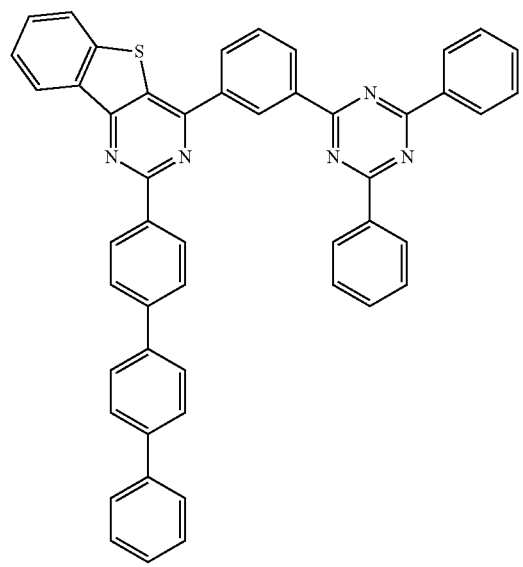
ET-b-69
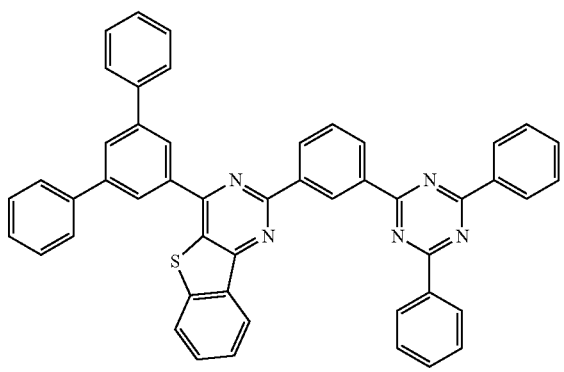

-continued
ET-b-70
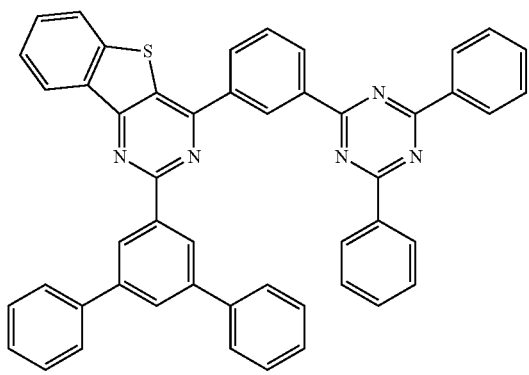
ET-b-71
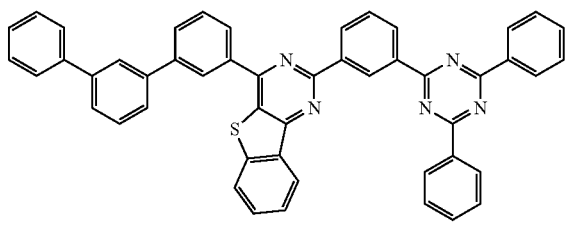
ET-b-72
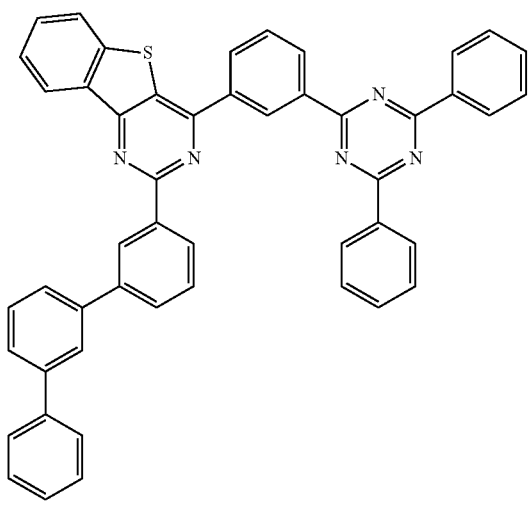
(X = O)
ET-c-1
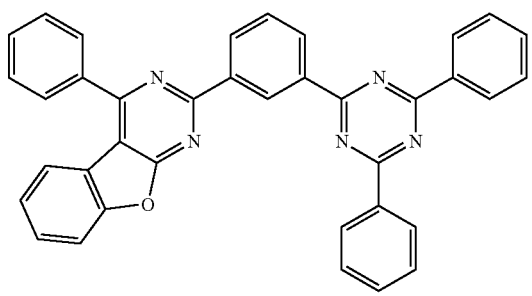
ET-c-2
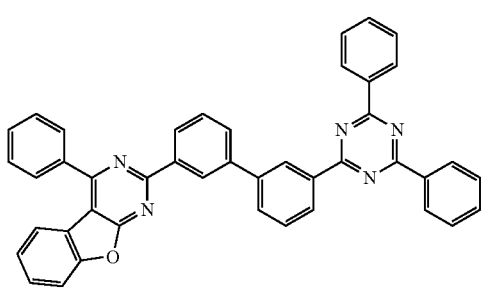
ET-c-3
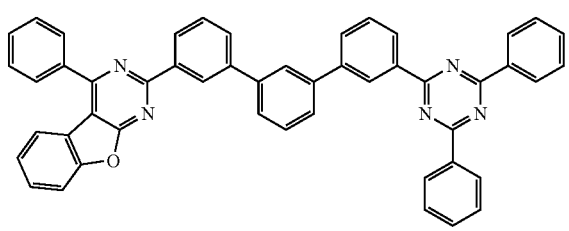
ET-c-4
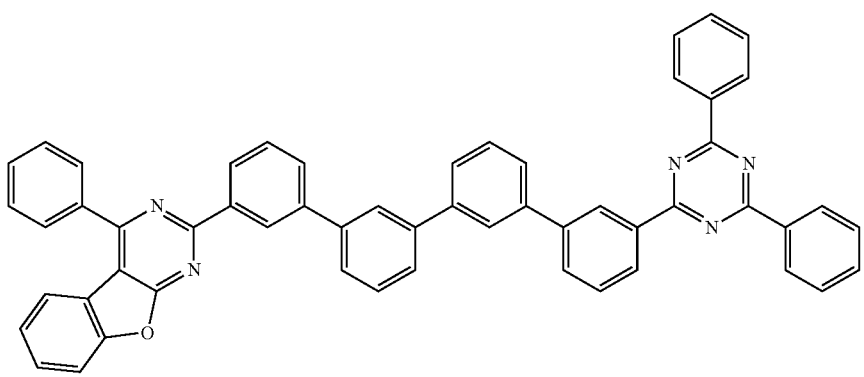

-continued
ET-c-5
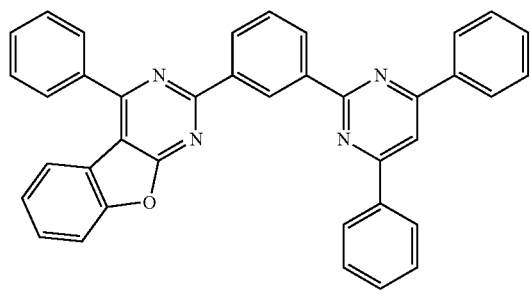
ET-c-6
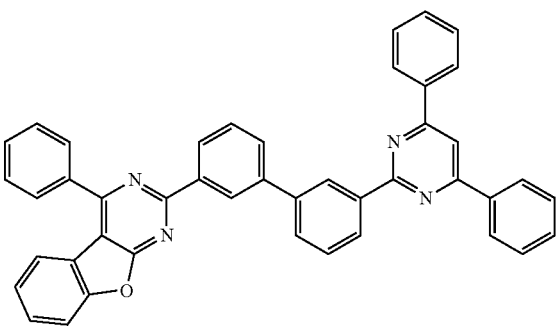
ET-c-7
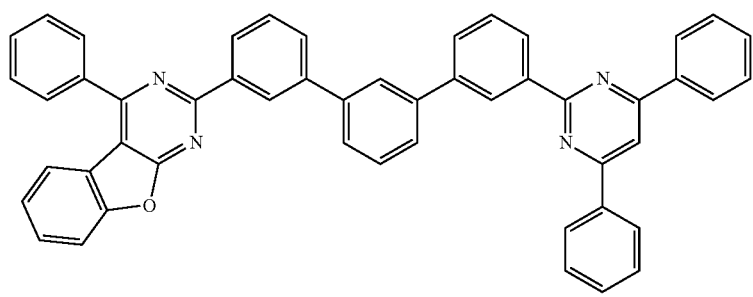
ET-c-8
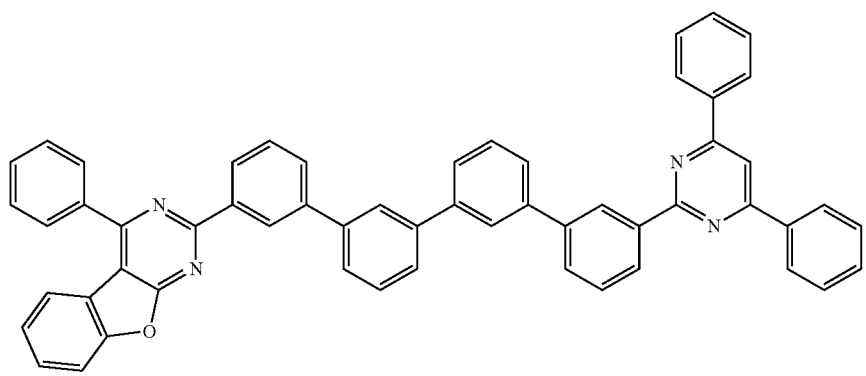
ET-c-9
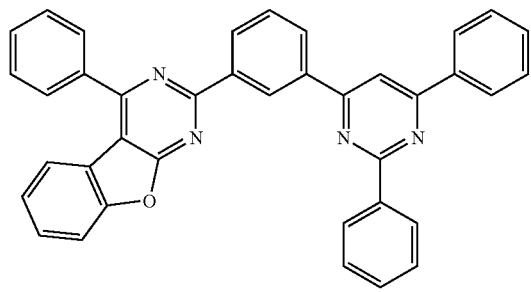
ET-c-10
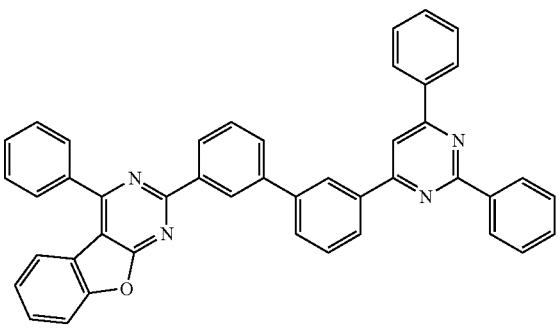

-continued
ET-c-11
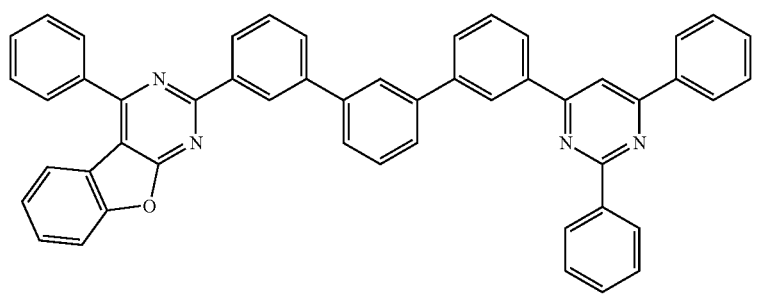
ET-c-12
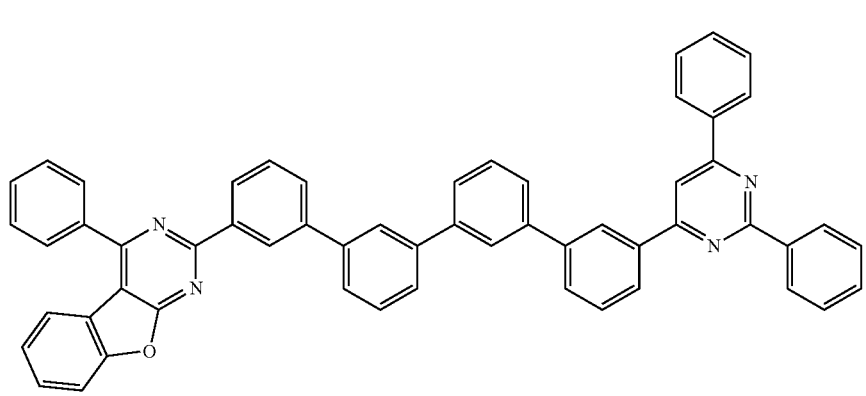
ET-c-13
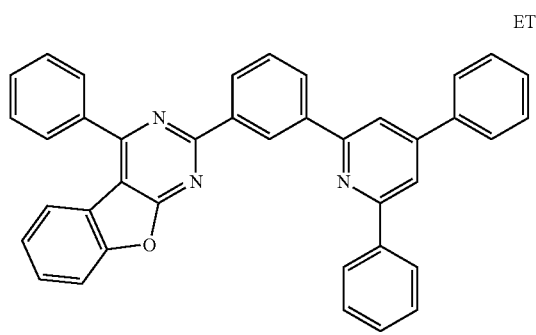
ET-c-14
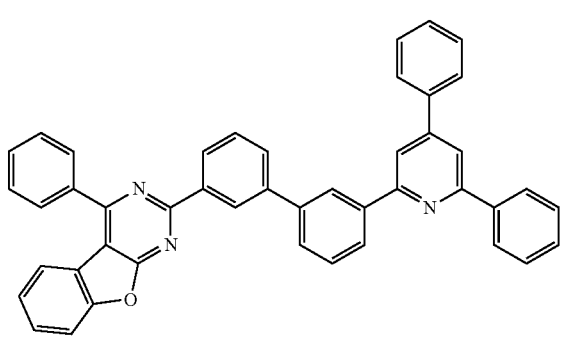
ET-c-15
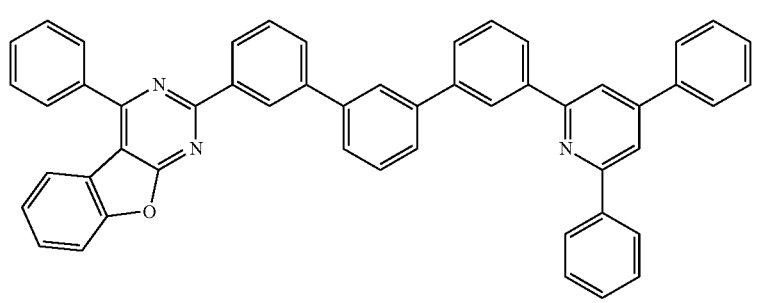

-continued
ET-c-16
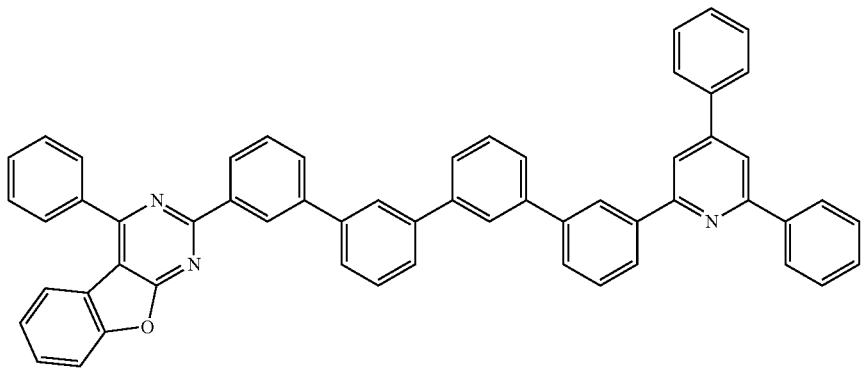
ET-c-17
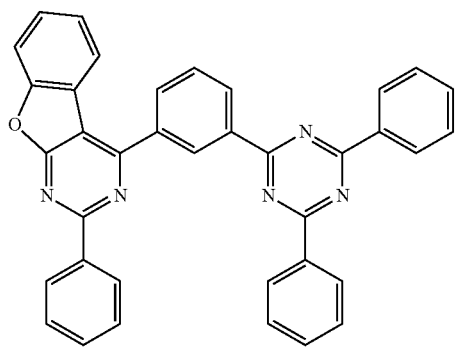
ET-c-18
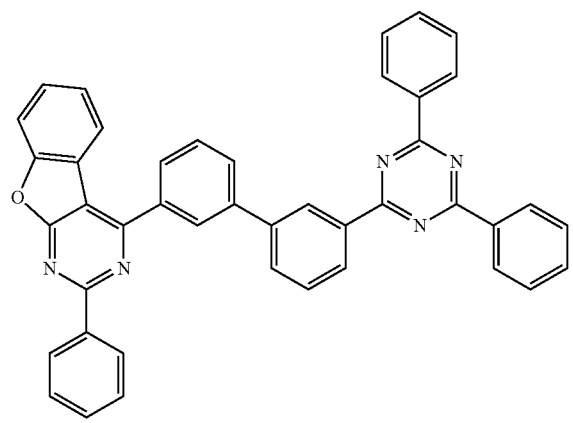
ET-c-19
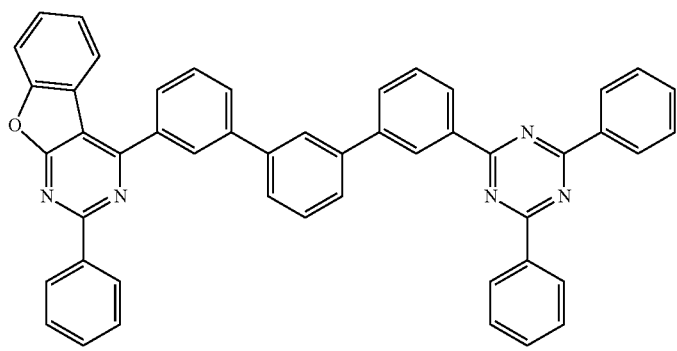
ET-c-20
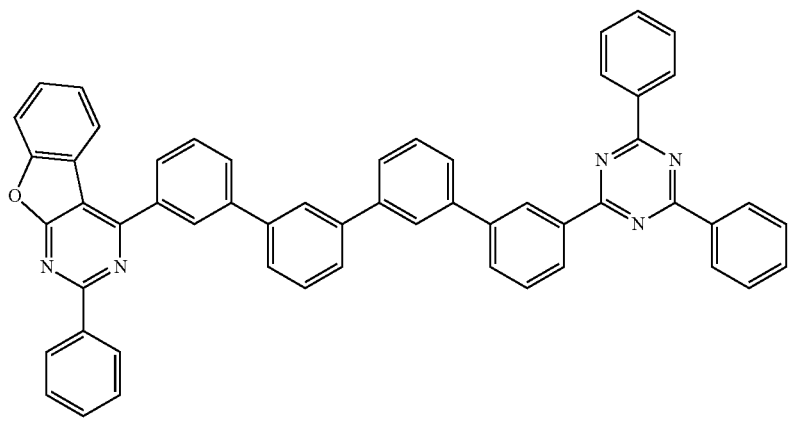
(X = S)

-continued
ET-d-1
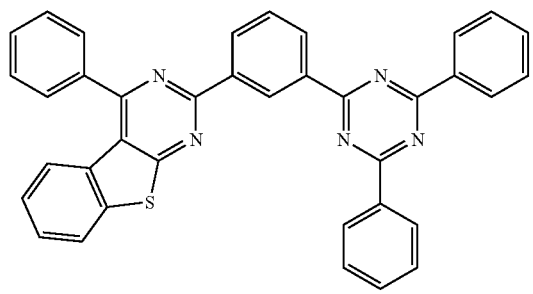
ET-d-2
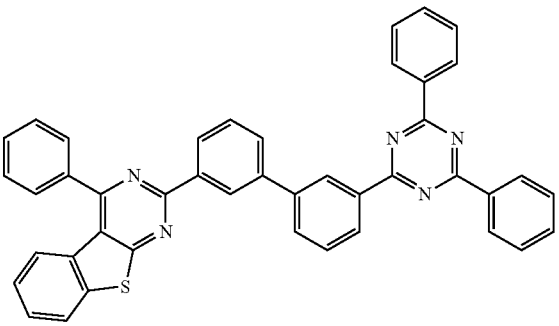
ET-d-3
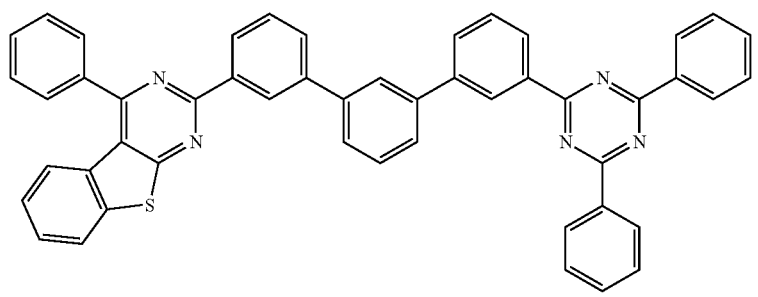
ET-d-4
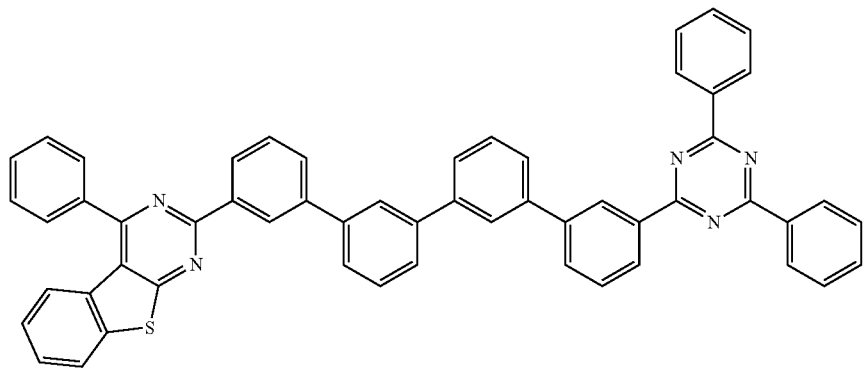
ET-d-5
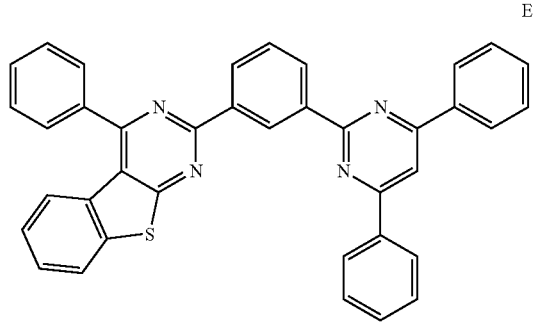
ET-d-6
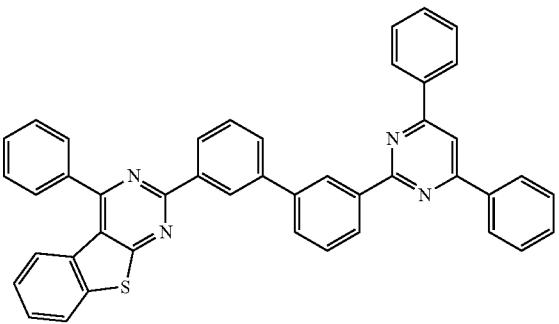

-continued
ET-d-7
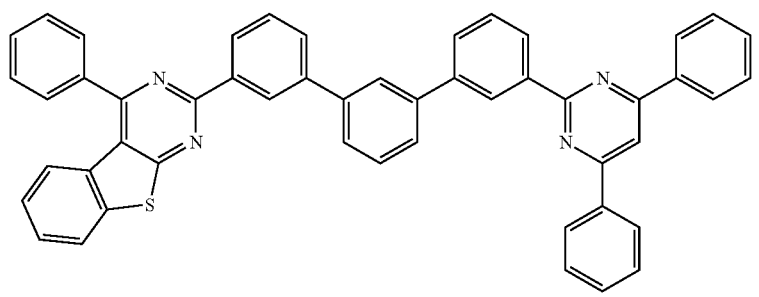
ET-d-8
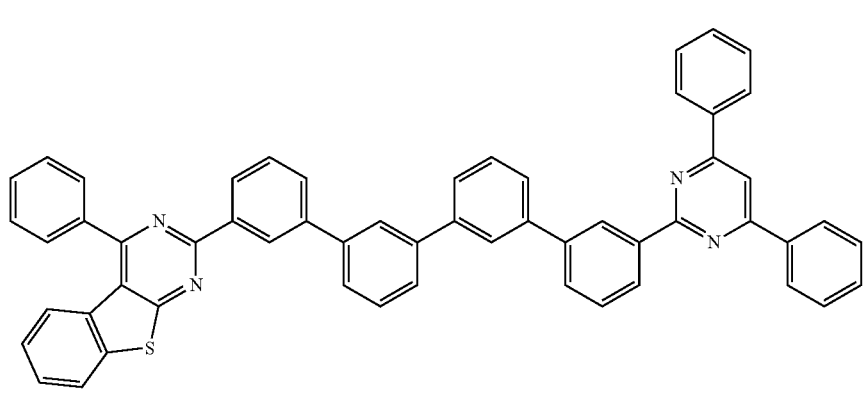
ET-d-9
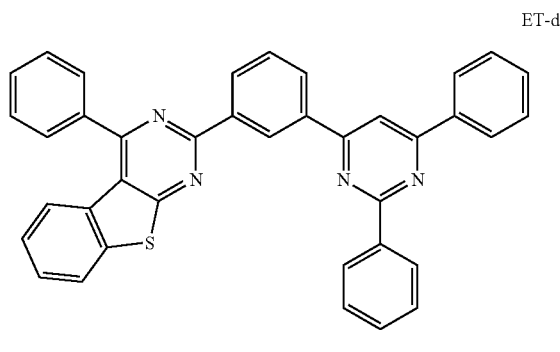
ET-d-10
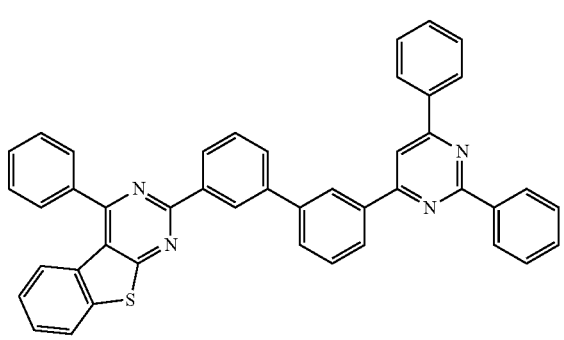
ET-d-11
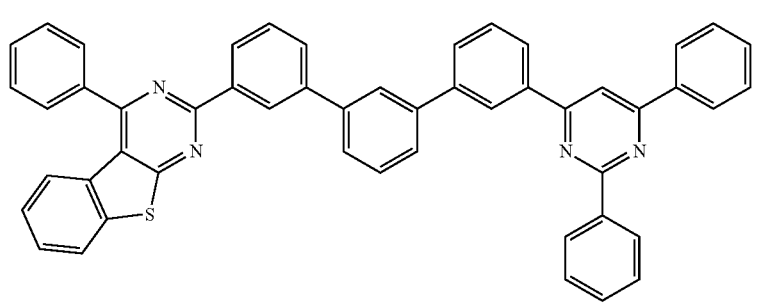

ET-d-12
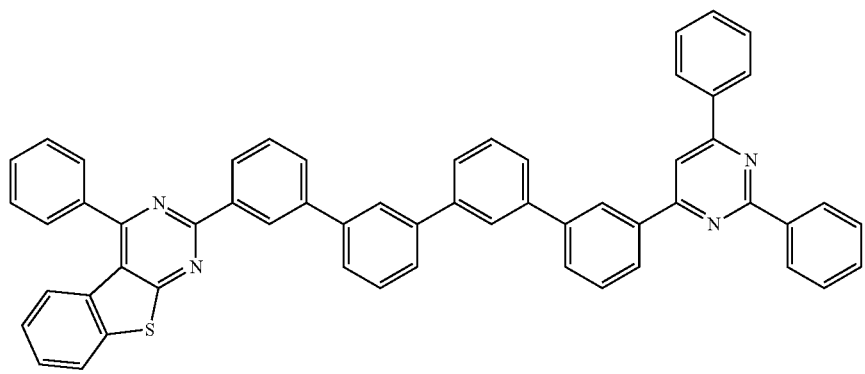
ET-d-13
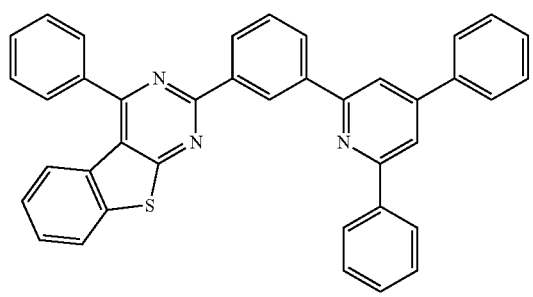
ET-d-14
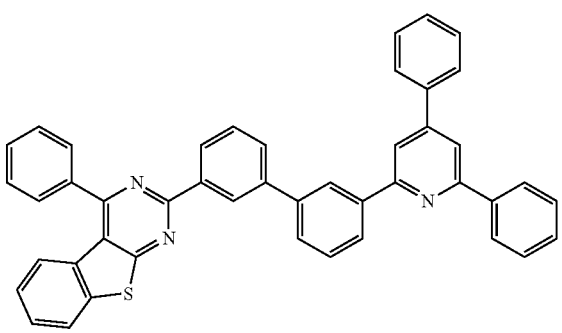
ET-d-15
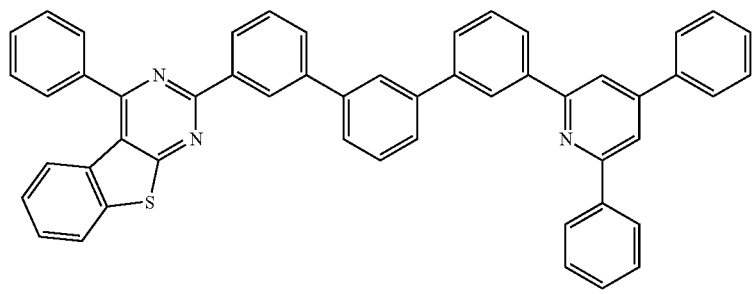
ET-d-16
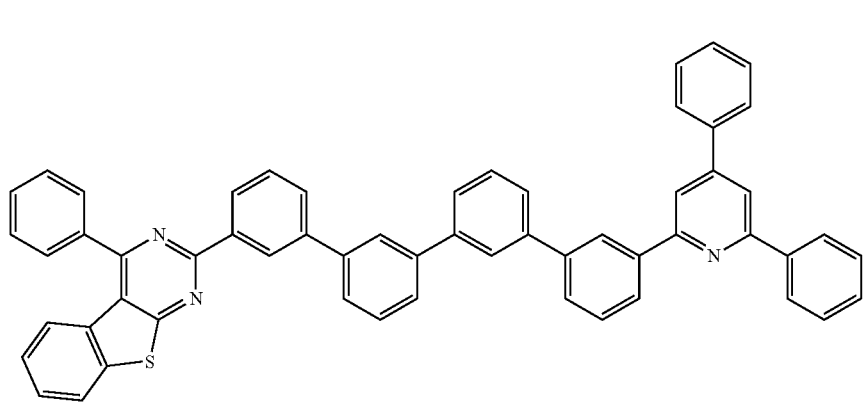

ET-d-17

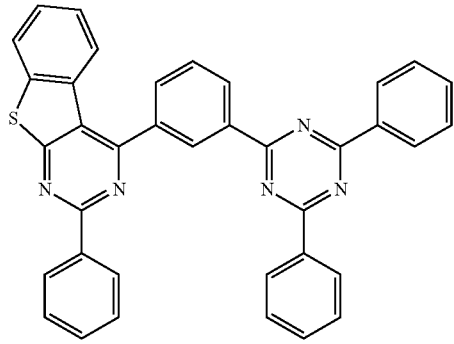

ET-d-18

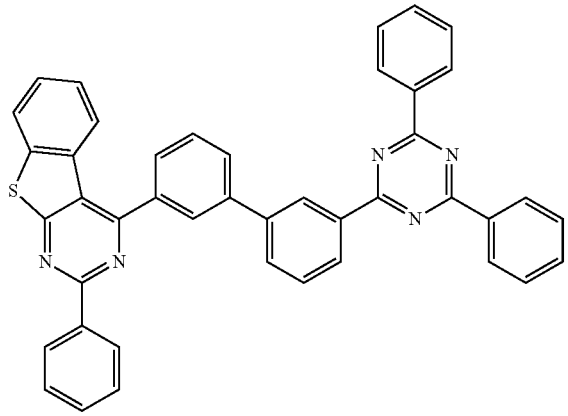

ET-d-19

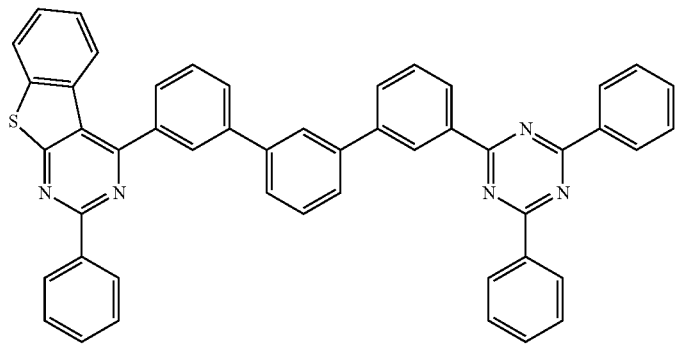

ET-d-20

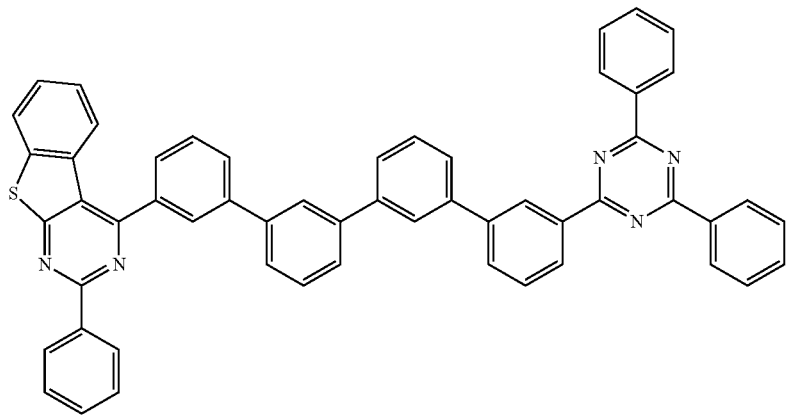

The first host compound and the second host compound may variously be combined to prepare various compositions.

For example, a composition according to an example embodiment may include a compound represented by one of Chemical Formula C2, Chemical Formula C3, Chemical Formula C4, Chemical Formula E1, Chemical Formula E2, Chemical Formula E3, Chemical Formula E4, and Chemical Formula F as a first host and a compound represented by Chemical Formula 3-I as a second host.

Herein, the $Ar^1$ to $Ar^3$ may independently be a substituted or unsubstituted phenyl group, a substituted or unsubstituted biphenyl group, a substituted or unsubstituted terphenyl group, a substituted or unsubstituted naphthyl group, or a substituted or unsubstituted triphenylene group, $L^1$ may independently be a single bond, a substituted or unsubstituted phenylene group, or a substituted or unsubstituted biphenylene group, and $R^1$ to $R^3$ and $R^6$ to $R^{11}$ may independently be hydrogen, deuterium, a substituted or unsubstituted C1 to C4 alkyl group, a substituted or unsubstituted phenyl group, or a combination thereof, and the $L^2$ and $L^3$ may independently be a single bond, a substituted or unsubstituted phenylene group, a substituted or unsubstituted biphenylene group, a substituted or unsubstituted terphenylene group, or a substituted or unsubstituted quaterphenylene group, the ET may be a substituted or unsubstituted pyridyl group, a substituted or unsubstituted pyrimidinyl group, a substituted or unsubstituted triazinyl group, or a substituted or unsubstituted quinazolyl group, the $Y^2$ may be a substituted or unsubstituted phenyl group, a substituted or unsubstituted biphenyl group, or a substituted or unsubstituted terphenyl group, and the $R^4$ and $R^5$ may independently be hydrogen, deuterium, a substituted or unsubstituted C1 to C4 alkyl group, a substituted or unsubstituted phenyl group, or a combination thereof.

More specifically, the first host compound may be represented by one of Chemical Formula C4, Chemical Formula C2, Chemical Formula E1, and Chemical Formula E2.

As described above, the first host compound is a compound having relatively strong hole transport characteristics and the second host compound is a compound having relatively strong electron transport characteristics, and thus improve luminous efficiency due to increased mobility of electrons and holes when they are used together compared with the compounds alone.

When a material having biased electron or hole characteristics is used to form a light emitting layer, excitons in a device including the light emitting layer are relatively more generated due to recombination of carriers on the interface between a light emitting layer and an electron transport layer or a hole transport layer. As a result, the molecular excitons in the light emitting layer interact with charges on the interface of the transport layers and thus, cause a roll-off of sharply deteriorating efficiency and also, sharply deteriorate light emitting life-span characteristics. In order to solve the problems, the first and second hosts are simultaneously included in the light emitting layer to make a light emitting region not be biased to either of the electron transport layer or the hole transport layer and a device capable of adjusting carrier balance in the light emitting layer may be provided and thereby light emitting life-span may be improved and life-span characteristics may be remarkably improved.

The first host compound and the second host compound may be for example included in a weight ratio of about 1:10 to about 10:1. In addition, in one example of the present disclosure, they may be included in a weight ratio of about 2:8 to about 8:2, about 3:7 to about 7:3, about 4:6 to about 6:4, or about 7:3 to about 5:5, and may be for example included in a weight ratio of about 5:5 or about 7:3. Within the ranges, bipolar characteristics may be effectively realized to improve efficiency and life-span simultaneously.

The composition may further include at least one compound in addition to the first host compound and the second host compound.

The composition may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

The composition may be formed using a dry film formation method or a solution process.

Hereinafter, an organic optoelectronic device according to another embodiment is described.

An organic optoelectronic device according to another embodiment includes an anode and a cathode facing each other and at least one organic layer disposed between the anode and the cathode, wherein the organic layer includes the composition for an organic optoelectronic device.

Herein, an organic light emitting diode as one example of an organic optoelectronic device is described referring to drawings.

Figure 2:
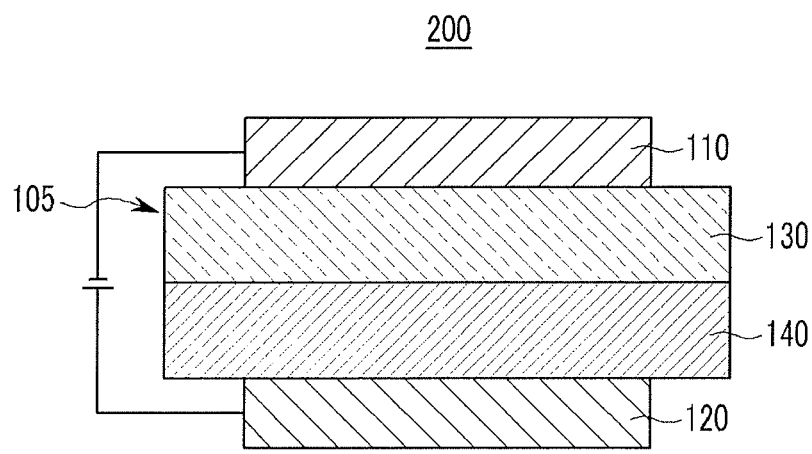

FIGS. 1 and 2 are cross-sectional views of organic light emitting diodes according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide, and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide, and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 includes a light emitting layer 130 including the composition as a host of the light emitting layer.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be for example a hole transport layer, a hole injection layer, and/or an electron blocking layer, and may include at least one layer.

In an embodiment, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. These examples, however, are not in any sense to be interpreted as limiting the scope of the invention.

(Preparation of Composition for Organic Optoelectronic Device)

Hereinafter, starting materials and reactants used in Examples and Synthesis Examples were purchased from Sigma-Aldrich Co. Ltd. or TCI Inc. as far as there in no particular comment and may be easily synthesized as publicly known materials.

In the following Synthesis Examples, when "'B' is used instead of 'A'", the amounts of 'A' and 'B' are the same as based on a mole equivalent.

As specific examples of the compound for an organic optoelectronic device of the present disclosure, the compound of Chemical Formula 1 was synthesized by the following reaction schemes.

Synthesis of First Host (HT Host) Compound

[Representative Reaction Scheme]

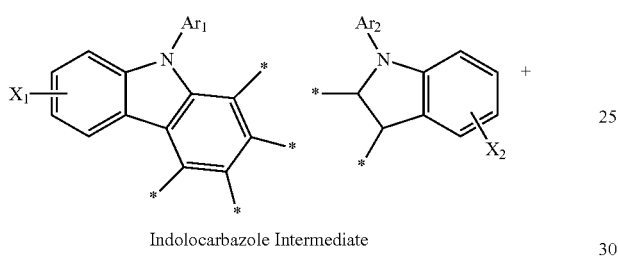

Indolocarbazole Intermediate

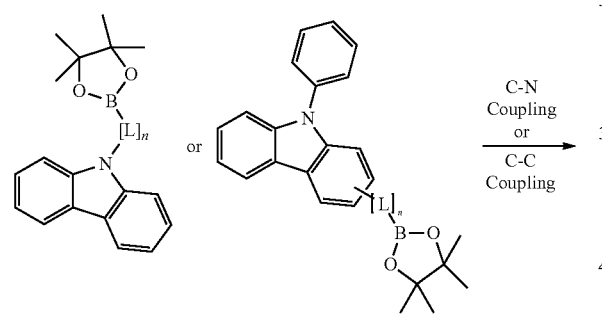

Carbazole Intermediate

HT Host

Ar1 or Ar2: Aryl
X1, X2, X3: Cl or H
L: Aryl
n: 0-1

↵

[Indolocarbazole Intermediate]

Intermediate A

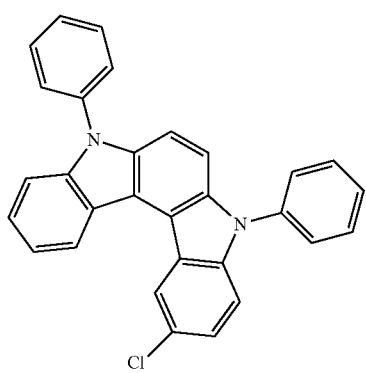

Intermediate B

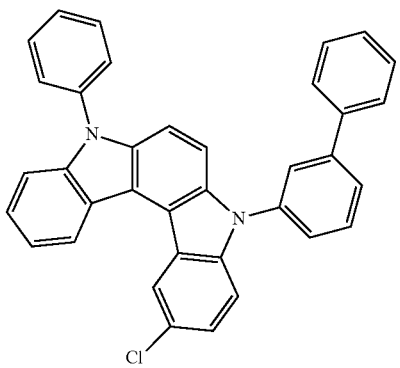

Intermediate C

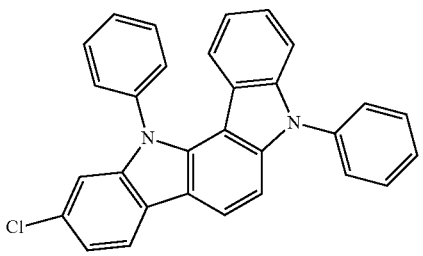

Intermediate D

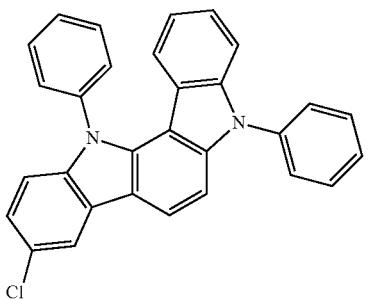

Intermediate E

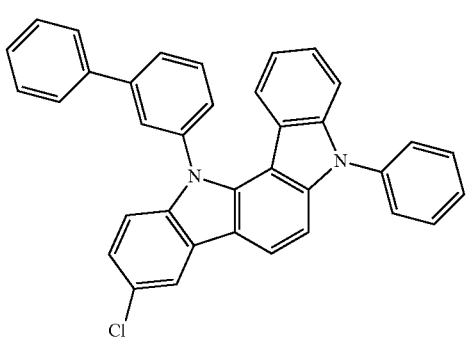

Intermediate F

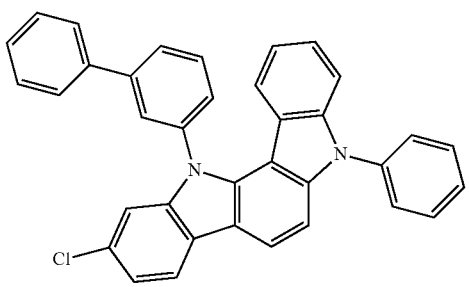

Intermediate G
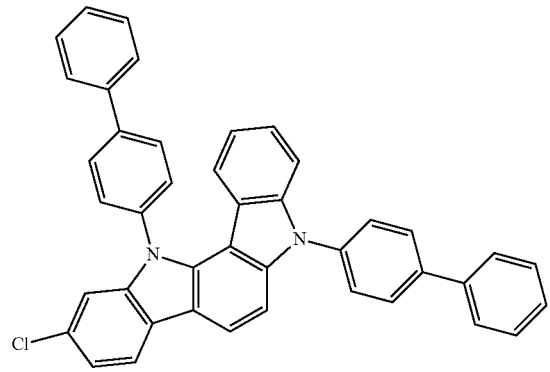
Intermediate K
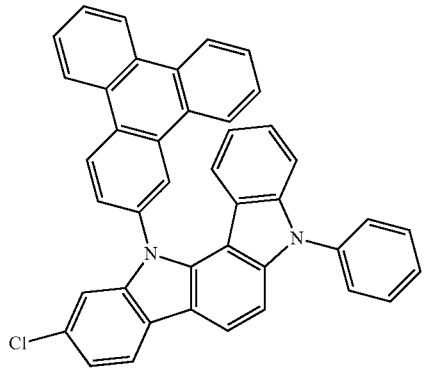
Intermediate H
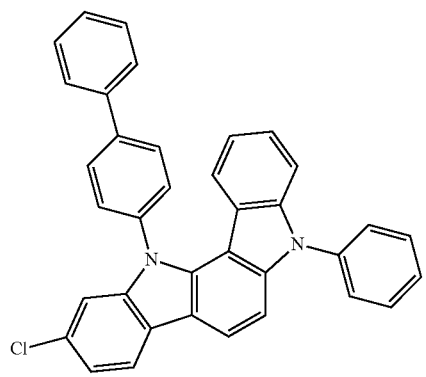
Intermediate L
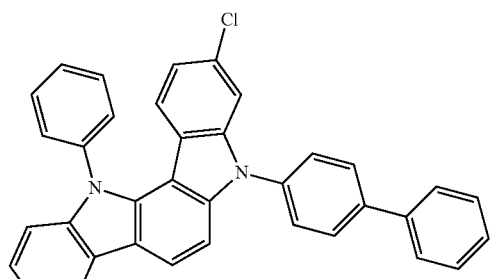
[Carbazole Intermediate]
Intermediate I
Intermediate A
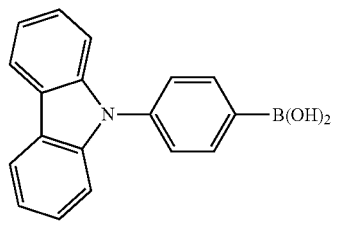
Intermediate B
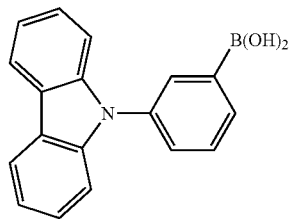
Intermediate J
Intermediate C
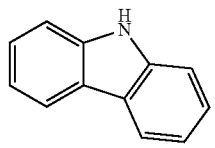

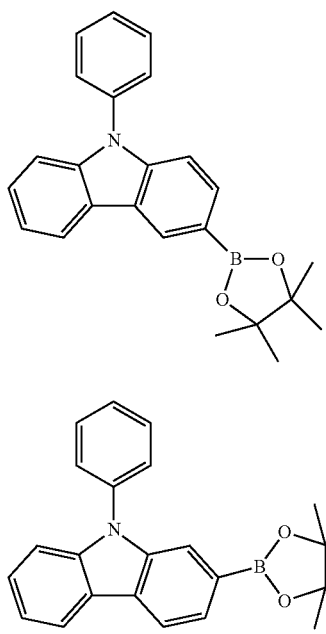

SYNTHESIS EXAMPLE 1

Synthesis of Compound E-03

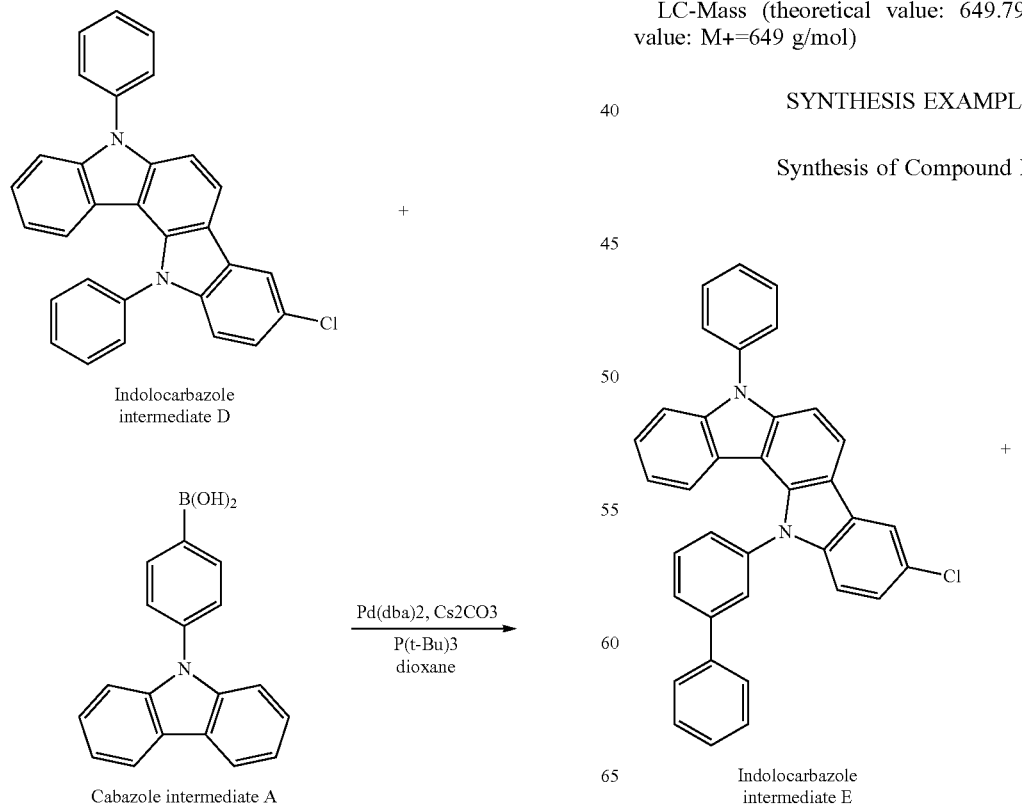

8.3 g (18.74 mmol) of Indolocarbazole Intermediate D, 5.92 g (20.61 mmol) of Carbazole Intermediate A, and 12.21 g (37.48 mmol) of cesium carbonate were put in a round-bottomed flask, and 200 ml of 1,4-dioxane was added thereto to dissolve them. 0.32 g (0.56 mmol) of Pd(dba)$_2$ and 0.27 g (1.31 mmol) of tri-tertiary-butylphosphine were sequentially added thereto and the mixture was refluxed and stirred under a nitrogen atmosphere for 12 hours. When a reaction was complete, 200 ml of distilled water was added thereto, and a solid produced therein was filtered and washed with distilled water and methanol. The solid was heated and stirred with 200 ml of toluene, silica gel-filtered, concentrated, and recrystallized in toluene to obtain a target compound, Compound E-03 (5.9 g, 48%).

LC-Mass (theoretical value: 649.79 g/mol, measured value: M+=649 g/mol)

SYNTHESIS EXAMPLE 2

Synthesis of Compound E-13

-continued

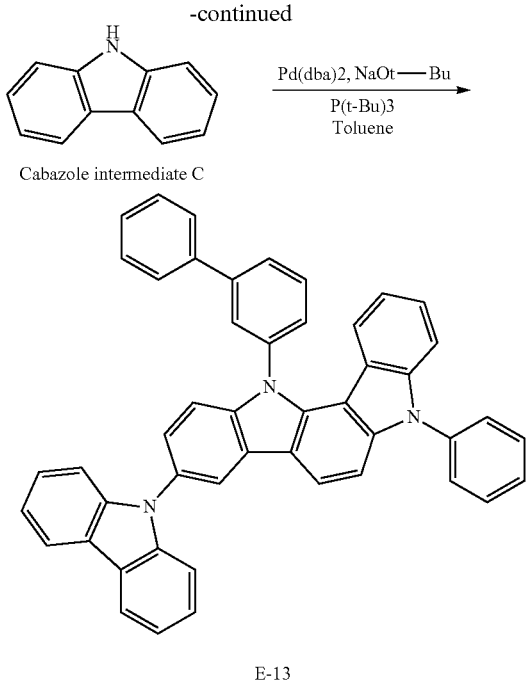

10.92 g (21.03 mmol) of Indolocarbazole Intermediate E, 3.69 g (22.09 mmol) of Carbazole Intermediate C, and 4.04 g (42.08 mmol) of sodium t-butoxide were put in a round-bottomed flask, and 200 ml of toluene was added thereto to dissolve them. 0.6 g (1.05 mmol) of Pd(dba)$_2$ and 0.43 g (0.21 mmol) of tri-tertiary-butylphosphine were sequentially added thereto, and the mixture was refluxed and stirred under a nitrogen atmosphere for 12 hours. When a reaction was complete, 400 ml of methanol was added thereto, and a solid produced after stirring the obtained mixture for 1 hour was filtered. The solid was heated and dissolved in toluene, silica gel-filtered, and recrystallized with acetone to obtain a target compound, Compound E-13 (8.64 g, 63%).

LC-Mass (theoretical value: 649.78 g/mol, measured value: M+=649 g/mol)

SYNTHESIS EXAMPLES 3 to 19

Compounds according to Synthesis Examples 3 to 19 were synthesized according to the same method as Synthesis Examples 1 and 2 by changing each corresponding indolo-carbazole intermediates and carbazole intermediates.

Intermediates used in Synthesis Examples 3 to 19 and yield amounts, yields, and LC/MS analysis results are shown in Table 1.

TABLE 1

| Synthesis Examples | Indolo carbazole intermediate | Carbazole intermediate | HT-Host | Amount (Yield) | LC/MS M+ = g/mol |
|---|---|---|---|---|---|
| Synthesis Example 3 | A | D | C-01 | 9.5 g (65%) | 649 |
| Synthesis Example 4 | A | A | C-09 | 10.1 g (69%) | 649 |
| Synthesis Example 5 | A | B | C-10 | 9.3 g (63%) | 649 |
| Synthesis Example 6 | B | C | C-08 | 10.5 g (71%) | 649 |
| Synthesis Example 7 | A | E | C-02 | 9.1 g (62%) | 649 |
| Synthesis Example 8 | C | A | E-01 | 6.5 g (44%) | 649 |
| Synthesis Example 9 | C | B | E-02 | 6.2 g (42%) | 649 |
| Synthesis Example 10 | D | B | E-04 | 7.5 g (51%) | 649 |
| Synthesis Example 11 | D | E | E-06 | 7.1 g (48%) | 649 |
| Synthesis Example 12 | F | C | E-12 | 8.7 g (59%) | 649 |
| Synthesis Example 13 | D | D | E-05 | 7.2 g (49%) | 649 |
| Synthesis Example 14 | G | C | E-14 | 10.1 g (62%) | 725 |
| Synthesis Example 15 | H | C | E-15 | 8.1 g (55%) | 649 |
| Synthesis Example 16 | I | C | E-16 | 7.9 g (54%) | 649 |
| Synthesis Example 17 | J | C | E-17 | 9.9 g (61%) | 725 |
| Synthesis Example 18 | K | C | E-18 | 10.5 g (64%) | 723 |
| Synthesis Example 19 | L | C | F-1 | 8.4 g (57%) | 649 |

Synthesis of Second Host (ET Host) Compound

SYNTHESIS EXAMPLE 20

Synthesis of Compound ET-b-2

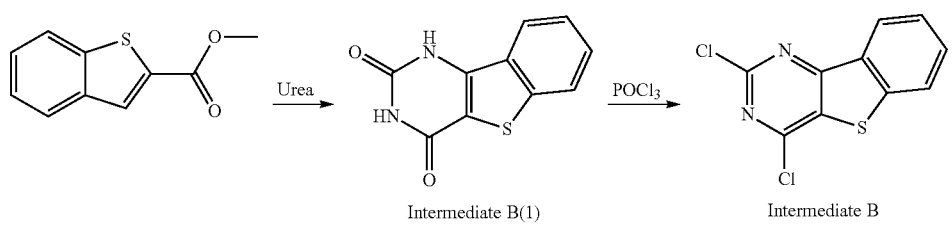

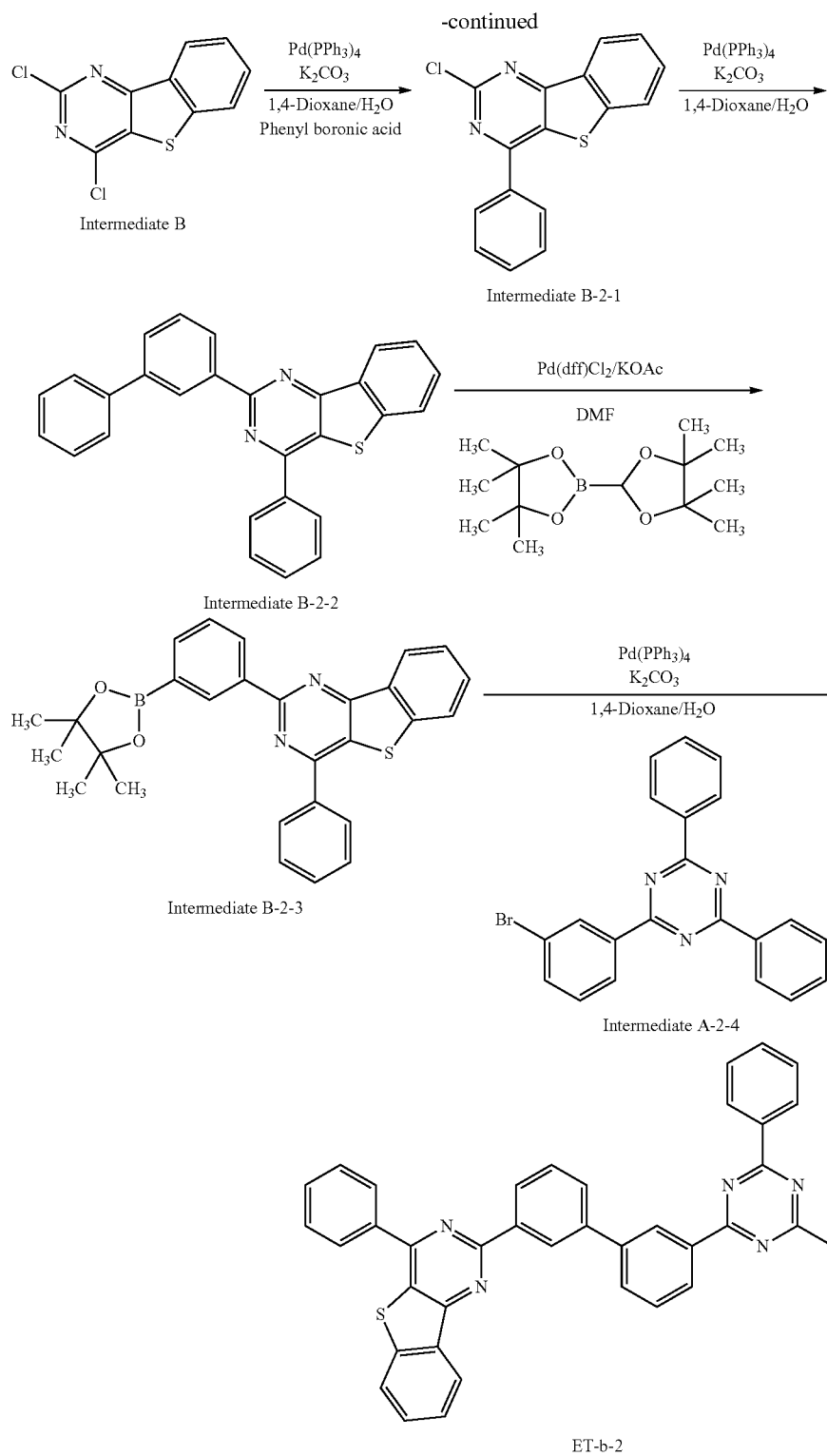

Synthesis of Intermediate B(1) (benzo-1H-thieno [3,2-d] pyrimidine-2,4-dione)

A mixture of methyl 3-amino-benzo-2-thiophenecarboxylate (237.5 g, 1.15 mol) and urea (397.0 g, 5.75 mol) was stirred at 200° C. for 2 hours in a 2 L round flask. The reaction mixture at the high temperature was cooled down to room temperature, poured into a sodium hydroxide solution, filtered to remove impurities, and acidized (HCl, 2N), and a precipitate obtained therefrom was dried to obtain Intermediate B(1) (175 g, 75%).

calcd. $C_{10}H_6N_2O_2S$: C, 55.04; H, 2.77; N, 12.84; O, 14.66; S, 14.69; found: C, 55.01; H, 2.79; N, 12.81; O, 14.69; S, 14.70.

Synthesis of Intermediate B (benzo-2,4-dichloro-thieno[3,2-d]pyrimidine)

A mixture of Intermediate B(1) (benzo-1H-thieno[3,2-d]pyrimidine-2,4-dione, 175 g, 0.80 mol) and 1000 mL of phosphorous oxychloride was stirred and refluxed for 8 hours in a 3000 mL round flask. The reaction mixture was cooled down room temperature and then, poured into ice/water while fervently stirred to produce a precipitate. The obtained reactant was filtered to obtain Intermediate B (white solid benzo-2,4-dichloro-thieno[3,2-d]pyrimidine, 175 g, 85%). An elemental analysis result of Intermediate B is as follows.

calcd. $C_{10}H_4Cl_2N_2S$: C, 47.08; H, 1.58; Cl, 27.79; N, 10.98; S, 12.57; found: C, 47.03; H, 1.61; Cl, 27.81; N, 10.98; S, 12.60.

Synthesis of Intermediate B-2-1

70.0 g (274.4 mmol) of Intermediate B, 33.5 g (274.4 mmol) of phenylboronic acid, 94.8 g (686.0 mmol) of potassium carbonate, and 15.9 g (13.7 mmol) of tetrakis(triphenylphosphine) palladium (0) were added to 800 mL of 1,4-dioxane and 400 mL of water in a 2000 mL flask, and the mixture was heated under a nitrogen flow for 24 hours at 50° C. The obtained mixture was added to 3000 mL of methanol, and a solid crystallized therein was filtered, dissolved in monochlorobenzene, filtered with silica gel/Celite, and then, recrystallized with methanol after removing an appropriate amount of an organic solvent to obtain Intermediate B-2-1 (59.4 g, yield of 73%).

calcd. C16H9ClN2S: C, 64.75; H, 3.06; Cl, 11.95; N, 9.44; S, 10.80; found: C, 64.70; H, 3.02; Cl, 11.93; N, 9.40; S, 10.73.

Synthesis of Intermediate B-2-2

59.0 g (198.8 mmol) of Intermediate B-2-1, 31.1 g (198.8 mmol) of 3-chlorophenyl boronic acid, 68.7 g (497.0 mmol) of potassium carbonate, and 11.5 g (9.9 mmol) of tetrakis(triphenylphosphine) palladium (0) were added to 600 mL of 1,4-dioxane and 300 mL of water in a 2 L round flask, and the mixture was heated and refluxed under a nitrogen flow for 16 hours. The obtained mixture was added to 2000 mL of methanol, and a solid crystallized therein was filtered, dissolved in monochlorobenzene, filtered with silica gel/Celite, and then, after removing an appropriate amount of an organic solvent, recrystallized with methanol to obtain Intermediate B-2-2 (51.2 g, yield of 69%).

calcd. C22H13ClN2S: C, 70.87; H, 3.51; Cl, 9.51; N, 7.51; S, 8.60; found C, 70.84; H, 3.46; Cl, 9.50; N, 7.47; S, 8.58.

Synthesis of Intermediate B-2-3

Intermediate B-2-2 (50.0 g, 134.1 mmol), 4,4,4',4',5,5,5',5'-octamethyl-2,2'-bi(1,3,2-dioxaborolane) (40.9 g, 160.9 mmol), potassium acetate (KOAc, 39.5 g, 402.3 mmol), and 1,1'-bis(diphenylphosphino) ferrocene-palladium (II) dichloride (6.6 g, 8.1 mmol), and tricyclohexylphosphine (5.6 g, 20.1 mmol) were added to 500 mL of N,N-dimethylformamide in a 1 L flask, and the mixture was stirred at 130° C. for 24 hours. When a reaction was complete, a reaction solution was treated with water and EA for an extraction, and an organic layer obtained therefrom was treated with magnesium sulfate to remove moisture, concentrated, and purified through column chromatography to obtain Intermediate B-2-3 as a white solid (40.3 g, yield of 69%).

calcd. C28H25BN2O2S: C, 72.42; H, 5.43; B, 2.33; N, 6.03; 0, 6.89; S, 6.90; found: C, 72.40; H, 5.42; B, 2.32; N, 6.00; 0, 6.82; S, 6.85.

Synthesis of Compound ET-b-2

Intermediate B-2-3 (5.0 g, 10.8 mmol), Intermediate A-2-4 (4.2 g, 10.8 mmol), potassium carbonate (3.7 g, 27.0 mmol), and tetrakis(triphenylphosphine) palladium (0) (0.6 g, 0.5 mmol) were added to 40 mL of 1,4-dioxane and 20 mL of water in a 100 mL flask, and the mixture was heated and refluxed under a nitrogen flow for 16 hours. The obtained mixture was added to 150 mL of methanol, and a solid crystallized therein was filtered, dissolved in monochlorobenzene, filtered through silica gel/Celite, and then, after removing an appropriate amount of an organic solvent, recrystallized with methanol to obtain Compound ET-b-2 (4.7 g, yield of 68%).

calcd. C43H27N5S: C, 79.98; H, 4.21; N, 10.84; S, 4.97; found: C, 79.95; H, 4.20; N, 10.81; S, 4.92.

SYNTHESIS EXAMPLE 21

Synthesis of Compound ET-b-46

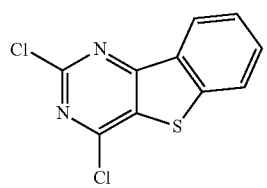

Intermediate B

Pd(PPh3)4
K2CO3
————————→
1,4-Dioxane/H2O

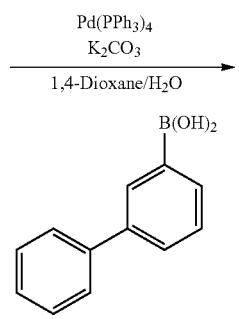

B(OH)2

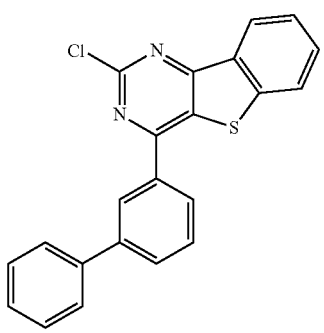

Intermediate B-3-2

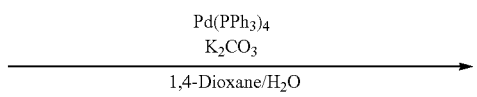

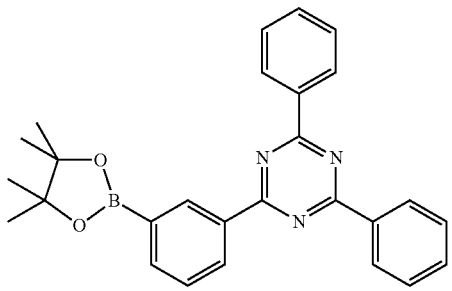

Intermediate B-3-3

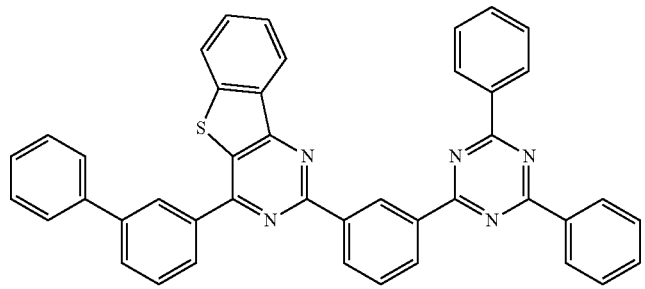

Compound ET-b-46

Synthesis of Intermediate B-3-2

Intermediate B (10.0 g, 39.2 mmol), 3-biphenyl boronic acid (12.1 g, 43.1 mmol), potassium carbonate (13.5 g, 98.0 mmol) and tetrakis(triphenylphosphine) palladium (0) (2.3 g, 43.1 mmol) were added to 140 mL of 1,4-dioxane and 70 mL of water in a 500 mL flask, and the mixture was heated under a nitrogen flow for 12 hours at 60° C. The obtained mixture was added to 500 mL of methanol, and a solid crystallized therein was filtered, dissolved in monochlorobenzene, filtered through silica gel/Celite, and then, after removing appropriate amount of an organic solvent, recrystallized with methanol to obtain Intermediate B-3-2 (10.1 g, yield of 69%).

calcd. C22H13ClN2S: C, 70.87; H, 3.51; Cl, 9.51; N, 7.51; S, 8.60; found: C, 70.80; H, 3.50; Cl, 9.47; N, 7.49; S, 8.60.

Synthesis of Intermediate B-3-3

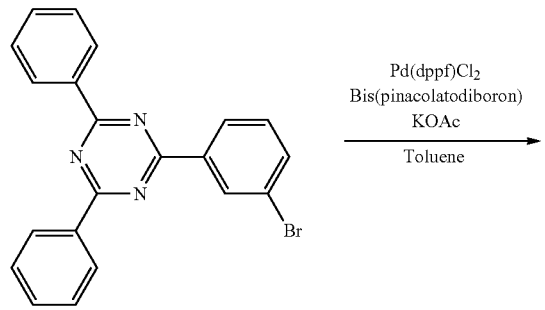

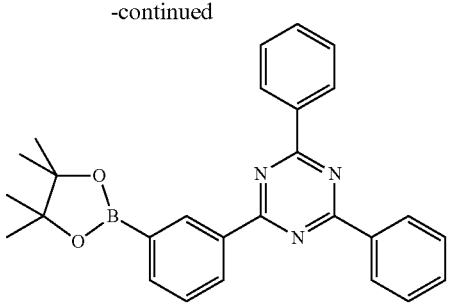

B-3-3

2-(3-bromophenyl)-4,5-diphenyl-1,3,5-triazine (20 g, 51.51 mmol) was dissolved in 250 mL of toluene in a 500 mL round-bottomed flask. 0.05 equivalent of dichlorodiphenyl phosphinoferrocene palladium, 1.2 equivalent of bis (pinacolato)diboron, and 2 equivalents of potassium acetate were added thereto, and the mixture was heated and refluxed under a nitrogen atmosphere for 18 hours. The reaction solution was cooled down, and 100 mL of water was added thereto to extract an organic layer. The organic layer was collected, and then, a solution obtained through silica gel filtration after treating activated carbon was concentrated. The concentrated residue was collected and crystallized in 200 mL of toluene and 50 mL of acetone to obtain 19.1 g of Intermediate B-3-3.

Synthesis of Compound ET-b-46

Intermediate B-3-2 (10.0 g, 26.8 mmol), Intermediate B-3-3 (11.7 g, 26.8 mmol), potassium carbonate (9.3 g, 67.1 mmol), and tetrakis(triphenylphosphine) palladium (0) (1.6 g, 1.3 mmol) were added to 90 mL of 1,4-dioxane and 45 mL of water in a 250 mL flask, and the mixture was heated under a nitrogen flow for 12 hours at 70° C. The obtained mixture was added to 250 mL of methanol, and a solid crystallized therein was dissolved in 1,2-dichlorobenzene, filtered through silica gel/Celite, and then, after removing an appropriate amount of an organic solvent, was recrystallized with methanol to obtain Compound ET-b-46 (12.4 g, yield of 72%).

calcd. C43H27N5S: C, 79.98; H, 4.21; N, 10.84; S, 4.97; found: C, 79.97; H, 4.19; N, 10.81; S, 4.96.

Manufacture of Organic Light Emitting Diode

EXAMPLE 1

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing N4,N4'-diphenyl-N4,N4'-bis (9-phenyl-9H-carbazol-3-yl)biphenyl-4,4'-diamine (Compound A), and a hole transport layer was formed by depositing 1,4,5,8,9,11-hexaazatriphenylene-hexacarbonitrile (HAT-CN) (Compound B) in a thickness of 50 Å on the injection layer, and depositing N-(biphenyl-4-yl)-9,9-dimethyl-N-(4-(9-phenyl-9H-carbazol-3-yl)phenyl)-9H-fluoren-2-amine (Compound C) in a thickness of 1020 Å. On the hole transport layer, a 400 Å-thick light emitting layer was formed by vacuum-depositing Compound C-01 and Compound ET-b-2 as a host and tris(4-methyl-2,5-diphenylpyridine)iridium (III) (Compound D) as a dopant in a doping amount of 10 wt %

Herein, Compound C-01 and Compound ET-b-2 were used in a ratio of 5:5.

Subsequently, a 300 Å-thick electron transport layer was formed by vacuum-depositing 8-(4-(4-(naphthalen-2-yl)-6-(naphthalen-3-yl)-1,3,5-triazin-2-yl)phenyl)quinoline (Compound E) and Liq simultaneously in a 1:1 ratio on the light emitting layer, and Liq (15 Å) and Al (1200 Å) were sequentially vacuum-deposited on the electron transport layer to form a cathode, manufacturing an organic light emitting diode.

The organic light emitting diode has five organic thin layers, specifically
a structure of ITO/A 700 Å/B 50 Å/C1020 Å/EML[C-01: ET-b-2:D=X:X:10%] 400 Å/E:Liq 300 Å/Liq 15 Å/Al 1200 Å.

(X=a weight ratio)

EXAMPLES 2 TO 20

Organic light emitting diodes according to Examples 2 to 20 were manufactured according to the same method as Example 1 by changing the first host and the second host, and a mixing ratio thereof as shown in Table 2.

COMPARATIVE EXAMPLES 1 AND 2

Organic light emitting diodes according to Comparative Examples 1 and 2 were manufactured according to the same method as Example 1 except for not using the second host and using the first hosts C-01 and E-01 alone as shown in Table 2.

COMPARATIVE EXAMPLES 3 AND 4

Organic light emitting diodes according to Comparative Examples 3 and 4 were manufactured according to the same method as Example 1 except for not using the first host and using the second hosts ET-b-2 and ET-b-46 alone as shown in Table 2.

COMPARATIVE EXAMPLE 5

An organic light emitting diodes according to Comparative Example 5 was manufactured according to the same method as Example 1 except for not using the first host and the second host and using CBP alone as shown in Table 2.

Evaluation

Luminous efficiency and life-span characteristics of each of the organic light emitting diodes according to Examples 1 to 20 and Comparative Examples 1 to 5 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-span was obtained by measuring time taken until current efficiency (cd/A) decreased down to 90% while current efficiency (cd/A) was maintained at 6000 cd/m$^2$.

TABLE 2

| | First host | Second host | First host:Second host (wt/wt) | Driving voltage (V) | Luminous efficiency (cd/A) | Life-span T90 (h) |
|---|---|---|---|---|---|---|
| Example 1 | C-01 | ET-b-2 | 5:5 | 3.75 | 64.9 | 154 |
| Example 2 | C-01 | ET-b-2 | 7:3 | 3.83 | 67.3 | 186 |
| Example 3 | C-01 | ET-b-46 | 5:5 | 3.61 | 65.7 | 162 |
| Example 4 | C-01 | ET-b-46 | 7:3 | 3.76 | 68.7 | 190 |
| Example 5 | C-09 | ET-b-2 | 5:5 | 4.17 | 70.3 | 152 |
| Example 6 | C-09 | ET-b-2 | 7:3 | 4.24 | 67.1 | 184 |
| Example 7 | C-09 | ET-b-46 | 5:5 | 3.53 | 68.6 | 140 |
| Example 8 | C-09 | ET-b-46 | 7:3 | 4.00 | 66.3 | 162 |
| Example 9 | E-01 | ET-b-2 | 5:5 | 3.53 | 71.4 | 136 |
| Example 10 | E-01 | ET-b-2 | 7:3 | 3.64 | 70.0 | 180 |
| Example 11 | E-01 | ET-b-46 | 5:5 | 3.70 | 67.4 | 160 |
| Example 12 | E-01 | ET-b-46 | 7:3 | 3.80 | 66.4 | 193 |
| Example 13 | E-03 | ET-b-2 | 5:5 | 3.79 | 67.2 | 180 |
| Example 14 | E-03 | ET-b-2 | 7:3 | 3.94 | 69.2 | 186 |
| Example 15 | E-03 | ET-b-46 | 5:5 | 3.76 | 68.6 | 138 |
| Example 16 | E-03 | ET-b-46 | 7:3 | 3.86 | 70.2 | 164 |
| Example 17 | E-13 | ET-b-2 | 5:5 | 3.55 | 68.2 | 154 |
| Example 18 | E-13 | ET-b-2 | 7:3 | 3.66 | 69.4 | 188 |
| Example 19 | E-13 | ET-b-46 | 5:5 | 3.52 | 68.7 | 161 |

TABLE 2-continued

| | First host | Second host | First host:Second host (wt/wt) | Driving voltage (V) | Luminous efficiency (cd/A) | Life-span T90 (h) |
|---|---|---|---|---|---|---|
| Example 20 | E-13 | ET-b-46 | 7:3 | 3.83 | 70.3 | 183 |
| Comparative Example 1 | | C-01 | — | 7.21 | 4.0 | 5 |
| Comparative Example 2 | | E-01 | — | 7.68 | 4.6 | 3 |
| Comparative Example 3 | | ET-b-2 | — | 4.51 | 59.6 | 50 |
| Comparative Example 4 | | ET-b-46 | — | 6.45 | 50.6 | 75 |
| Comparative Example 5 | | CBP | — | 7.20 | 19.5 | 1 |

Referring to Table 2, the organic light emitting diodes according to Examples 1 to 20 showed remarkably improved driving voltage, luminous efficiency, and life-span characteristics compared with the organic light emitting diodes according to Comparative Examples 1 to 4 using comparative materials alone and the organic light emitting diode according to Comparative Example 5 using CBP.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present disclosure in any way.

DESCRIPTION OF SYMBOLS

100, 200: organic light emitting diode
105: organic layer
110: cathode
120: anode
130: light emitting layer
140: hole auxiliary layer

What is claimed is:

1. A composition for an organic optoelectronic device, the composition comprising:
   at least one of a first host compound represented by a combination of Chemical Formula 1 and Chemical Formula 2, and
   at least one of a second host compound represented by a combination of Chemical Formula 3 and Chemical Formula 4:

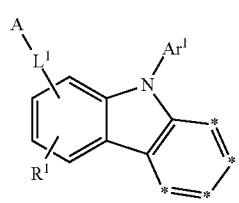

[Chemical Formula 1]

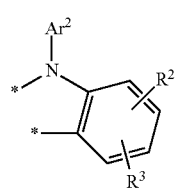

[Chemical Formula 2]

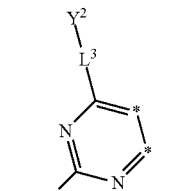

[Chemical Formula 3]

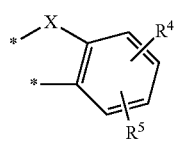

[Chemical Formula 4]

wherein, in Chemical Formulae 1 to 4,
two adjacent *'s of Chemical Formula 1 are bound to two adjacent *'s of Chemical Formula 2 and the remainder *'s of Chemical Formula 1 not being bound to *'s of Chemical Formula 2 are $CR^a$,
two adjacent *'s of Chemical Formula 3 are bound to two *'s of Chemical Formula 4,
the substituent A is a substituted or unsubstituted carbazolyl group,
$Ar^1$ and $Ar^2$ are independently a substituted or unsubstituted C6 to C30 aryl group,
$L^1$ to $L^3$ are independently a single bond or a substituted or unsubstituted C6 to C30 arylene group, the C6 to C30 arylene group consisting of carbocyclic ring(s),
X is O or S,
$Y^1$ and $Y^2$ are independently deuterium, a substituted or unsubstituted C1 to C10 alkyl group, a substituted or unsubstituted C6 to C30 aryl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group, the C6 to C30 aryl group consisting of carbocyclic ring(s),
at least one of $Y^1$ and $Y^2$ is a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group,
$R^a$ and $R^1$ to $R^5$ are independently hydrogen, deuterium, a substituted or unsubstituted C1 to C10 alkyl group, a substituted or unsubstituted C6 to C20 aryl group, or a combination thereof, the C6 to C20 aryl group consisting of carbocyclic ring(s), and
the "substituted" refers to replacement of at least one hydrogen by deuterium, a C1 to C4 alkyl group, a C6 to C12 aryl group, or a C2 to C20 heterocyclic group.

2. The composition for an organic optoelectronic device as claimed in claim 1, wherein Chemical Formula 1 is represented by Chemical Formula 1-I or Chemical Formula 1-II:

[Chemical Formula 1-I]

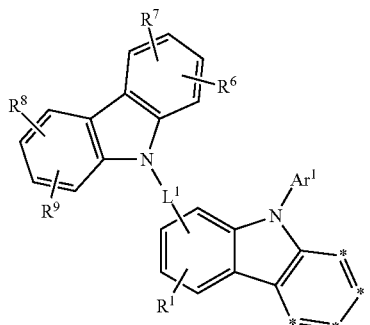

[Chemical Formula 1-II]

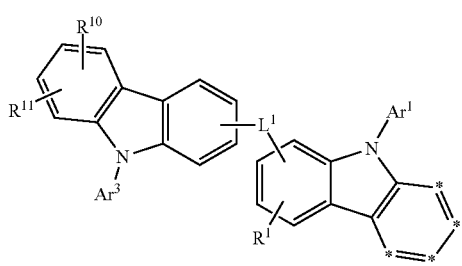

wherein, in Chemical Formulae 1-I and 1-II, two adjacent *'s are bound to two adjacent *'s of Chemical Formula 2 and the remainder *'s not being bound to *'s of Chemical Formula 2 are $CR^a$, $L^1$ is a single bond or a substituted or unsubstituted C6 to C30 arylene group, $Ar^1$ is a substituted or unsubstituted C6 to C30 aryl group, $Ar^3$ is a C6 to C12 aryl group, $R^a$ and $R^1$ are independently hydrogen, deuterium, a substituted or unsubstituted C1 to C4 alkyl group, a substituted or unsubstituted C6 to C12 aryl group, or a combination thereof, and $R^6$ to $R^{11}$ are independently hydrogen, deuterium, a C1 to C4 alkyl group, a C6 to C12 aryl group, or a C2 to C20 heterocyclic group.

3. The composition for an organic optoelectronic device as claimed in claim 1, wherein the first host compound is represented by one of Chemical Formula C, Chemical Formula E, and Chemical Formula F:

[Chemical Formula C]

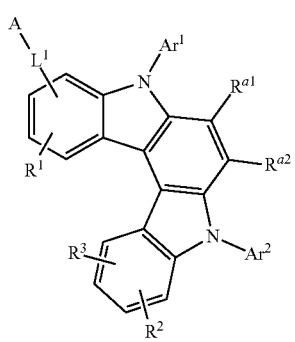

[Chemical Formula E]

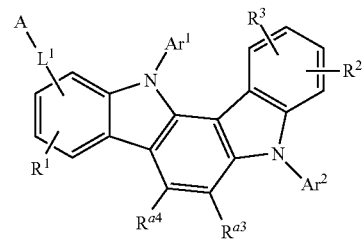

[Chemical Formula F]

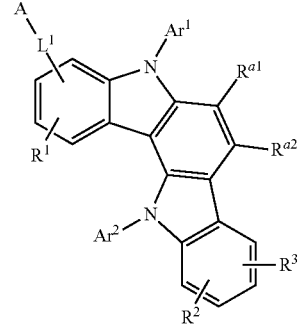

wherein, in Chemical Formula C, Chemical Formula E, and Chemical Formula F, the substituent A is a substituted or unsubstituted carbazolyl group, $Ar^1$ and $Ar^2$ are independently substituted or unsubstituted C6 to C20 aryl group, $L^1$ is a single bond or a substituted or unsubstituted C6 to C20 arylene group, and $R^{a1}$ to $R^{a4}$ and $R^1$ to $R^3$ are independently hydrogen, deuterium, a substituted or unsubstituted C1 to C10 alkyl group, a substituted or unsubstituted C6 to C20 aryl group, or a combination thereof.

4. The composition for an organic optoelectronic device as claimed in claim 3, wherein the first host compound is represented by one of Chemical Formula C1 to Chemical Formula C6, Chemical Formula E1 to Chemical Formula E6, and Chemical Formula F1 to Chemical Formula F6:

[Chemical Formula C1]

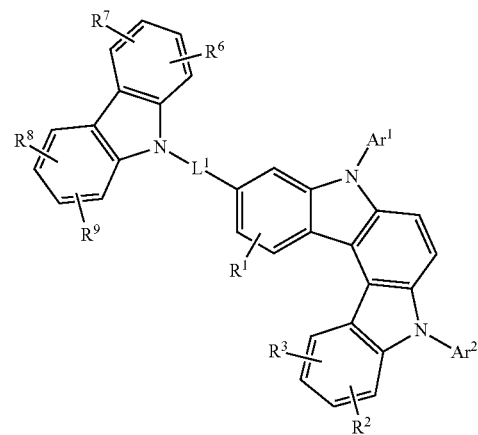

[Chemical Formula C2]
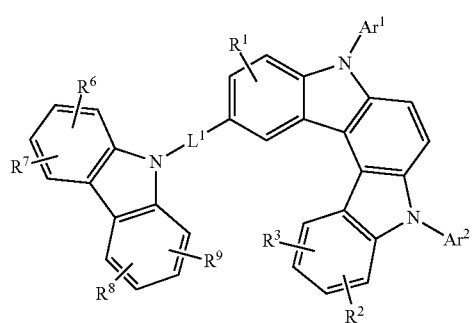
[Chemical Formula C3]
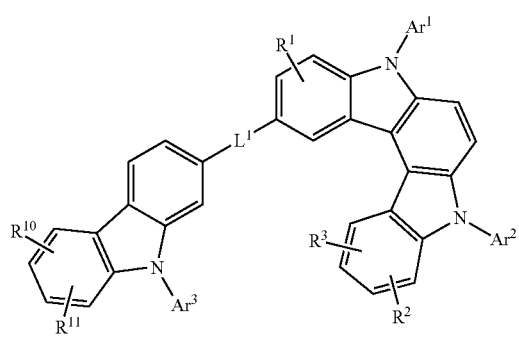
[Chemical Formula C4]
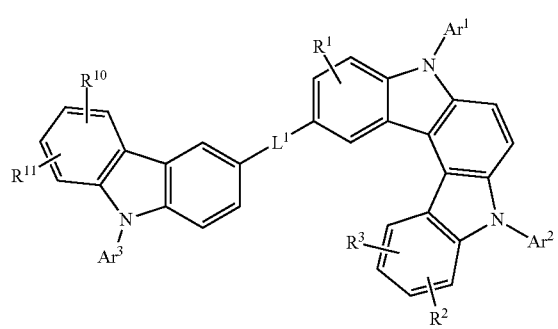
[Chemical Formula C5]
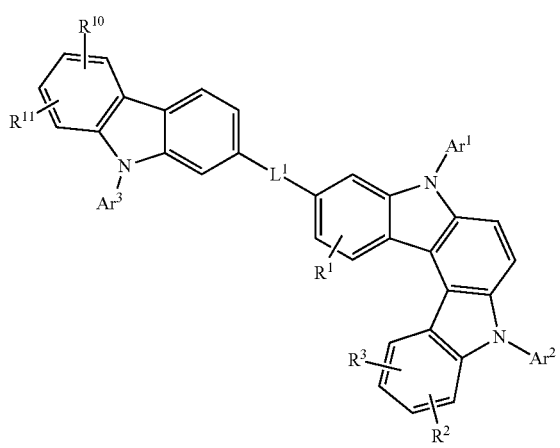
[Chemical Formula C6]
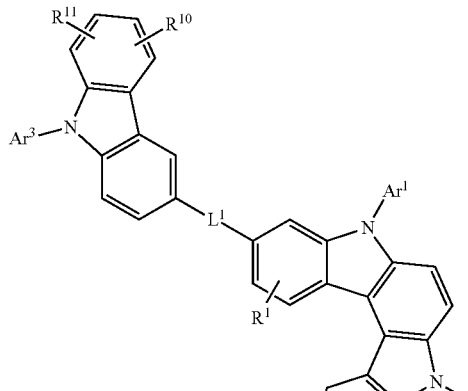
[Chemical Formula E1]
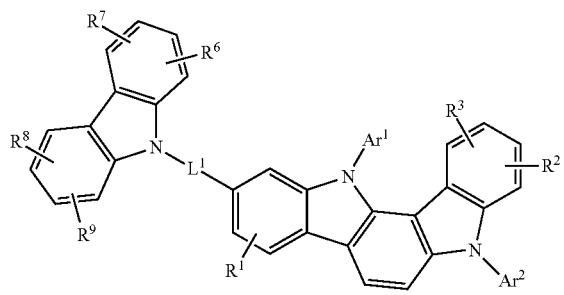
[Chemical Formula E2]
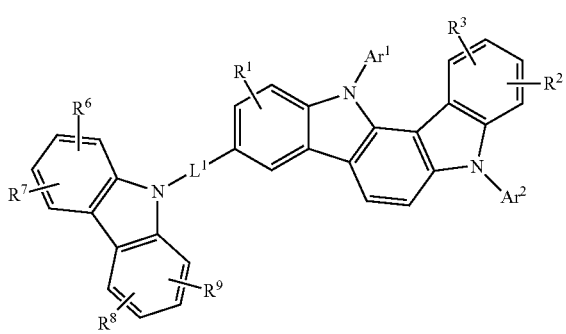
[Chemical Formula E3]

[Chemical Formula E4]
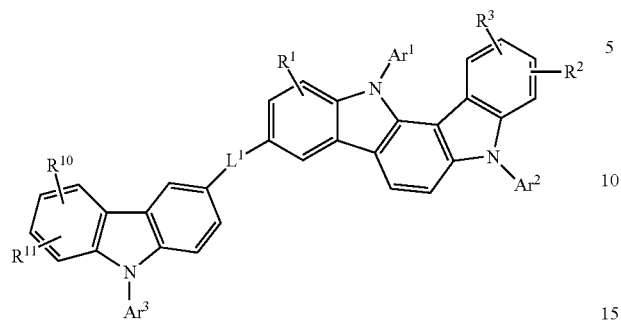
[Chemical Formula E5]
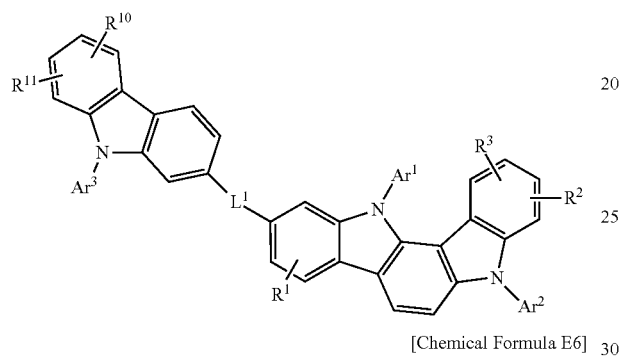
[Chemical Formula E6]
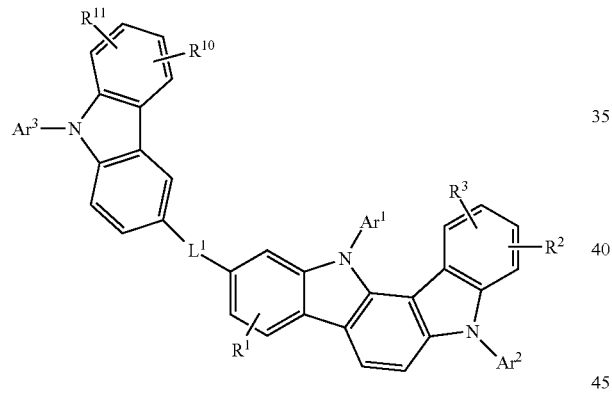
[Chemical Formula F1]
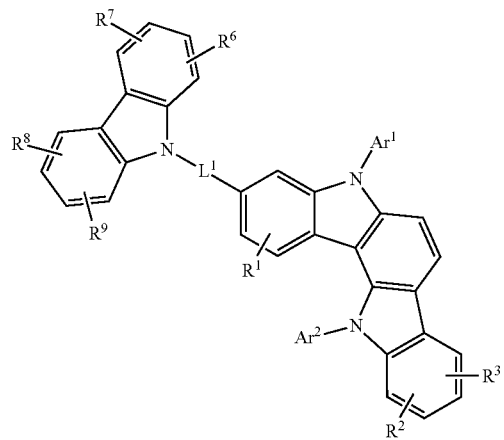
[Chemical Formula F2]
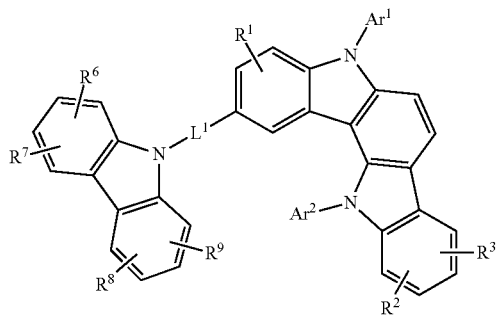
[Chemical Formula F3]
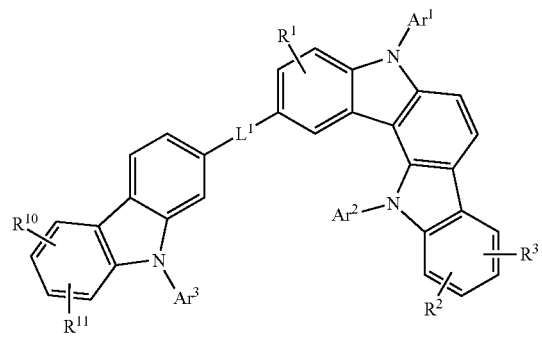
[Chemical Formula F4]
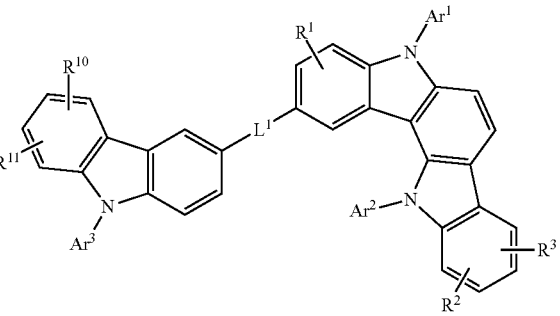
[Chemical Formula F5]
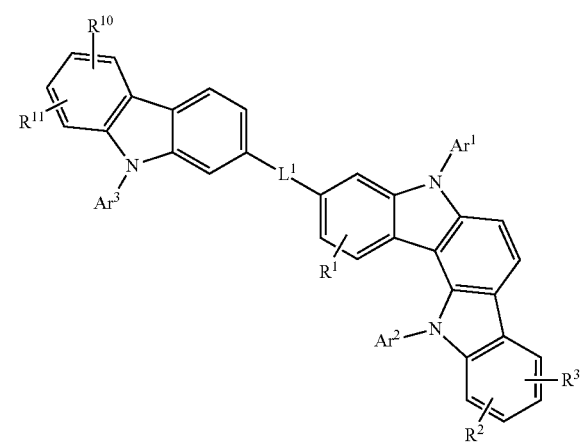

-continued

[Chemical Formula F6]

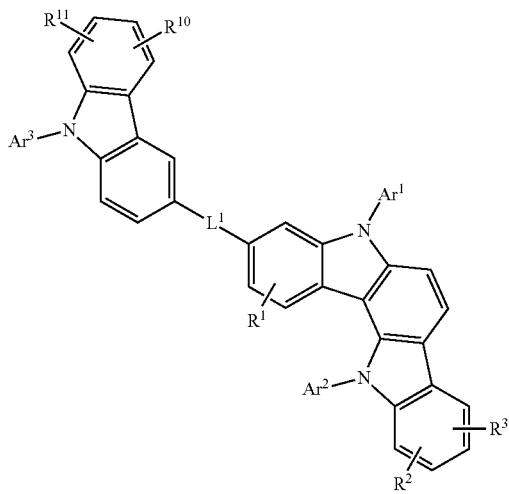

wherein, in Chemical Formula C1 to Chemical Formula C6, Chemical Formula E1 to Chemical Formula E6, and Chemical Formula F1 to Chemical Formula F6, $Ar^1$ and $Ar^2$ are independently substituted or unsubstituted C6 to C20 aryl group, $Ar^3$ is a C6 to C12 aryl group, $L^1$ is a single bond or a substituted or unsubstituted C6 to C20 arylene group, $R^1$ to $R^3$ are independently hydrogen, deuterium, a substituted or unsubstituted C1 to C10 alkyl group, a substituted or unsubstituted C6 to C20 aryl group, or a combination thereof, and $R^6$ to $R^{11}$ are independently hydrogen, deuterium, a C1 to C4 alkyl group, or a C6 to C12 aryl group.

5. The composition for an organic optoelectronic device as claimed in claim 4, wherein:

$Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, or a substituted or unsubstituted triphenylene group, $Ar^3$ is a phenyl group, a biphenyl group, or a napthyl group, $L^1$ is a single bond, a substituted or unsubstituted phenylene group, or a substituted or unsubstituted biphenylene group, $R^1$ to $R^3$ are independently hydrogen, deuterium, a substituted or unsubstituted C1 to C4 alkyl group, a substituted or unsubstituted phenyl group, or a combination thereof, $R^6$ to $R^{11}$ are independently hydrogen, deuterium, a C1 to C4 alkyl group, or a phenyl group, and the "substituted" refers to replacement of at least one hydrogen by deuterium, a C1 to C4 alkyl group, or a C6 to C12 aryl group.

6. The composition for an organic optoelectronic device as claimed in claim 1, wherein the second host compound is represented by one of Chemical Formula 3-I, Chemical Formula 3-II, Chemical Formula 3-III, and Chemical Formula 3-IV:

[Chemical Formula 3-I]

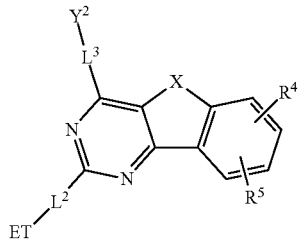

[Chemical Formula 3-II]

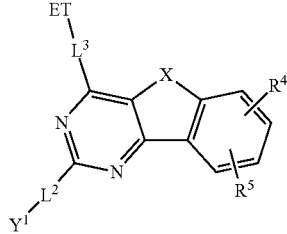

[Chemical Formula 3-III]

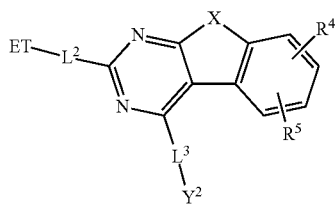

[Chemical Formula 3-IV]

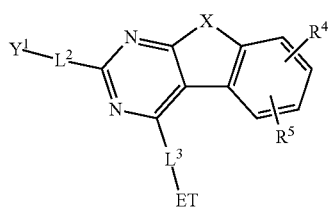

wherein, in Chemical Formula 3-I, Chemical Formula 3-II, Chemical Formula 3-III, and Chemical Formula 3-IV, X is O or S, $L^2$ and $L^3$ are independently a single bond or a substituted or unsubstituted C6 to C30 arylene group, the C6 to C30 arylene group consisting of carbocyclic ring(s), ET is a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolyl group, or a substituted or unsubstituted quinoxalinyl group, $Y^1$ and $Y^2$ are independently a substituted or unsubstituted C6 to C20 aryl group, the C6 to C20 aryl group consisting of carbocyclic ring(s), and $R^4$ and $R^5$ are independently hydrogen, deuterium, a substituted or unsubstituted C1 to C10 alkyl group, a substituted or unsubstituted C6 to C20 aryl group, or a combination thereof, the C6 to C20 aryl group consisting of carbocyclic ring(s).

7. The composition for an organic optoelectronic device as claimed in claim 6, wherein:

L² and L³ are independently a single bond, a substituted or unsubstituted phenylene group, a substituted or unsubstituted biphenylene group, a substituted or unsubstituted terphenylene group, or a substituted or unsubstituted quaterphenylene group, ET is a substituted or unsubstituted pyridyl group, a substituted or unsubstituted pyrimidinyl group, a substituted or unsubstituted triazinyl group, or a substituted or unsubstituted quinazolyl group, Y¹ and Y² are independently a substituted or unsubstituted phenyl group, a substituted or unsubstituted biphenyl group, or a substituted or unsubstituted terphenyl group, R⁴ and R⁵ are independently hydrogen, deuterium, a substituted or unsubstituted C1 to C4 alkyl group, a substituted or unsubstituted phenyl group, or a combination thereof, and the "substituted" refers to replacement of at least one hydrogen by deuterium, a C1 to C4 alkyl group, or a C6 to C12 aryl group.

8. The composition for an organic optoelectronic device as claimed in claim 1, wherein the first host compound is represented by one of Chemical Formula C2, Chemical Formula C3, Chemical Formula C4, Chemical Formula E1, Chemical Formula E2, Chemical Formula E3, Chemical Formula E4, and Chemical Formula F1; and the second host compound is represented by Chemical Formula 3-I:

[Chemical Formula C2]

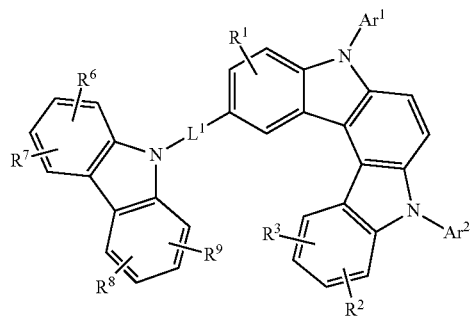

[Chemical Formula C3]

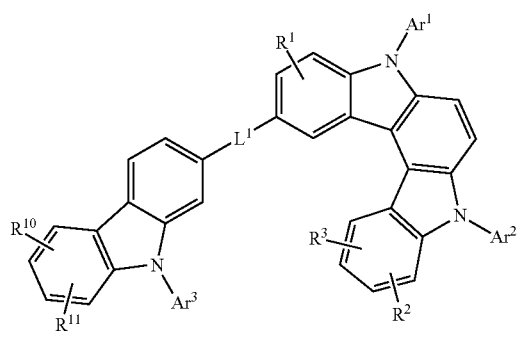

[Chemical Formula C4]

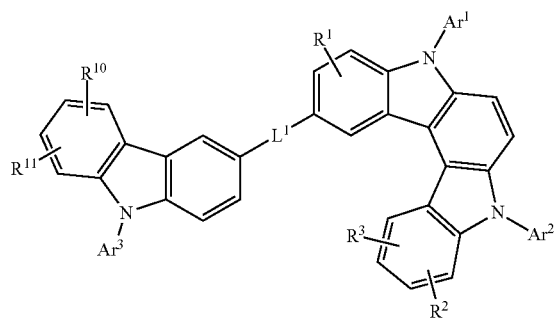

[Chemical Formula E1]

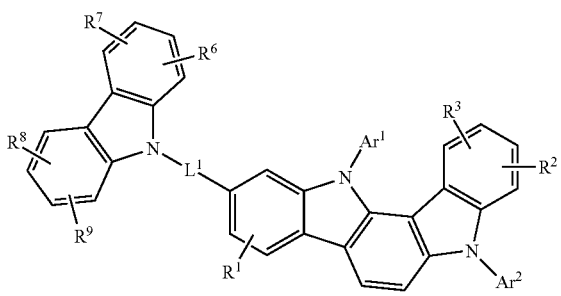

[Chemical Formula E2]

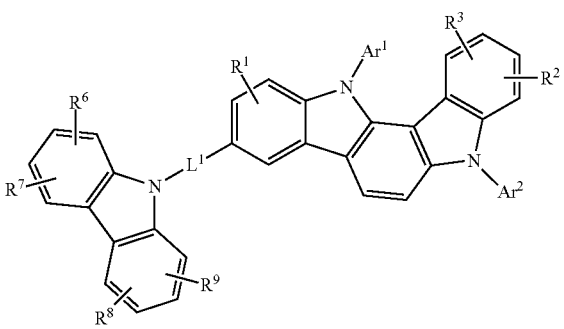

[Chemical Formula E3]

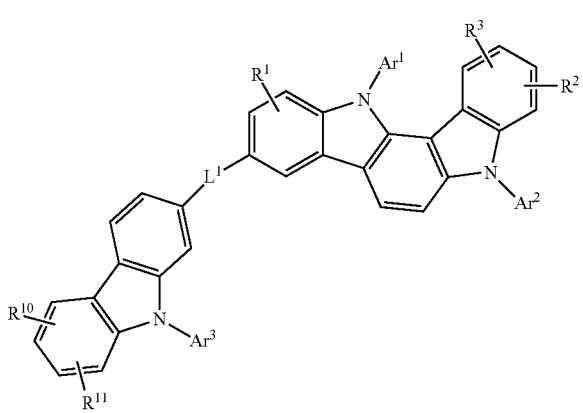

-continued

[Chemical Formula E4]

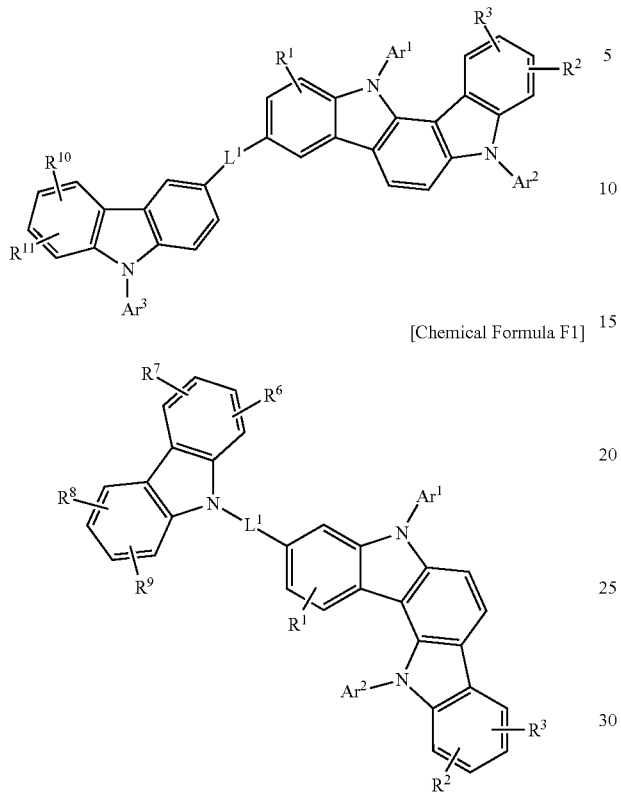

[Chemical Formula F1]

wherein, in Chemical Formula C2, Chemical Formula C3, Chemical Formula C4, Chemical Formula E1, Chemical Formula E2, Chemical Formula E3, Chemical Formula E4, and Chemical Formula F1, $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, or a substituted or unsubstituted triphenylene group, $Ar^3$ is a phenyl group, a biphenyl group, or a naphthyl group, $L^1$ is a single bond, a substituted or unsubstituted phenylene group, or a substituted or unsubstituted biphenylene group, and $R^1$ to $R^3$ are independently hydrogen, deuterium, a substituted or unsubstituted C1 to C4 alkyl group, a substituted or unsubstituted phenyl group, or a combination thereof, $R^6$ to $R^{11}$ are independently hydrogen, deuterium, a C1 to C4 alkyl group, or a phenyl group,

[Chemical Formula 3-I]

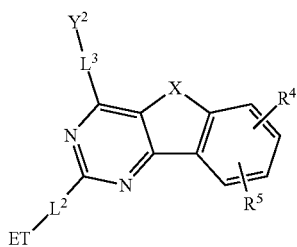

wherein, in Chemical Formula 3-I, $L^2$ and $L^3$ are independently a single bond, a substituted or unsubstituted phenylene group, a substituted or unsubstituted biphenylene group, a substituted or unsubstituted terphenylene group, or a substituted or unsubstituted quaterphenylene group, ET is a substituted or unsubstituted pyridyl group, a substituted or unsubstituted pyrimidinyl group, a substituted or unsubstituted triazinyl group, or a substituted or unsubstituted quinazolyl group, $Y^2$ is a substituted or unsubstituted phenyl group, a substituted or unsubstituted biphenyl group, or a substituted or unsubstituted terphenyl group, $R^4$ and $R^5$ are independently hydrogen, deuterium, a substituted or unsubstituted C1 to C4 alkyl group, a substituted or unsubstituted phenyl group, or a combination thereof.

9. The composition for an organic optoelectronic device as claimed in claim 1, wherein the composition further includes a phosphorescent dopant.

10. An organic optoelectronic device, comprising
an anode and a cathode facing each other, and
at least one organic layer disposed between the anode and the cathode,
wherein the organic layer includes the composition for an organic optoelectronic device as claimed in claim 1.

11. The organic optoelectronic device as claimed in claim 10, wherein the organic layer includes a light emitting layer, and
the composition for an organic optoelectronic device is included as a host of the light emitting layer.

12. A display device comprising the organic optoelectronic device as claimed in claim 10.

13. A composition for an organic optoelectronic device, the composition comprising:
at least one of a first host compound represented by a combination of Chemical Formula 1 and Chemical Formula 2, and
at least one of a second host compound represented by Chemical Formula 3-I, Chemical Formula 3-II, Chemical Formula 3-III, or Chemical Formula 3-IV:

[Chemical Formula 1]

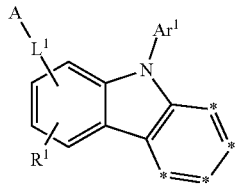

[Chemical Formula 2]

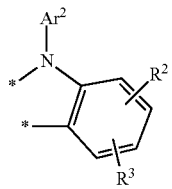

wherein, in Chemical Formulae 1 and 2,
two adjacent *'s of Chemical Formula 1 are bound to two adjacent *'s of Chemical Formula 2 and the remainder *'s of Chemical Formula 1 not being bound to *'s of Chemical Formula 2 are $CR^a$,
the substituent A is a substituted or unsubstituted carbazolyl group, Ar¹ and Ar² are independently a substituted or unsubstituted C6 to C30 aryl group, L¹ is a single bond or a substituted or unsubstituted C6 to C30 arylene group, $R^a$ and $R^1$ to $R^3$ are independently hydrogen, deuterium, a substituted or unsubstituted C1 to C10 alkyl group, a substituted or unsubstituted C6 to C20 aryl group, or a combination thereof,

[Chemical Formula 3-I]

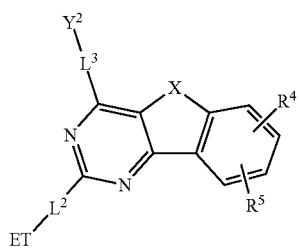

[Chemical Formula 3-II]

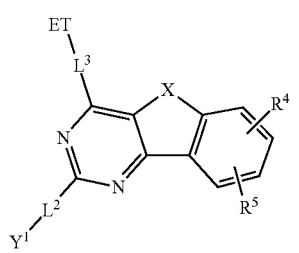

[Chemical Formula 3-III]

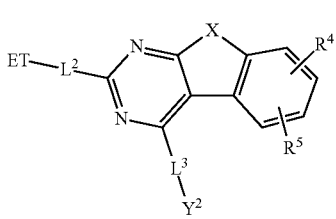

[Chemical Formula 3-IV]

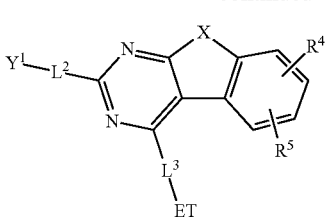

wherein, in Chemical Formula 3-I, Chemical Formula 3-II, Chemical Formula 3-III, and Chemical Formula 3-IV, X is O or S, L² and L³ are independently a single bond, a substituted or unsubstituted phenylene group, a substituted or unsubstituted biphenylene group, a substituted or unsubstituted terphenylene group, or a substituted or unsubstituted quaterphenylene group, ET is a substituted or unsubstituted pyridyl group, a substituted or unsubstituted pyrimidinyl group, a substituted or unsubstituted triazinyl group, or a substituted or unsubstituted quinazolyl group, Y¹ and Y² are independently a substituted or unsubstituted phenyl group, a substituted or unsubstituted biphenyl group, or a substituted or unsubstituted terphenyl group, and R⁴ and R⁵ are independently hydrogen, deuterium, a substituted or unsubstituted C1 to C4 alkyl group, a substituted or unsubstituted phenyl group, or a combination thereof, and the "substituted" refers to replacement of at least one hydrogen by deuterium. a C1 to C4 alkyl group, or a C6 to C12 aryl group.

* * * * *